US012807701B2

(12) United States Patent
Wong et al.

(10) Patent No.: US 12,807,701 B2
(45) Date of Patent: Nov. 24, 2026

(54) MICROFIBRILLAR-ASSOCIATED PROTEIN 5 (MFAP5)-TARGETING MONOCLONAL ANTIBODIES AND METHODS FOR USE IN TREATING CANCER

(71) Applicants: The Methodist Hospital, Houston, TX (US); Board of Regents, The University of Texas System, Houston, TX (US)

(72) Inventors: Stephen T.C. Wong, Missouri City, TX (US); Jianting Sheng, Pearland, TX (US); Samuel C. Mok, Sugar Land, TX (US); Cecilia S. Leung, Missouri City, TX (US); Tsz-Lun Yeung, Houston, TX (US)

(73) Assignees: BOARD OF REGENTS, THE UNIVERSITY OF TEXAS SYSTEM, Austin, TX (US); THE METHODIST HOSPITAL, Houston, TX (US)

( * ) Notice: Subject to any disclaimer, the term of this patent is extended or adjusted under 35 U.S.C. 154(b) by 165 days.

(21) Appl. No.: 16/936,421

(22) Filed: Jul. 22, 2020

(65) Prior Publication Data

US 2024/0199735 A1 Jun. 20, 2024

Related U.S. Application Data

(60) Provisional application No. 62/877,298, filed on Jul. 22, 2019.

(51) Int. Cl.

| | |
|---|---|
| ***C07K 16/28*** | (2006.01) |
| ***A61K 45/06*** | (2006.01) |
| ***A61P 35/00*** | (2006.01) |
| ***G01N 33/57545*** | (2026.01) |
| ***G01N 33/58*** | (2006.01) |
| ***G01N 33/60*** | (2006.01) |

(52) U.S. Cl.

CPC .............. *C07K 16/28* (2013.01); *A61K 45/06* (2013.01); *A61P 35/00* (2018.01); *G01N 33/57545* (2026.01); *G01N 33/582* (2013.01); *G01N 33/60* (2013.01); *C07K 2317/56* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 4,935,496 | A | 6/1990 | Kudo et al. |
| 5,502,167 | A | 3/1996 | Waldmann et al. |
| 5,530,101 | A | 6/1996 | Queen et al. |
| 5,558,864 | A | 9/1996 | Bendig et al. |
| 5,565,332 | A | 10/1996 | Hoogenboom et al. |
| 5,585,089 | A | 12/1996 | Queen et al. |
| 5,639,641 | A | 6/1997 | Pedersen et al. |
| 5,639,757 | A | 6/1997 | Dow et al. |
| 5,693,493 | A | 12/1997 | Robinson et al. |
| 5,693,761 | A | 12/1997 | Queen et al. |
| 5,693,762 | A | 12/1997 | Queen et al. |
| 5,698,417 | A | 12/1997 | Robinson et al. |
| 5,705,154 | A | 1/1998 | Dalie et al. |
| 5,712,291 | A | 1/1998 | D'Amato |
| 5,733,743 | A | 3/1998 | Johnson et al. |
| 5,750,078 | A | 5/1998 | Shitara et al. |
| 5,753,230 | A | 5/1998 | Brooks et al. |
| 5,770,403 | A | 6/1998 | Dalie et al. |
| 5,855,866 | A | 1/1999 | Thorpe et al. |
| 5,877,289 | A | 3/1999 | Thorpe et al. |
| 5,965,132 | A | 10/1999 | Thorpe et al. |
| 5,972,922 | A | 10/1999 | Wilks et al. |
| 6,004,555 | A | 12/1999 | Thorpe et al. |
| 6,051,230 | A | 4/2000 | Thorpe et al. |
| 2016/0009806 | A1* | 1/2016 | Ryan ................ A61K 47/68031 536/23.53 |

FOREIGN PATENT DOCUMENTS

| | | | |
|---|---|---|---|
| EP | 0404097 | A2 | 12/1990 |
| WO | 9311161 | A1 | 6/1993 |
| WO | 9632478 | A1 | 10/1996 |
| WO | 9816551 | A2 | 4/1998 |
| WO | 9845331 | A2 | 10/1998 |
| WO | 9845332 | A2 | 10/1998 |

OTHER PUBLICATIONS

Dondelinger, 2018, Front. Immunol. vol. 9: 1-15.*
Chen, 1992, J. Exp. Med. vol. 176: 855-866.*
Hall, 1992, J. Immunol. vol. 149: 1605-1612.*
Rabia et al. 2018, Biochem. Eng. J. vol. 137: 365-374.*
Altschul , et al., Gapped BLAST and PSI-BLAST: A New Generation of Protein Database Search Programs, Nucleic Acids Research, vol. 25, No. 17, Sep. 1, 1997, pp. 3389-3402.
Asano , et al., Increased Expression of Integrin Alpha(V)beta3 Contributes to the Establishment of Autocrine Tgf-beta Signaling in Scleroderma Fibroblasts, The Journal of Immunology, vol. 175, No. 11, Dec. 2005, pp. 7708-7718.
Barcus , et al., Stiff Collagen Matrices Increase Tumorigenic Prolactin Signaling in Breast Cancer Cells, Journal of Biological Chemistry, vol. 288, No. 18, May 2013, pp. 12722-12732.
Brouwers , et al., The Footprint of the Ageing Stroma in Older Patients With Breast Cancer, Breast Cancer Research, vol. 19, 2017, 14 pages.
Cobleigh , et al., Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease, Journal of Clinical Oncology, vol. 17, No. 9, Sep. 1999, pp. 2639-2648.

(Continued)

*Primary Examiner* — Amy E Juedes

(74) *Attorney, Agent, or Firm* — Kilpatrick Townsend & Stockton LLP

(57) ABSTRACT

Disclosed are antibody compositions and methods for treatment mammalian cancers. Also disclosed are methods for use of the disclosed MFAP5-specific monoclonal antibodies and antigen-binding-fragments thereof, in the treatment, prophylaxis, and/or the amelioration of one or more symptoms of mammalian cancer, including human ovarian and pancreatic cancers, in particular.

28 Claims, 54 Drawing Sheets

Specification includes a Sequence Listing.

(56) References Cited

OTHER PUBLICATIONS

Correia, et al., The Tumor Microenvironment is a Dominant Force in Multidrug Resistance, Drug Resistance Updates, vol. 15, Feb.-Apr. 2012, pp. 39-49.
Cox, et al., Remodeling and Homeostasis of the Extracellular Matrix: Implications for Fibrotic Diseases and Cancer, Disease Models & Mechanisms, vol. 4, 2011, pp. 165-178.
Goel , et al., Vascular Normalization as a Therapeutic Strategy for Malignant and Nonmalignant Disease, Cold Spring Harbor Perspectives in Medicine, vol. 2, No. 3, Mar. 2012, 24 pages.
Gribskov , et al., Sigma Factors from *E. coli*, B. Subtils, Phage SPOI, and Phage T4 are Homologous Proteins, Nucleic Acids Research, vol. 14, No. 16, Aug. 1986, pp. 6745-6763.
Hardman , et al., Goodman & Gilman's the Pharmacological Basis of Therapeutics, 10th Edition, Chapter 1, ISBN 0-07-135469-7, 2001, pp. 3-29.
Hu , et al., Generation of a Monoclonal Antibody Against the Glycosylphosphatidylinositol-linked Protein Rae-1 Using Genetically Engineered Tumor Cells, Biological Procedures Online, vol. 16, No. 3, Feb. 2014, 8 pages.
Hurwitz , Integrating the Anti-VEGF—A Humanized Monoclonal Antibody Bevacizumab with Chemotherapy in Advanced Colorectal Cancer, Clinical Colorectal Cancer, vol. 4, Oct. 2004, pp. S62-S68.
Jia, et al., Diagnosis of Prostate Cancer Using Differentially Expressed Genes in Stroma, Cancer Research, vol. 71, No. 7, Apr. 2011, pp. 2476-2487.
Joyce, et al., Phenotypic Basis for Matrix Stiffness-Dependent Chemoresistance of Breast Cancer Cells to Doxorubicin, Frontiers in Oncology, vol. 8, Sep. 2018, 9 pages.
Joyce , Therapeutic Targeting of the Tumor Microenvironment, Cancer Cell, vol. 7, No. 6, Jun. 2005, pp. 513-520.
Kyte , et al., A Simple Method for Displaying the Hydropathic Character of a Protein, Journal of Molecular Biology, vol. 157, No. 1, May 5, 1982, pp. 105-132.
Lee , et al., Synthesis of a Fluorescent Analogue of Paclitaxel That Selectively Binds Microtubules and Sensitively Detects Efflux by P-glycoprotein, Angewandte Chemie International Edition, vol. 56, No. 24, Jun. 2017, pp. 6927-6931.
Leung, et al., Calcium-Dependent FAK/CREB/TNNC1 Signalling Mediates the Effect of Stromal Mfap5 on Ovarian Cancer Metastatic Potential, Nature Communications, vol. 5, Oct. 3, 2014, 15 pages.
Leung, et al., Cancer-Associated Fibroblasts Regulate Endothelial Adhesion Protein LPP to Promote Ovarian Cancer Chemoresistance, Journal of Clinical Investigation, vol. 128, No. 2, Feb. 2018, pp. 589-606.
Lopez-Casas , et al., Gene-Expression Profiling in Pancreatic Cancer, Expert Review of Molecular Diagnostics, vol. 10, No. 5, Jul. 2010, pp. 1-14.
McCarroll , et al., Role of Pancreatic Stellate Cells in Chemoresistance in Pancreatic Cancer, Frontiers in Physiology, vol. 5, Apr. 2014, 9 pages.
Micke , et al., Tumour-stroma Interaction: Cancer-associated Fibroblasts as Novel Targets in Anti-cancer Therapy?, Lung Cancer, vol. 45, Aug. 2004, pp. S163-S175.
Mok, et al., A Gene Signature Predictive for Outcome in Advanced Ovarian Cancer Identifies a Survival Factor: Microfibril-Associated Glycoprotein 2, Cancer Cell, vol. 16, No. 6, Dec. 8, 2009, pp. 521-532.
Navab , et al., Prognostic Gene-Expression Signature of Carcinoma-associated Fibroblasts in Non-small Cell Lung Cancer, Proceedings of the National Academy of Sciences of the United States of America, vol. 108, No. 17, Apr. 26, 2011, pp. 7160-7165.
Needleman , et al., A General Method Applicable to the Search for Similarities in the Amino Acid Sequence of Two Proteins, Journal of Molecular Biology, vol. 48, No. 3, Mar. 1970, pp. 443-453.
Ohlund, et al., Distinct Populations of Inflammatory Fibroblasts and Myofibroblasts in Pancreatic Cancer, Journal of Experimental Medicine, vol. 214, No., 3, Mar. 2017, pp. 579-596.
Oldham , et al., Monoclonal Antibodies in Cancer Therapy: 25 Years of Progress, Journal of Clinical Oncology, vol. 26, No. 11, Apr. 10, 2008, pp. 1774-1777.
Postow, Immune Checkpoint Blockade in Cancer Therapy, Journal of Clinical Oncology, vol. 33, No. 17, Jun. 10, 2015, pp. 1974-1982.
Qin , et al., Novel BAFF-Receptor Antibody to Natively Folded Recombinant Protein Eliminates Drug-Resistant Human B-cell Malignancies In Vivo, Clinical Cancer Research, vol. 24, No. 5, Mar. 2018, pp. 1114-1123.
Rada, et al., Inhibitor of Apoptosis Proteins (laps) Mediate Collagen Type Xi Alpha 1-driven Cisplatin Resistance in Ovarian Cancer, Oncogene, vol. 37, May 2018, pp. 4809-4820.
Rieger , et al., Glossary of Genetics, Classical and Molecular, 5th Edition, 1991, 551 pages.
Romond , et al., Trastuzumab Plus Adjuvant Chemotherapy for Operable HER2-Positive Breast Cancer, The New England Journal of Medicine, vol. 353, No. 16, Oct. 2005, pp. 1673-1684.
Shields , et al., Biochemical Role of the Collagen-Rich Tumour Microenvironment in Pancreatic Cancer Progression, Biochemical Journal, vol. 441, No. 2, Jan. 15, 2012, pp. 541-552.
Slamon , et al., Adjuvant Trastuzumab in HER2-Positive Breast Cancer, The New England Journal of Medicine, vol. 365, No. 14, Oct. 6, 2011, pp. 1273-1283.
Tewari , et al., Bevacizumab for Advanced Cervical Cancer: Final Overall Survival and Adverse Event Analysis of a Randomised, Controlled, Open-label, Phase 3 Trial (Gynecologic Oncology Group 240), Lancet, vol. 390, No. 10103, Jul. 2017, pp. 1654-1663.
Tlsty , et al., Tumor Stroma and Regulation of Cancer Development, Annual Review of Pathology: Mechanisms of Disease, vol. 1, Feb. 2006, pp. 119-150.
Uhlen , et al., A Human Protein Atlas for Normal and Cancer Tissues Based on Antibody Proteomics, Molecular & Cellular Proteomics, vol. 4, No. 12, Aug. 2005, pp. 1920-1932.
Uhlen , et al., A Proposal for Validation of Antibodies, Nature Methods, vol. 13, No. 10, Sep. 5, 2016, pp. 823-827.
Uhlen , et al., Towards a Knowledge-Based Human Protein Atlas, Nature Biotechnology, vol. 28, No. 12, Dec. 2010, pp. 1248-1250.
Voo, et al., Antibodies Targeting Human OX40 Expand Effector T Cells and Block Inducible and Natural Regulatory T Cell Function, Journal of Immunology, vol. 191, No. 7, Sep. 2013, pp. 3641-3650.
Yazdani , Drug Targeting to Myofibroblasts: Implications for Fibrosis and Cancer, Advanced Drug Delivery Reviews, vol. 121, Jul. 2017, pp. 101-116.
Yeung, et al., Cellular and molecular processes in ovarian cancer metastasis. A Review in the Theme: Cell and Molecular Processes in Cancer Metastasis, American Journal of Physiology-Cell Physiology, vol. 309, No. 7, Jul. 2015, pp. C444-C456.

* cited by examiner

Ovarian Cancer
- Ovarian cancer is the most lethal gynecologic cancer
- Women living with ovarian cancer in the US: >220,000
- New diagnosis: ~22,000/yr
- Mortality: ~14,000/yr
- Low 5-year survival rate: 28% and 19% for stage III and IV disease Pancreatic Cancer
- Pancreatic cancer is the most lethal cancer
- People living with pancreatic cancer in the US: >68,000
- New diagnosis: ~55,000/yr
- Mortality: ~44,000/yr
- Low 5-year survival rate: 3% and 1% for stage III and IV disease

- Both ovarian and pancreatic cancer are often
- diagnosed at advanced disease stage
- Both cancers have no significant improvement
- In patient survival due to lack of drugs

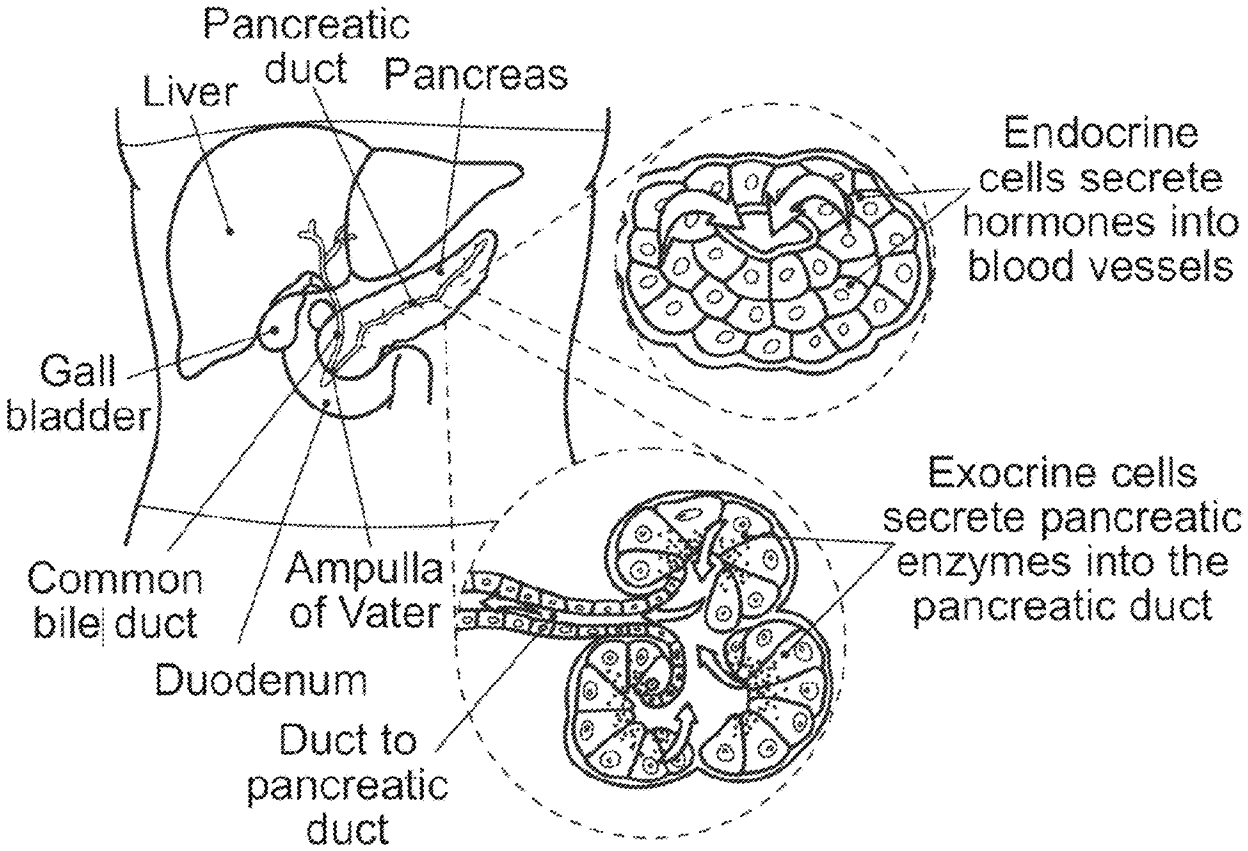

FIG. 1 (cont'd)

MFAP5 is a novel target for cancer treatment

Leung et al., Nat Commun., 2014; Leung et al., J Clin Invest., 2018

Clones recognize human MFAP5

64A, 117b (SEQ ID NO:1)

```
Human MFAP5  MSLLGPKVLLFLAAFIITSDWIPLGVNSQRGDDVTQATPETFTEDPNLVNDPATDETVLA
Mouse MFAP5  MLFLGQKALLLVLAISIPSDWLPLGVSGQRGDDV----PETFTDDPNLVNDPSTDDTAL-
             *  :** *.**:: *: * ***:****..******    *****:********:**:*.*
```

(SEQ ID NO:2)

```
Human MFAP5  VLADIAPSTDDLASLSEKNTTAECWDEKFTCTRLYSVHRPVKQCIHQLCFTSLRRMYIVN
Mouse MFAP5  --ADITPSTDDLA--GDKNATAECRDEKFACTRLYSVHRPVRQCVHQSCFTSLRRMYIIN
               ***:*******  .:**:**** ****:***********:**:** **********:*

Human MFAP5  KEICSRLVCKEHEAMKDELCRQMAGLPPRRLRRSNYFRLPPCENVDLQRPNGL
Mouse MFAP5  NEICSRLVCKEHEAMKDELCRQMAGLPPRRLRRSNYFRLPPCENMNLQRPDGL
             :*******************************************::****:**
```

130A

Clone recognizes both human and mouse MFAP5

Human MFAP5 – 167 aa

Mouse MFAP5 – 164 aa

FIG. 7C

Control IgG

130A

Control IgG treated mice

MFAP5 monoclonal antibody treated mice

Graphical presentation of ELISA verification result.

| No. | Peptide | |
|---|---|---|
| 17 | VNDPATDETVLAVLA | (SEQ ID NO:5) |
| 18 | PATDETVLAVLADIA | (SEQ ID NO:6) |
| 19 | DETVLAVLADIAPST | (SEQ ID NO:7) |

Epitope of anti-MFAP5 antibody

| No. | Peptide | |
|---|---|---|
| 43 | KDELSRQMAGLPPRR | (SEQ ID NO:8) |
| 44 | LSRQMAGLPPRRLRR | (SEQ ID NO:9) |

Control IgG treated mice

MFAP5 monoclonal antibody treated mice

MICROFIBRILLAR-ASSOCIATED PROTEIN 5 (MFAP5)-TARGETING MONOCLONAL ANTIBODIES AND METHODS FOR USE IN TREATING CANCER

CROSS-REFERENCE TO RELATED APPLICATIONS

The present application claims priority to U.S. Provisional Patent Application No. 62/877,298, filed Jul. 22, 2019, the content of which is specifically incorporated herein in its entirety by express reference thereto.

STATEMENT REGARDING FEDERALLY SPONSORED RESEARCH OR DEVELOPMENT

This invention was made with government support under W81XWH-17-1-0126 awarded by the Defense Health Agency, Medical Research and Development Branch. The government has certain rights in the invention.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named "090723_1340134_13_151US_Sequence Listing_ST25.txt", created on Feb. 14, 2023, and having a size of 37 kilobytes. The sequence listing contained in this ASCII formatted document is part of the specification and is herein incorporated by reference in its entirety.

NAMES OF THE PARTIES TO A JOINT RESEARCH AGREEMENT

Not Applicable.

FIELD OF THE DISCLOSURE

The present invention relates to molecular biology, immunology, and medical oncology. Disclosed are antibody compositions specific for Microfibrillar-Associated Protein 5 (MFAP5), and methods for their use in the treatment of various mammalian diseases and disorders, and particularly for the treatment of human tumors and other forms of cancer.

BACKGROUND

Description of the Related Art

Tumor Microenvironment

The tumor microenvironment, composed primarily by fibroblasts, endothelial cells, lymphocytic infiltrates and extracellular matrix proteins, can directly affect cancer cell growth, migration, and differentiation (Tlsty and Coussens, 2006), thereby presenting a unique aspect of diagnosing and treating cancer. Cancer associated fibroblasts (CAFs) are primarily responsible for producing the structural components of the stromal microenvironment, which is mostly composed of collagen type I, II and IV as well as fibronectin (Tlsty and Coussens, 2006). CAFs also produce secreted factors such as cytokines and growth factors, which maintain normal tissue homeostasis by signaling to other cell components in the stroma, such as immune, fat, vascular, smooth muscle and epithelial cells. CAFs in the tumor stromal microenvironment exhibit altered secretion of extracellular proteins as well as paracrine growth factors, which modify the niche of tumor microenvironment and promote cancer cell proliferation, migration, and invasion.

Microfibrillar-associated protein 5 (MFAP5), a 25-kDa glycoprotein, has recently been shown to be up-regulated in CAF of multiple tumor types including non-small cell lung cancer (Navab et al, 2011), pancreatic (Lopez-Casas and Lopez-Fernandez, 2010), ovarian (Leung et al., 2014), prostate (Jia et al., 2011), and breast cancer (Brouwers et al, 2017). In addition, over-expression of MFAP5 in CAFs has been shown to be associate with poor prognosis in ovarian cancer (Leung et al, 2014), and used as a diagnostic marker for prostate cancer early detection (Jia et al, 2011). MFAP5 has a RGD binding motif, which can bind $\alpha_v\beta_3$ integrin to enhance angiogenesis and ovarian cancer metastasis potential through the activation of calcium-dependent FAK/EREK/LPP and FAK/CREB/TNNC1 signaling pathway (Leung et al., 2014; Mok et al., 2009; Leung et al., 2018). These findings suggest that treatment strategies based on targeting CAF-derived MFAP5 activities may be a new modality in suppressing cancer cell growth and metastasis.

Antibodies as Cancer Therapeutics

Monoclonal antibodies (MAbs) have been shown to be effective therapeutic agents for a number of human malignancies. Several of them have been approved as new therapeutic agents for the treatment of human cancer in the last decade. For example, trastuzumab (HERCEPTIN®), a humanized anti-HER2/neu MAb has been used alone or in combination with chemotherapy for the treatment of metastatic breast cancer in patients with tumors overexpressing HER2/neu (Slamon et al., 2011; Cobleigh et al., 1999; Romond et al., 2005). Bevacizumab, a recombinant humanized MAb against vascular endothelial growth factor (VEGF) improves survival in colorectal (Hurwitz, 2004) and cervical (Tewari et al., 2017) cancer patients. In addition to antibodies targeting antigens on cancer cells, MAbs targeting immune checkpoint molecules on T cells have recently been approved by the FDA. Pembrolizumab, a MAb targeting programmed cell death 1 (PD-1) and Ipilimumab, another MAb targeting cytotoxic T-lymphocyte associated protein 4 (CTLA-4) on T cells have been developed and used for the treatment of advanced melanoma and other cancer types (Postow et al., 2015).

Deficiencies in the Prior Art

Despite the advances to date in antibody-based therapeutics, the efficacy of targeting CAF-derived antigens by MAbs in cancer treatment has not been thoroughly explored. The identification of additional agents that inhibit MFAP5 would be of benefit in expanding the number of therapeutic options. Moreover, the development of therapeutic agents that more specifically inhibit MFAP5 receptor binding would represent an important advance, so long as their anti-tumor effects were not substantially compromised by the improved specificity.

What is lacking in the prior art is MAbs that specifically target CAF-derived MFAP5, and are suitable for the treatment of cancers, and particularly ovarian and pancreatic tumors.

SUMMARY

The present invention overcomes these and other certain drawbacks in the prior art by providing new therapeutic compositions and methods for use in anti-fibrosis and anti-tumor therapy. Disclosed are monoclonal antibodies (MAbs) that are useful as therapeutic agents in high-grade serous ovarian cancer (HGSC) and pancreatic ductal adenocarcinoma (PDAC) patients.

MFAP5 serves as a novel therapeutic target in ovarian and pancreatic cancer and monoclonal MFAP5-targeting antibodies serve as therapeutic agents in ovarian and pancreatic cancer treatment. Among other things, the invention finds particular use in:

1) prevention of MFAP5 binding to its receptor on cancer cells by monoclonal antibodies, hence inhibiting the invasion potential of ovarian cancer cells;
2) prevention of MFAP5 binding to its receptor on endothelial cells by monoclonal antibodies, hence suppressing the microvessel formation. (antiangiogenic therapy); and
3) combination therapies which combine MFAP5-targeting monoclonal antibodies with conventional chemo therapies.

The invention is exemplified by monoclonal antibody 130A, produced by hybridoma ATCC X, or an antigen-binding fragment of such a monoclonal antibody. A hybridoma that produces a monoclonal anti-MFAP5 antibody that binds to substantially the same epitope as the monoclonal antibody 130A (ATCC X) is another aspect of the invention.

The invention further provides anti-MFAP5 antibodies that bind to substantially the same epitope as the monoclonal antibody 130A (ATCC X), prepared by a process comprising immunizing an animal with at least a first immunogenic MFAP5 component and selecting from the immunized animal an antibody that substantially cross-reacts with the monoclonal antibody 130A (ATCC X); and anti-MFAP5 antibodies that bind to substantially the same epitope as the monoclonal antibody 130A (ATCC X), prepared by a process comprising immunizing an animal with at least a first immunogenic MFAP5 component and selecting a cross-reactive anti-MFAP5 antibody from the immunized animal by identifying an antibody that substantially reduces the binding of the 130A antibody to MFAP5.

Anti-MFAP5 antibodies, or antigen-binding fragments thereof, that bind to substantially the same epitope as the monoclonal antibody 130A (ATCC X) and that specifically inhibits MFAP5 polypeptide binding to a MFAP5 receptor; and anti-MFAP5 antibodies, or antigen-binding fragments thereof, that bind to substantially the same epitope as the monoclonal antibody 130A (ATCC X) and that inhibits MFAP5 binding to the MFAP5 receptor forms other aspects of the present disclosure.

Antibodies with such combinations of properties can be readily identified by one or more or a combination of the receptor competition, ELISA, co-precipitation, and/or functional assays and the 130A-crossreactivity assays described above. The guidance concerning the quantitative assessment of 130A-like antibodies that consistently significantly reduce MFAP5 binding to am MFAP5 receptor and that consistently do not significantly inhibit MFAP5 binding to MFAP5 receptor is as described above.

In another embodiment, the present disclosure provides an antibody, or an antigen-binding fragment thereof, that specifically binds to a mammalian Microfibrillar-Associated Protein 5 (MFAP5) polypeptide, or a peptide epitope thereof.

In particular aspects of the disclosure, the antibody is a monoclonal antibody that specifically binds to a MFAP5 polypeptide sequence that is at least 95% identical, at least 97% identical, or at least 99% identical to the amino acid sequence of SEQ ID NO:1 or SEQ ID NO:2, which are the human and murine MFAP5 polypeptides, respectively, or to a MFAP5 peptide epitope sequence that is at least 95% identical, at least 97% identical, or at least 99% identical to the amino acid sequence of any one of SEQ ID NO:3 to SEQ ID NO:15.

In other aspects, the antigen-binding fragment is one obtained from an antibody (and particularly from a monoclonal antibody such as the "130A" antibody herein), and that specifically binds to a MFAP5 polypeptide sequence that is at least 95% identical, at least 97% identical, or at least 99% identical to the amino acid sequence of SEQ ID NO:1 or SEQ ID NO:2, or to a MFAP5 peptide epitope sequence that is at least 95% identical, at least 97% identical, or at least 99% identical to the amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:15.

In still other aspects of the present disclosure, the antibody is a monoclonal antibody that specifically binds to a MFAP5 polypeptide sequence that comprises the amino acid sequence of SEQ ID NO:1 or SEQ ID NO:2, or to a MFAP5 peptide epitopic sequence that comprises, consists essentially of, or alternatively, consists of, the amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:15.

In yet further aspects, exemplary antigen-binding fragments include those that specifically bind to a MFAP5 polypeptide sequence that comprises the amino acid sequence of SEQ ID NO:1 or SEQ ID NO:2, or to a MFAP5 peptide epitopic sequence that comprises, consists essentially of, or alternatively, consists of, the amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:15.

In related embodiments, the present disclosure also provides compositions that comprise one or more such antibodies, or antigen-binding fragments thereof, and a pharmaceutically-acceptable buffer, diluent, carrier, or vehicle. Such compositions may further optionally comprise one or more adjuvants, such as alum, one or more additional distinct antibodies or antigen binding fragments, one or more chemotherapeutic agents, one or more diagnostic agents, or any combination thereof.

Preferably the antibody/antigen-binding fragment-based compositions disclosed herein are adapted and configured for (1) decreasing MFAP5 expression, (2) reducing fibrosis, (3) decreasing collagen accumulation, (4) inhibiting cancer cell motility, (5) suppressing tumor progression, or (6) any combination thereof, when introduced into suitable mammalian tumors, mammalian cancer cells, mammalian cancer-associated fibroblasts (CAFs), or any combination thereof.

In certain clinical formulations of the disclosed compositions, it may be desirable for the composition to further comprise one or more chemotherapeutic agents, immunomodulating agents, neuroactive agents, anti inflammatory agents, anti lipidemic agents, hormones, receptor agonists, receptor antagonists, anti-infective agents, anti-bacterial agents, anti-microbial agents, anti-fungal agents, proteins, peptides, nucleic acid molecules (including, but not limited to RNAs, DNAs, siRNAs, mRNAs, ribozymes, antisense molecules, etc.), hormones, cofactors, steroids, or any combination thereof.

In particular aspects of the invention, the chemotherapeutic agent may include one or more antineoplastic compounds, one or more cytotoxic compounds, one or more cytostatic compounds, or any combination thereof, and may be selected from the group consisting of cyclophosphamide, doxorubicin, 5-fluorouracil, docetaxel, paclitaxel, trastuzumab, methotrexate, epirubicin, cisplatin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, and any combination thereof.

The compositions disclosed herein may optionally be (a) formulated within a population of liposomes, nanoparticles, microparticles, or any combination thereof, or (b) admixed with one or more surfactants, niosomes, ethosomes, transferosomes, phospholipids, sphingosomes, or any combination thereof, and preferably formulated for systemic administration to a mammal, and more preferably still, formulated for intravenous administration to a human.

In further aspects, the anti-MFAP5 antibodies disclosed herein may be adapted and configured as part of a therapeutic kit that comprises the composition, and at least a first set of instructions for administration of the composition to a human in need thereof.

The compositions of the present disclosure find particular use in therapy, prophylaxis, or amelioration of one or more symptoms of a mammalian cancer, particularly human cancers, such as ovarian or pancreatic tumorigenic cancers.

Also provided is an isolated population of mammalian cells that comprise one or more of the antibodies, antigen-binding fragments, or pharmaceutical formulations disclosed herein.

Likewise, the use of an antibody antigen-binding fragment, or a pharmaceutical composition disclosed herein is also provided for the manufacture of a medicament for treating or ameliorating at least one symptom of a cancer in a mammalian subject, and preferably a human, a non-human primate, a companion animal, an exotic, or a livestock.

In further embodiments, the disclosure provides a kit that includes 1) a MFAP5-specific antibody, antigen-binding fragment, or pharmaceutical composition; and 2) instructions for administering the composition to a mammal in need thereof, as part of a regimen for the prevention, diagnosis, treatment, or amelioration of one or more symptoms of cancer.

A method of treating or ameliorating one or more symptoms of cancer in an animal in need thereof is also set forth in the present disclosure. In an overall and general sense, the method generally includes at least the step of administering to an animal in need thereof, an effective amount of a MFAP5-specific antibody, antigen-binding fragment, or pharmaceutical composition, for a time sufficient to treat or ameliorate the one or more symptoms of the cancer in the animal.

In some embodiments of the method of treating or ameliorating one or more symptoms of cancer, the cancer is a refractory, a metastatic, a relapsed, or a treatment resistant cancer. In particular embodiments, the animal is a mammal, such as a human, that has been diagnosed with a tumorigenic cancer such as ovarian cancer, pancreatic cancer, or related hyperproliferative disorders. Such methods may further optionally include an additional step of administering a therapeutically effective amount of ionizing radiation; a chemotherapeutic agent, or a combination thereof to the animal undergoing antibody-mediated therapy. Such compositions may be administered systemically to the animal, in a single administration, or in a series of multiple administrations over a period of from one, two, three or more days, over a period of one, two, three or more weeks, or even over a period of one, two, three, or more months, depending upon the particular indication, condition, and responsiveness of the patient to the administered therapy.

A method of reducing the level of biologically-active MFAP5 polypeptide in one or more cells, tissues, or organs of a mammal also forms part of the present disclosure. In an overall and general sense, such methods generally include at least the step of administering to a mammal in need thereof a MFAP5-specific antibody, antigen-binding fragment, or pharmaceutical composition in an amount effective and for a time sufficient to reduce the level of biologically-active MFAP5 polypeptide in the one or more cells, tissues, or organs of the mammal.

In another embodiment, a method for reducing the degree of fibrosis or the extent of collagen development in the tumor microenvironment of a mammal diagnosed with cancer is also provided. In an overall and general sense, such methods generally include at least the step of administering to a mammal in need thereof a MFAP5-specific antibody, antigen-binding fragment, or MFAP5 antibody pharmaceutical composition in an amount effective, and for a time sufficient, to reduce the degree of fibrosis, or the extent of collagen development in the mammal.

In further aspects of the disclosure, a method for inhibiting cancer cell motility or suppressing tumor progression in a mammal is also provided. In an overall and general sense, such methods generally include at least the step of administering to a mammal in need thereof: a MFAP5-specific antibody, antigen-binding fragment, or MFAP5 antibody pharmaceutical composition in an amount effective and for a time sufficient to inhibit the motility of one or more cancer cells or to suppress the progression of one or more tumors in the mammal.

Additional exemplary anti-MFAP5 antibodies (and antigen-binding fragments) of the invention are therefore those that:

- bind to a non-conformationally dependent MFAP5 epitope, as assessed by binding to MFAP5 in a Western blot;
- bind to free MFAP5;
- significantly inhibit MFAP5 binding to the MFAP5 receptor;
- do not significantly bind to any other polypeptide in mammalian cells;
- inhibit, and preferably, significantly inhibit, MFAP5-induced fibrosis;
- inhibit, and preferably, significantly inhibit, MFAP5-induced tumor progression;
- inhibit, and preferably, significantly inhibit, MFAP5-mediated cancer cell proliferation; and
- bind to the same or substantially the same epitope as the monoclonal antibody 130A (ATCC XXXX).

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region thereof, unless otherwise specifically stated or made clear from the scientific terminology, refer to a range of anti-MFAP5 antibodies as well as to specific 130A-cross-reactive antibodies.

Generally, where antibodies, rather than antigen binding regions, are used in the invention, IgG and/or IgM are preferred because they are the most common antibodies in the physiological situation and because they are most easily made in a laboratory setting.

Suitable antibody-producing cells may also be obtained, and antibodies subsequently isolated and/or purified, by stimulating peripheral blood lymphocytes with MFAP5 in vitro.

Other methods comprise administering to an animal an immunizing composition comprising at least a first immunogenic MFAP5 component and selecting from the immunized animal an antibody that significantly inhibits MFAP5 binding to its receptor, and optionally that substantially cross-reacts with the monoclonal antibody 130A (ATCC X). In an overall and general sense, these methods generally comprise at least the steps of:

(a) immunizing an animal by administering to the animal at least one dose, and optionally more than one dose, of an immunogenically effective amount of an immunogenic MFAP5 sample (such as a first human MFAP5 component, a substantially full length MFAP5 component, or recombinant human MFAP5); and (b) obtaining a suitable antibody-producing cell from the immunized animal, such as an antibody-producing cell that produces an antibody that significantly inhibits MFAP5 binding to its receptor, and optionally that substantially cross-reacts with the monoclonal antibody 130A (ATCC X).

As non-human animals are used for immunization, the monoclonal antibodies obtained from such a hybridoma will often have a non-human make up. Such antibodies may be optionally subjected to a humanization process, grafting or mutation, as known to those of skill in the art and further disclosed herein. Alternatively, transgenic animals, such as mice, may be used that comprise a human antibody gene library. Immunization of such animals will therefore directly result in the generation of suitable human antibodies.

After the production of a suitable antibody-producing cell, most preferably a hybridoma, whether producing human or non-human antibodies, the monoclonal antibody-encoding nucleic acids may be cloned to prepare a "recombinant" monoclonal antibody. Any recombinant cloning technique may be utilized, including the use of PCR™ to prime the synthesis of the antibody-encoding nucleic acid sequences. Therefore, yet further appropriate monoclonal antibody preparative methods include those that comprise using the antibody-producing cells as follows: (a) obtaining at least a first suitable anti-MFAP5 antibody-encoding nucleic acid molecule or segment from a suitable anti-MFAP5 antibody-producing cell, preferably a hybridoma; and (b) expressing the nucleic acid molecule or segment in a recombinant host cell to obtain a recombinant anti-MFAP5 monoclonal antibody in accordance with the present disclosure.

The invention also provides in vitro diagnostic kits comprising at least a first composition or pharmaceutical composition comprising a biologically effective amount of at least one diagnostic agent that is operatively associated with at least a first anti-MFAP5 antibody, optionally one that binds to substantially the same epitope as the monoclonal antibody 130A (ATCC X), or an antigen-binding fragment thereof.

The invention still further provides combined kits in which the diagnostic agent is intended for use outside the body, preferably in connection with a test conducted on a biological sample obtained from an animal or patient. As such, the invention provides kits comprising, generally in at least two distinct containers, at least a first composition, pharmaceutical composition or medicinal cocktail comprising a biologically effective amount of at least a first anti-MFAP5 antibody, optionally one that binds to substantially the same epitope as the monoclonal antibody 130A (ATCC X), or an antigen-binding fragment or immunoconjugate of such an anti-MFAP5 antibody; and a biologically effective amount of at least one diagnostic agent, component or system for in vitro use.

The "diagnostic agent, component or system for in vitro use" will be any diagnostic agent or combination of agents that allow the diagnosis of one or more diseases that have an angiogenic component. The in vitro diagnostics thus include those suitable for use in generating diagnostic or prognostic information in relation to a disease or disorder as disclosed in any one of U.S. Pat. Nos. 5,712,291, 5,753,230, 5,972,922, and 5,639,757, and PCT Intl. Pat. Appl. Publ. No's. WO 98/45331 and WO 98/16551, each of which is specifically incorporated herein in its entirety by express reference thereto.

"Detectable or reporter agents" directly detectable in vitro include those such as radiolabels and reporter agents detectable by immunofluorescence.

In certain other embodiments, the antibodies and immunoconjugates of the invention may be combined with one or more diagnostic agents, typically diagnostic agents for use in connection with angiogenic diseases. A range of diagnostic compositions, kits and methods are thus included within the invention.

In terms of cancer diagnosis and treatment, the diagnostic and imaging compositions, kits and methods of the present invention include in vivo and in vitro diagnostics. For example, a tumor may be imaged using a diagnostically effective amount of a tumor diagnostic component that comprises at least a first binding region that binds to an accessible component of a tumor cell, tumor vasculature or tumor stroma, operatively attached to an in vivo diagnostic imaging agent.

The tumor imaging is preferably conducted to provide an image of the stroma and/or vasculature of a vascularized tumor using a diagnostic component that comprises at least a first binding region that binds to an accessible component of tumor vasculature or tumor stroma. Any suitable binding region or antibody may be employed, such as those described above in terms of the therapeutic constructs. Certain advantages will be provided by using a detectably-labeled anti-MFAP5 antibody or a detectably-labeled 130A-based antibody construct, wherein the image formed will be predictive the binding sites of the therapeutic to be used.

Detectably-labeled in vivo tumor diagnostics, whether anti-MFAP5 antibody or 130A antibody-based or not, may comprise an X-ray detectable compound, such as bismuth (III), gold (III), lanthanum (III) or lead (II); a radioactive ion, such as copper$^{67}$, gallium$^{67}$, gallium$^{68}$, indium$^{111}$, indium$^{13}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

Pre-imaging before tumor treatment may be carried out by:

(a) administering to the animal or patient a diagnostically effective amount of a pharmaceutical composition comprising a diagnostic agent operatively attached to at least a first binding region that binds to an accessible component of a tumor cell, tumor vasculature (preferably) or tumor stroma (preferably), including diagnostic agents operatively attached to anti-MFAP5 antibody or 130A-based antibody constructs; and (b) subsequently detecting the detectably-labeled first binding region (or anti-MFAP5 antibody or 130A-based antibody) bound to the tumor cells, tumor blood vessels (preferably) or tumor stroma (preferably); thereby obtaining an image of the tumor, tumor vasculature and/or tumor stroma.

BRIEF DESCRIPTION OF THE DRAWINGS

The following drawings form part of the present specification and are included to demonstrate certain aspects of the present invention. For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The invention may be better understood by reference to the following description taken in conjunction with the accompanying drawings, in which like reference numerals identify like elements, and in which:

FIG. 7A, FIG. 7B, FIG. 7C, FIG. 7D, FIG. 7E, FIG. 7F, and FIG. 7G show development and characterization of anti-MFAP5 monoclonal antibodies. FIG. 7A shows a flow diagram illustrating the overall workflow of therapeutic anti-MFAP5 monoclonal antibody development. FIG. 7B shows Western blot analyses that were performed to identify antibody clones with high binding affinity and specificity to MFAP5. FIG. 7C shows Epitope mapping results showing that whereas clones 64A and 117B recognized human MFAP5, clone 130A recognized both human and murine MFAP5 protein sequences. FIG. 7D shows Western blot analyses validating the specificity of two clones of mouse monoclonal antibodies against human MFAP5 (64A and 117B) and one clone of an antibody against both human and mouse MFAP5 (130A). FIG. 7E illustrates kinetic assay results that showed the dissociation constant (Ka) of clone 130A for human and mouse MFAP5 protein were 1.93 nM and 2.51 nM respectively, suggesting that clone 130A has high binding affinity to both human MFAP5 and mouse Mfap5 protein. FIG. 7F shows a titration curve for the 130A antibody generated by ELISA and recombinant MFAP5 protein at various concentrations. FIG. 7G shows ELISA results demonstrating that serum samples obtained from high grade serous ovarian cancer patients had significantly higher levels of MFAP5 than the healthy individuals did;

FIG. 8A and FIG. 8B: Motility assays performed on $\alpha_v\beta_3$-expressing human ovarian cancer cell lines A224 and ALST co-cultured with MFAP5-overexpressing fibroblasts or control fibroblasts in the presence of human IgG or anti-human MFAP5 antibody clones 64A, 117B and 130A demonstrated that the anti-MFAP5 monoclonal antibodies markedly inhibited MFAP5-stimulated ovarian cancer cell motility. FIG. 8C and FIG. 8D: Human microvascular endothelial cell lines hMEC-1 and TIME co-cultured with MFAP5-overexpressing fibroblasts or control fibroblasts in the presence of human IgG or anti-human MFAP5 antibody clones 64A and 117B demonstrated that the anti-MFAP5 monoclonal antibodies markedly inhibited MFAP5-stimulated microvascular endothelial cell motility. FIG. 8E shows motility assays on SVEC4-10 mouse endothelial cells cultured in media supplemented with recombinant mouse mfap5 or PBS demonstrated that antibody clone 130A markedly inhibited mfap5-induced mouse endothelial cell motility. FIG. 8F shows motility assays demonstrated that MFAP5-induced PANC1 human pancreatic cancer cell motility was markedly suppressed by the presence of anti-MFAP5 monoclonal antibody clones 64A, 117B and 130A. FIG. 8G shows that for the PDX cell line, PATC53, the motility promoting effect of MFAP5 was abrogated in the presence of the anti-MFAP5-blocking antibody, but not by the control IgG;

FIG. 9A shows complete blood counts (CBCs) for anti-MFAP5 antibody clone 64A-, 117b-, or 130A-treated mice and PBS-treated control mice revealing no observable adverse effects from anti-MFAP5 antibody administration. FIG. 9B summarizes chemistry test results generated from serum samples collected from anti-MFAP5 antibody clone 64A-, 117b-, and 130A-treated mice compared with PBS-treated control mice revealing no significant toxic effects of the antibody-based treatment to the animals' kidneys and livers. For scatter plots, upper and lower bars indicate the interquartile range of the records, and the middle line indicates the median measurements. FIG. 9C shows hematoxylin- and eosin-stained images of spleen, kidney, and liver tissue samples obtained from mice given treatment with antibody clone 64A, 117B, or 130A compared with those obtained from PBS-treated control animals. No significant toxic effects of antibody-based treatment were observed. Representative images were selected from three individual replicates. (Bar=100 μm);

FIG. 10A is a schematic of the procedures used to evaluate the effects of treatment with an anti-mfap5 antibody on ovarian cancer progression in vivo. FIG. 10B shows the bioluminescence measurement of ovarian tumor progression in the control IgG and anti-MFAP5 monoclonal antibody treatment groups of mice showed significantly lower luciferase activity in the anti-MFAP5 antibody-treated groups than in the control group (P=0.004). In the box plot, the boxes represent the interquartile range of the records, and the lines across the boxes indicate the median luminescence signals. The whiskers indicate the highest and lowest values among the records that are no more than 1.5 times greater than the interquartile range. FIG. 10C shows that after necropsy, the tumor weight was recorded for each animal, with significantly reduced tumor dry weights being detected in animals treated with an anti-MFAP5 antibody (P=0.0086). FIG. 10D shows a schematic of the procedures used to evaluate the effects of treatment with an anti-MFAP5 antibody on pancreatic cancer progression in vivo. FIG. 10E summarizes the bioluminescence measurement of pancreatic tumor progression in the control IgG and anti-MFAP5 monoclonal antibody treatment groups of mice showing significantly lower luciferase activity in the anti-mfap5 antibody-treated groups than in the control group (P=0.011). In the box plot, the boxes represent the interquartile range of the records, and the lines across the boxes indicate the median luminescence signals. The whiskers indicate the highest and lowest values among the records that are no more than 1.5 times greater than the interquartile range. FIG. 10F: After necropsy, the tumor weight was recorded for each animal, significantly reduced tumor weights were detected in animal treatment with an anti-MFAP5 antibody (P=0.0011) (see FIG. 10G);

FIG. 11A: Dosing schedule for combination therapy with an anti-MFAP5 antibody and paclitaxel in an ovarian cancer animal model. FIG. 11B: Tumor progression was quantified in terms of both tumor weight and ex vivo bioluminescence. Experimental results indicated that the combination treatment with the anti-mfap5 antibody and paclitaxel resulted in markedly smaller tumors than did single-agent treatment with paclitaxel. FIG. 11C: Confocal microscopic images demonstrating lower $CD34^+$ microvessel density (red) and FITC-dextran (green) signals around tumor microvessels in anti-MFAP5 antibody-treated mice than in IgG-treated mice, suggesting that treatment with the anti-mfap5 antibody reduced tumor angiogenesis and intratumoral microvessel leakiness in vivo. Red, CD34; green, dextran; blue, nuclei; scale bar, 100 μm. FIG. 11D: Fluorescent microscopic images showing significantly greater delivery of Oregon Green 488-conjugated paclitaxel (green) to tumors despite lower intratumoral MVD in mice given an anti-mfap5 antibody than in control mice given IgG. These results suggested that the anti-mfap5 antibody facilitated systematic delivery of paclitaxel to ovarian tumors. Red, CD34; green, paclitaxel; blue, nuclei; bar, 5 μm. FIG. 11E: Stromal expression heatmap of fibrosis related genes showing two group of ovarian cancer patients expressing high and low levels of fibrotic genes. Ovarian cancer patients express high level of fibrotic genes had a median survival duration of 19 months (95% CI=12.3-25.7 months), whereas patients express low level of fibrotic genes had a median survival duration of 33 months (95% CI=22.0-44.0 months) (P=0.017). FIG. 11F: Picrosirius red staining of collagen on tumor tissues obtained from mice treated with 130A antibody or the control IgG showed that tumors in mice treated with 130A had significantly lower collagen coverage and intensity in cancer associated stromal tissue than in those treated with IgG. FIG. 11G shows the pathway analysis of 176 genes that demonstrated significant positive correlation with MFAP5 expression in CAFs (Pearson correlation coefficient>0.7, Pearson correlation P values and Benjamini-Hochberg adjusted P values<0.05) suggested a collagen enriched key signaling network. FIG. 11H: qRT-PCR analysis demonstrated that recombinant MFAP5 protein induces COL1A1 and COL11A1 mRNA expression in ovarian fibroblasts, which was abrogated in the presence of 130A anti-MFAP5 antibody;

FIG. 14A: Immunolocalization of stromal MFAP5 on tumor tissue samples and the corresponding normal adjacent tissue samples from 64 PDAC patients showed that while the majority of normal adjacent tissue is negative for MFAP5 expression, expression levels of MFAP5 was significantly higher in pancreatic CAFs (P<0.001). FIG. 14B: Kaplan-Meier survival analysis and log-rank test showed that high stromal MFAP5 expression in patients with PDAC is significantly associated to the reduction of overall survival duration. Using median expression level as the cut off, pancreatic cancer patients expressing high level of stromal MFAP5 had a median survival duration of 8 months (95% CI=6.0-10.0 months), whereas patients expressing low level of stromal MFAP5 had a median survival duration of 31 months (95% CI=11.3-50.8 months) (N=91, P=0.001);

BRIEF DESCRIPTION OF THE AMINO ACID AND NUCLEIC ACID SEQUENCES

SEQ ID NO: 1 is the amino acid sequence of the human MFAP5 polypeptide (*Homo sapiens*, GenBank accession: AAH05901.1) for use in accordance with one aspect of the present disclosure;

1 MSLLGPKVLL FLAAFIITSD WIPLGVNSOR GDDVTQATPE TFTEDPNLVN DPATDETVLA

61 VLADIAPSTD DLASLSEKNT TAECWDEKFT CTRLYSVHRP VKQCIHQLCF TSLRRMYIVN

121 KEICSRLVCK EHEAMKDELC RQMAGLPPRR LRRSNYFRLP PCENVDLORP NGL

[

SEQ ID NO: 2 is the amino acid sequence of the murine Mfap5 polypeptide (*Mus musculus*, GeneBank accession: AAH25131.1) for use in accordance with one aspect of the present disclosure;

1 MLFLGQKALL LVLAVSIPSD WLPLGVSGQR GDDVPETFTD DPNLVNDPST DDTALADITP

61 STDDLADDKN ATAECRDEKF ACTRLYSVHR PVRQCVHQSC FTSLRRMYII NNEICSRLVC

121 KEHEAMKDEL CRQMAGLPPR RLRRSNYFRL PPCENMNLQR PDGL

SEQ ID NO:3 is an exemplary MFAP5-specific peptide epitope having the amino acid sequence "DETVLAVLA" for use in accordance with one aspect of the present disclosure.

SEQ ID NO:4 is an exemplary consensus peptide having the amino acid sequence "LCRQMAGLPPRR" that is common to both the human and the marine MFAP5 proteins for use in accordance with one aspect of the present disclosure.

Figure 12A:
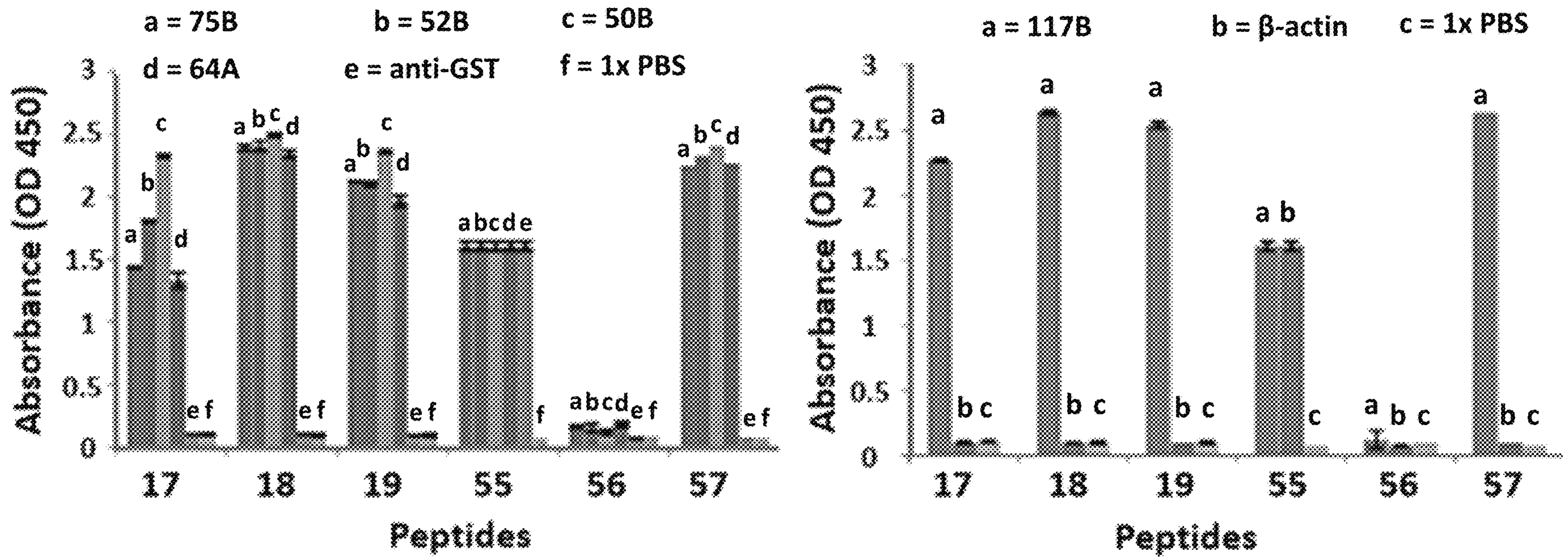
FIG. 12A, FIG. 12B, FIG. 12C, and FIG. 12D show characterization of anti-MFAP5 monoclonal antibodies. ELISA based epitope mapping result showed (FIG. 12A) that anti-MFAP5 mAb clone 64A and 117B recognized the same human MFAP5 protein sequence (DETVLAVLA) (SEQ ID NO:3), while clone 130A (FIG. 12B) was specific to a consensus peptide sequence (LCRQMAGLPPRR) (SEQ ID NO:4) common to both human and murine MFAP5 proteins. Kinetic assays showed that the dissociation constant ($K_d$) of clone 64A (FIG. 12C) and 117B (FIG. 12D) for human MFAP5 protein were 0.48 nM and 6.7 nM, respectively, which suggested high binding affinity to the human MFAP5 protein.

SEQ ID NO:5 is an exemplary peptide having the amino acid sequence "VNDPATDETVLAVLA" as shown in FIG. 12A for use in accordance with one aspect of the present disclosure.

SEQ ID NO:6 is an exemplary consensus peptide having the amino acid sequence "PATDETVLAVLADIA" as shown in FIG. 12A for use in accordance with one aspect of the present disclosure.

SEQ ID NO:7 is an exemplary consensus peptide having the amino acid sequence "DETVLAVLADIAPST" as shown in FIG. 12A for use in accordance with one aspect of the present disclosure.

Figure 12B:
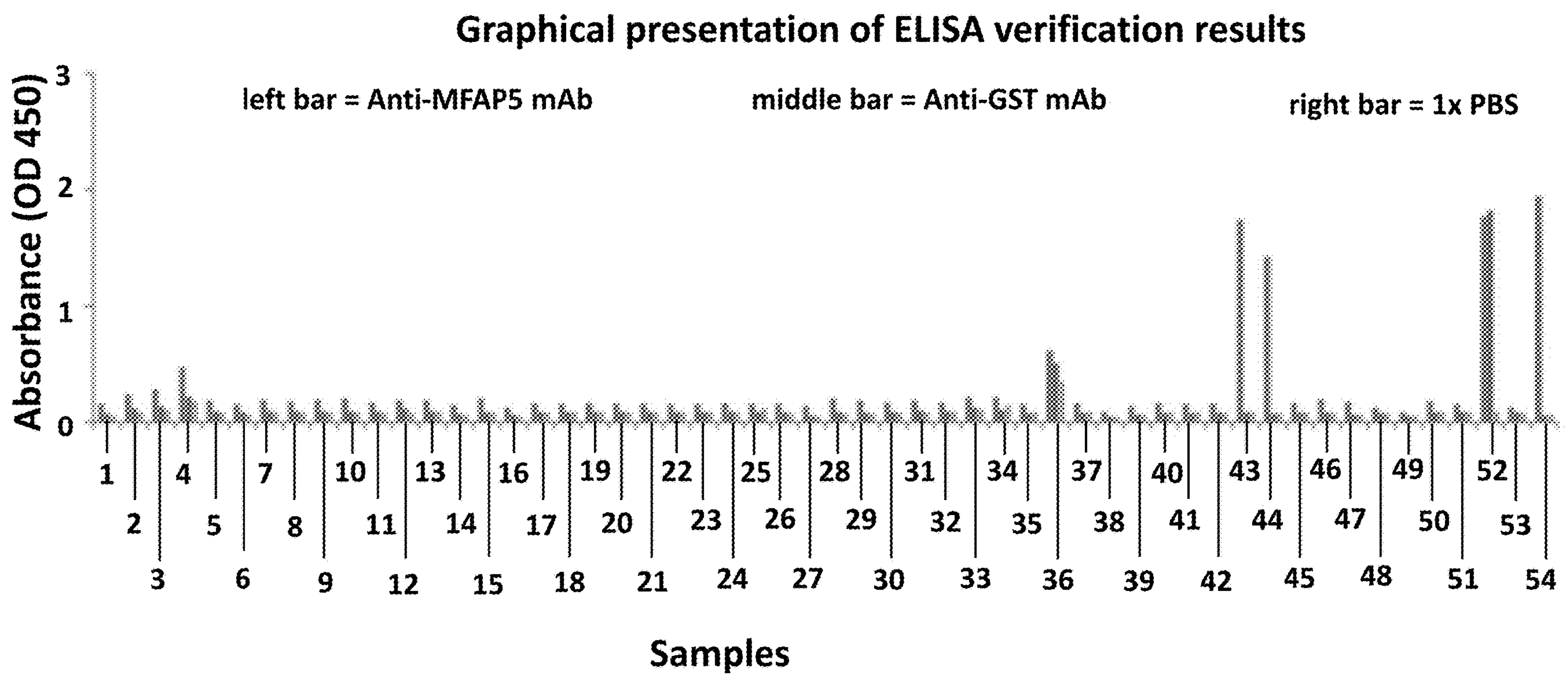

SEQ ID NO:8 is an exemplary consensus peptide having the amino acid sequence "KDELSRQMGLPPRR" as shown in FIG. 12B for use in accordance with one aspect of the present disclosure.

SEQ ID NO:9 is an exemplary consensus peptide having the amino acid sequence "LSRQMAGLPPRRLRR" as shown in FIG. 12B for use in accordance with one aspect of the present disclosure.

SEQ ID NO: 10 is an exemplary humanized antibody sequence shown in the format of 'Leader sequence-VH/VL-hIgG1CH/hIgKCL' for grafted VHI:

*MGWSCIILFLVATATGVHS*QVQLVQSGAEVKKPGASVKVSCKASGYSFT

GYFMNWVRQAPGQRLEWMGRINPYNGDTFYNQKFKGRVTITRDTSASTAY

MELSSLRSEDTAVYYCARGNHYTMDYWGQGTLVTVSSASTKGPSVFPLAPSS

KSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

SEQ ID NO: 11 is an exemplary humanized antibody sequence shown in the format of 'Leader sequence-VH/VL-hIgG1CH/hIgKCL' for AHF00208-VH:

*MGWSCIILFLVATATGVHS*QVQLVQSGAEVKKPGASVKVSCKASGYSFT

GYFMNWVRQAPGQSLEWMGRINPYNGDTFYNQKFKGRVTITRDTSASTAH

MELSSLRSEDTAVYYCARGNHYTMDYWGQGTLVTVSSASTKGPSVFPLAPSS

KSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQ

-continued

PREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

SEQ ID NO: 12 is an exemplary humanized antibody sequence shown in the format of 'Leader sequence-VH/VL-hIgG1CH/hIgKCL' for AHF00217-VH:
*MGWSCIILFLVATATG*VHSQVQLVQSGAEVKKPGASVKVSCKASGYSF

TGYFMNWVRQAPGQRLEWMGRINPYNGDTFYNQKFKGRVTITRDTSASTAH

MELSSLRSEDTAVYYCARGNHYTMDYWGQGTLVTVSSASTKGPSVFPLAPSS

KSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

SEQ ID NO: 13 is an exemplary humanized antibody sequence shown in the format of 'Leader sequence-VH/VL-hIgG1CH/hIgKCL' for AHF00220-VH:
*MGWSCIILFLVATATGVHS*QVQLVQSGAEVKKPGASVKVSCKASGYSFTG

YFMNWVRQAPGQSLEWIGRINPYNGDTFYNQKFKGRVTITRDTSASTAYMELSS

LRSEDTAVYYCARGNHYTMDYWGQGTLVTVSSASTKGPSVFPLAPSSKSTSGGT

AALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSKLTVD

KSRWQQGNVFSCSVMHEALHNHYTQKSLSLSPGK

SEQ ID NO: 14 is an exemplary humanized antibody sequence shown in the format of 'Leader sequence-VH/VL-hIgG1CH/hIgKCL' for Light chain Grafted-VL1 (AHF00208-VL = AHF00220-VL):
*MGWSCIILFLVATATGVHS*DIQMTQSPSSLSASVGDRVTITCKASQDINS

YLSWYQQKPGKAPKLLIYRANRLVDGVPSRFSGSGSGTDFTFTISSLQPEDIAT

YYCLQYDEFPLTFGGGTKLEIKRTVAAPSVFIFPPSDEQLKSGTASVVCLLNNF

YPREAKVQWKVDNALQSGNSQESVTEQDSKDSTYSLSSTLTLSKADYEKHK

VYACEVTHQGLSSPVTKSFNRGEC

SEQ ID NO: 15 is an exemplary humanized antibody sequence shown in the format of 'Leader sequence-VH/VL-hIgG1CH/hIgKCL' for AHF00217-VL
*MGWSCIILFLVATATGVHS*DIQMTQSPSSLSASVGDRVTITCKASQDINS

YLSWYQQKPGKAPKLLIYRANRLVDGVPSRFSGSGSGTDYTFTISSLQPEDIAT

YYCLQYDEFPLTFGGGTKLEIKRTVAAPSVFIFPPSDEQLKSGTASVVCLLNNE

YPREAKVOWKVDNALQSGNSQESVTEQDSKDSTYSLSSTLTLSKADYEKHK

VYACEVTHQGLSSPVTKSFNRGEC

SEQ ID NO: 16 is an exemplary nucleotide sequence that encodes the heavy chain of the humanized antibody sequence identified above as Grafted Ab-VH:
ATGGGCTGGAGCTGGATCCTGCTGTTCCTCCTGAGCGTGACAGCAGGAGT

GCACAGCCAGGTGCAGCTGGTGCAGTCCGGAGCAGAGGTGAAGAAGCCA

GGAGCCTCTGTGAAGGTGAGCTGCAAGGCCAGCGGCTACTCCTTCACCGG

CTACTTCATGAACTGGGTGAGGCAGGCACCAGGACAGCGCCTGGAGTGGA

TGGGCCGGATCAACCCTTACAATGGCGACACATTCTATAATCAGAAGTTT

-continued

AAGGGCCGGGTGACCATCACAAGAGATACCTCCGCCTCTACAGCCTACAT

GGAGCTGAGCTCCCTGAGGTCTGAGGACACCGCCGTGTACTATTGTGCCC

GGGGCAACCACTACACAATGGATTATTGGGGCCAGGGCACCCTGGTGACA

GTGTCTAGCGCTAGCACCAAGGGCCCATCGGTCTTCCCCCTGGCACCCTCC

TCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCA

GCGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTAC

ATCTGCAACGTGAATCACAAGCCCAGCAACACCAAGGTGGACAAGAAAG

TTGAGCCCAAATCTTGTGACAAAACTCACACATGCCCACCGTGCCCAGCA

CCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGA

CGTGAGCCACGAAGACCCTGAGGTCAAGTTCAACTGGTACGTGGACGGCG

TGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTG

CTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGC

TCTGCACAACCACTACACGCAGAAGAGCCTCTCCCTGTCTCCGGGTAAAT

GA

SEQ ID NO: 17 is an exemplary nucleotide sequence that encodes the heavy chain of the humanized antibody sequence identified above as >AHF00208-VH:

ATGGGCTGGAGCTGGATCCTGCTGTTCCTCCTGAGCGTGACAGCAGGAGT

GCACAGCCAGGTGCAGCTGGTGCAGTCCGGAGCAGAGGTGAAGAAGCCA

GGAGCCTCTGTGAAGGTGAGCTGCAAGGCCAGCGGCTACTCCTTCACCGG

CTACTTCATGAACTGGGTGCGGCAGGCACCAGGACAGTCTCTGGAGTGGA

TGGGCAGGATCAACCCTTACAATGGCGACACATTCTATAATCAGAAGTTT

AAGGGCCGGGTGACCATCACAAGAGATACCTCCGCCTCTACAGCCCACAT

GGAGCTGAGCTCCCTGAGGAGCGAGGACACCGCCGTGTACTATTGTGCCC

GCGGCAACCACTACACAATGGATTATTGGGGCCAGGGCACCCTGGTGACA

GTGTCTAGCGCTAGCACCAAGGGCCCATCGGTCTTCCCCCTGGCACCCTCC

TCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCA

GCGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTAC

ATCTGCAACGTGAATCACAAGCCCAGCAACACCAAGGTGGACAAGAAAG

TTGAGCCCAAATCTTGTGACAAAACTCACACATGCCCACCGTGCCCAGCA

CCTGAACTCCTGGGGGGACCGTCAGTCTTCCTCTTCCCCCCAAAACCCAAG

-continued

GACACCCTCATGATCTCCCGGACCCCTGAGGTCACATGCGTGGTGGTGGA

CGTGAGCCACGAAGACCCTGAGGTCAAGTTCAACTGGTACGTGGACGGCG

TGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTG

CTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGC

TCTGCACAACCACTACACGCAGAAGAGCCTCTCCCTGTCTCCGGGTAAAT

GA

SEQ ID NO: 18 is an exemplary nucleotide sequence that encodes the heavy chain of the humanized antibody sequence identified above as AHF00217-VH:

ATGGGCTGGAGCTGGATCCTGCTGTTCCTCCTGAGCGTGACAGCAGGAGT

GCACAGCCAGGTGCAGCTGGTGCAGTCCGGAGCAGAGGTGAAGAAGCCA

GGAGCCTCTGTGAAGGTGAGCTGCAAGGCCAGCGGCTACTCCTTCACCGG

CTACTTCATGAACTGGGTGAGGCAGGCACCAGGACAGCGCCTGGAGTGGA

TGGGCCGGATCAACCCTTACAATGGCGACACATTCTATAATCAGAAGTTT

AAGGGCCGGGTGACCATCACAAGAGATACCTCCGCCTCTACAGCCCACAT

GGAGCTGAGCTCCCTGAGGTCTGAGGACACCGCCGTGTACTATTGTGCCC

GGGGCAACCACTACACAATGGATTATTGGGGCCAGGGCACCCTGGTGACA

GTGTCTAGCGCTAGCACCAAGGGCCCATCGGTCTTCCCCCTGGCACCCTCC

TCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCA

GCGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTAC

ATCTGCAACGTGAATCACAAGCCCAGCAACACCAAGGTGGACAAGAAAG

TTGAGCCCAAATCTTGTGACAAAACTCACACATGCCCACCGTGCCCAGCA

CCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGA

CGTGAGCCACGAAGACCCTGAGGTCAAGTTCAACTGGTACGTGGACGGCG

TGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTG

CTGGACTCCGACGGCTCCTTCTTCCTCTACAGCAAGCTCACCGTGGACAAG

-continued

AGCAGGTGGCAGCAGGGGAACGTCTTCTCATGCTCCGTGATGCATGAGGC

TCTGCACAACCACTACACGCAGAAGAGCCTCTCCCTGTCTCCGGGTAAAT

GA.

SEQ ID NO: 19 is an exemplary nucleotide sequence that encodes the heavy chain of the humanized antibody sequence identified above as AHF00220-VH:

ATGGGCTGGAGCTGGATCCTGCTGTTCCTCCTGAGCGTGACAGCAGGAGT

GCACAGCCAGGTGCAGCTGGTGCAGTCCGGAGCAGAGGTGAAGAAGCCA

GGAGCCTCTGTGAAGGTGAGCTGCAAGGCCAGCGGCTACTCCTTCACCGG

CTACTTCATGAACTGGGTGCGGCAGGCACCAGGACAGTCTCTGGAGTGGA

TCGGCAGGATCAACCCTTACAATGGCGACACATTCTATAATCAGAAGTTT

AAGGGCCGGGTGACCATCACAAGAGATACCTCCGCCTCTACAGCCTACAT

GGAGCTGAGCTCCCTGAGGAGCGAGGACACCGCCGTGTACTATTGTGCCC

GCGGCAACCACTACACAATGGATTATTGGGGCCAGGGCACCCTGGTGACA

GTGTCTAGCGCTAGCACCAAGGGCCCATCGGTCTTCCCCCTGGCACCCTCC

TCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCA

GCGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTAC

ATCTGCAACGTGAATCACAAGCCCAGCAACACCAAGGTGGACAAGAAAG

TTGAGCCCAAATCTTGTGACAAAACTCACACATGCCCACCGTGCCCAGCA

CCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGA

CGTGAGCCACGAAGACCCTGAGGTCAAGTTCAACTGGTACGTGGACGGCG

TGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTG

CTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGC

TCTGCACAACCACTACACGCAGAAGAGCCTCTCCCTGTCTCCGGGTAAAT

GA

SEQ ID NO: 20 is the DNA sequence of the Light chain of Grafted Ab-VL (AHF00208-VL = AHF00220-VL) as referred to above:

ATGGGCTGGAGCTGGATCCTGCTGTTCCTCCTGAGCGTGACAGCAGGAGT

GCACAGCGACATCCAGATGACCCAGTCTCCTAGCTCCCTGTCCGCCTCTGT

GGGCGACAGGGTGACCATCACATGCAAGGCCAGCCAGGATATCAACAGC

TACCTGTCCTGGTATCAGCAGAAGCCCGGCAAGGCCCCTAAGCTGCTGAT

CTACCGGGCCAATAGACTGGTGGACGGAGTGCCATCCCGGTTCAGCGGAT

CCGGCTCTGGCACCGATTTCACCTTTACAATCTCTAGCCTGCAGCCAGAGG

ACATCGCCACATACTATTGTCTGCAGTATGATGAGTTCCCCCTGACCTTTG

-continued

GCGGCGGCACAAAGCTGGAGATCAAGCGAACGGTGGCTGCACCATCTGTC

TTCATCTTCCCGCCATCTGATGAGCAGTTGAAATCTGGAACTGCCTCTGTT

GTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGC

AGGACAGCAAGGACAGCACCTACAGCCTCAGCAGCACCCTGACGCTGAG

CAAAGCAGACTACGAGAAACACAAAGTCTACGCCTGCGAAGTCACCCATC

AGGGCCTGAGCTCGCCCGTCACAAAGAGCTTCAACAGGGGAGAGTGTTAG

SEQ ID NO: 21 is the DNA sequence of the AHF00217-VL as referred to above:
ATGGGCTGGAGCTGGATCCTGCTGTTCCTCCTGAGCGTGACAGCAGGAGT

GCACAGCGACATCCAGATGACCCAGTCTCCTAGCTCCCTGTCCGCCTCTGT

GGGCGACAGGGTGACCATCACATGCAAGGCCAGCCAGGATATCAACAGC

TACCTGTCCTGGTATCAGCAGAAGCCCGGCAAGGCCCCTAAGCTGCTGAT

CTACCGGGCCAATAGACTGGTGGACGGAGTGCCATCCCGGTTCAGCGGAT

CCGGCTCTGGCACCGATTACACCTTTACAATCTCTAGCCTGCAGCCAGAGG

ACATCGCCACATACTATTGTCTGCAGTATGATGAGTTCCCCCTGACCTTTG

GCGGCGGCACAAAGCTGGAGATCAAGCGAACGGTGGCTGCACCATCTGTC

TTCATCTTCCCGCCATCTGATGAGCAGTTGAAATCTGGAACTGCCTCTGTT

GTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGC

AGGACAGCAAGGACAGCACCTACAGCCTCAGCAGCACCCTGACGCTGAG

CAAAGCAGACTACGAGAAACACAAAGTCTACGCCTGCGAAGTCACCCATC

AGGGCCTGAGCTCGCCCGTCACAAAGAGCTTCAACAGGGGAGAGTGTTAG

The sequence of the heavy chain variable region of the grafted VHI of SEQ ID NO: 10 is SEQ ID NO:22. The sequence of the heavy chain variable region of the AHF00208-VH of SEQ ID NO: 11 is SEQ ID NO:23. The sequence of the heavy chain variable region of the AHF00217-VH of SEQ ID NO: 12 is SEQ ID NO:24. The sequence of the heavy chain variable region of the AHF00220-VH of SEQ ID NO: 13 is SEQ ID NO:25. The sequence of the light chain variable region of the AHF00208-VH/AHF00220-VH of SEQ ID NO: 14 is SEQ ID NO:26. The sequence of the light chain variable region of the AHF00217-VL of SEQ ID NO: 15 is SEQ ID NO:27.

SEQ ID NO: 16 is an exemplary nucleotide sequence that encodes the heavy chain of the humanized antibody sequence identified above as Grafted Ab-VH:
ATGGGCTGGAGCTGGATCCTGCTGTTCCTCCTGAGCGTGACAGCAGGAGT

GCACAGCCAGGTGCAGCTGGTGCAGTCCGGAGCAGAGGTGAAGAAGCCA

GGAGCCTCTGTGAAGGTGAGCTGCAAGGCCAGCGGCTACTCCTTCACCGG

CTACTTCATGAACTGGGTGAGGCAGGCACCAGGACAGCGCCTGGAGTGGA

TGGGCCGGATCAACCCTTACAATGGCGACACATTCTATAATCAGAAGTTT

AAGGGCCGGGTGACCATCACAAGAGATACCTCCGCCTCTACAGCCTACAT

GGAGCTGAGCTCCCTGAGGTCTGAGGACACCGCCGTGTACTATTGTGCCC

GGGGCAACCACTACACAATGGATTATTGGGGCCAGGGCACCCTGGTGACA

-continued

GTGTCTAGCGCTAGCACCAAGGGCCCATCGGTCTTCCCCCTGGCACCCTC

CTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACC

AGCGGCGTGCACACCTTCCCGGCTGTCCTACAGTCCTCAGGACTCTACTC

CCTCAGCAGCGTGGTGACCGTGCCCTCCAGCAGCTTGGGCACCCAGACCT

ACATCTGCAACGTGAATCACAAGCCCAGCAACACCAAGGTGGACAAGAAA

GTTGAGCCCAAATCTTGTGACAAAACTCACACATGCCCACCGTGCCCAGC

ACCTGAACTCCTGGGGGGACCGTCAGTCTTCCTCTTCCCCCCAAAACCCA

AGGACACCCTCATGATCTCCCGGACCCCTGAGGTCACATGCGTGGTGGTG

GACGTGAGCCACGAAGACCCTGAGGTCAAGTTCAACTGGTACGTGGACGG

CGTGGAGGTGCATAATGCCAAGACAAAGCCGCGGGAGGAGCAGTACAACA

GCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCC

CATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTGC

-continued

TGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGC

TCTGCACAACCACTACACGCAGAAGAGCCTCTCCCTGTCTCCGGGTAAAT

GA.

SEQ ID NO: 17 is an exemplary nucleotide sequence that encodes the heavy chain of the humanized antibody sequence identified above as >AHF00208-VH:

ATGGGCTGGAGCTGGATCCTGCTGTTCCTCCTGAGCGTGACAGCAGGAGT

GCACAGCCAGGTGCAGCTGGTGCAGTCCGGAGCAGAGGTGAAGAAGCCA

GGAGCCTCTGTGAAGGTGAGCTGCAAGGCCAGCGGCTACTCCTTCACCGG

CTACTTCATGAACTGGGTGCGGCAGGCACCAGGACAGTCTCTGGAGTGGA

TGGGCAGGATCAACCCTTACAATGGCGACACATTCTATAATCAGAAGTTT

AAGGGCCGGGTGACCATCACAAGAGATACCTCCGCCTCTACAGCCCACAT

GGAGCTGAGCTCCCTGAGGAGCGAGGACACCGCCGTGTACTATTGTGCCC

GCGGCAACCACTACACAATGGATTATTGGGGCCAGGGCACCCTGGTGACA

GTGTCTAGCGCTAGCACCAAGGGCCCATCGGTCTTCCCCCTGGCACCCTC

CTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACC

AGCGGCGTGCACACCTTCCCGGCTGTCCTACAGTCCTCAGGACTCTACTC

CCTCAGCAGCGTGGTGACCGTGCCCTCCAGCAGCTTGGGCACCCAGACCT

ACATCTGCAACGTGAATCACAAGCCCAGCAACACCAAGGTGGACAAGAAA

GTTGAGCCCAAATCTTGTGACAAAACTCACACATGCCCACCGTGCCCAGC

ACCTGAACTCCTGGGGGGACCGTCAGTCTTCCTCTTCCCCCCAAAACCCA

AGGACACCCTCATGATCTCCCGGACCCCTGAGGTCACATGCGTGGTGGTG

GACGTGAGCCACGAAGACCCTGAGGTCAAGTTCAACTGGTACGTGGACGG

CGTGGAGGTGCATAATGCCAAGACAAAGCCGCGGGAGGAGCAGTACAACA

GCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCC

CATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTG

GCTGGACTCCGACGGCTCCTTCTTCCTCTACAGCAAGCTCACCGTGGACA

AAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

TGA.

SEQ ID NO: 18 is an exemplary nucleotide sequence that encodes the heavy chain of the humanized antibody sequence identified above as AHF00217-VH:

ATGGGCTGGAGCTGGATCCTGCTGTTCCTCCTGAGCGTGACAGCAGGAGT

GCACAGCCAGGTGCAGCTGGTGCAGTCCGGAGCAGAGGTGAAGAAGCCA

GGAGCCTCTGTGAAGGTGAGCTGCAAGGCCAGCGGCTACTCCTTCACCGG

CTACTTCATGAACTGGGTGAGGCAGGCACCAGGACAGCGCCTGGAGTGGA

-continued

TGGGCCGGATCAACCCTTACAATGGCGACACATTCTATAATCAGAAGTTT

AAGGGCCGGGTGACCATCACAAGAGATACCTCCGCCTCTACAGCCCACAT

GGAGCTGAGCTCCCTGAGGTCTGAGGACACCGCCGTGTACTATTGTGCCC

GGGGCAACCACTACACAATGGATTATTGGGGCCAGGGCACCCTGGTGACA

GTGTCTAGCGCTAGCACCAAGGGCCCATCGGTCTTCCCCCTGGCACCCTC

CTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACC

AGCGGCGTGCACACCTTCCCGGCTGTCCTACAGTCCTCAGGACTCTACTC

CCTCAGCAGCGTGGTGACCGTGCCCTCCAGCAGCTTGGGCACCCAGACCT

ACATCTGCAACGTGAATCACAAGCCCAGCAACACCAAGGTGGACAAGAAA

GTTGAGCCCAAATCTTGTGACAAAACTCACACATGCCCACCGTGCCCAGC

ACCTGAACTCCTGGGGGGACCGTCAGTCTTCCTCTTCCCCCCAAAACCCA

AGGACACCCTCATGATCTCCCGGACCCCTGAGGTCACATGCGTGGTGGTG

GACGTGAGCCACGAAGACCCTGAGGTCAAGTTCAACTGGTACGTGGACGG

CGTGGAGGTGCATAATGCCAAGACAAAGCCGCGGGAGGAGCAGTACAACA

GCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCC

CATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTG

CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

TGA.

SEQ ID NO: 19 is an exemplary nucleotide sequence that encodes the heavy chain of the humanized antibody sequence identified above as AHF00220-VH:

ATGGGCTGGAGCTGGATCCTGCTGTTCCTCCTGAGCGTGACAGCAGGAGT

GCACAGCCAGGTGCAGCTGGTGCAGTCCGGAGCAGAGGTGAAGAAGCCA

GGAGCCTCTGTGAAGGTGAGCTGCAAGGCCAGCGGCTACTCCTTCACCGG

CTACTTCATGAACTGGGTGCGGCAGGCACCAGGACAGTCTCTGGAGTGGA

TCGGCAGGATCAACCCTTACAATGGCGACACATTCTATAATCAGAAGTTT

AAGGGCCGGGTGACCATCACAAGAGATACCTCCGCCTCTACAGCCTACAT

GGAGCTGAGCTCCCTGAGGAGCGAGGACACCGCCGTGTACTATTGTGCCC

GCGGCAACCACTACACAATGGATTATTGGGGCCAGGGCACCCTGGTGACA

GTGTCTAGCGCTAGCACCAAGGGCCCATCGGTCTTCCCCCTGGCACCCTC

CTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACC

AGCGGCGTGCACACCTTCCCGGCTGTCCTACAGTCCTCAGGACTCTACTC

CCTCAGCAGCGTGGTGACCGTGCCCTCCAGCAGCTTGGGCACCCAGACCT

ACATCTGCAACGTGAATCACAAGCCCAGCAACACCAAGGTGGACAAGAAA

-continued

GTTGAGCCCAAATCTTGTGACAAAACTCACACATGCCCACCGTGCCCAGC

ACCTGAACTCCTGGGGGGACCGTCAGTCTTCCTCTTCCCCCCAAAACCCA

AGGACACCCTCATGATCTCCCGGACCCCTGAGGTCACATGCGTGGTGGTG

GACGTGAGCCACGAAGACCCTGAGGTCAAGTTCAACTGGTACGTGGACGG

CGTGGAGGTGCATAATGCCAAGACAAAGCCGCGGGAGGAGCAGTACAACA

GCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCC

CATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTG

CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

TGA.

SEQ ID NO: 20 is the DNA sequence of the Light chain of Grafted Ab-VL (AHF00208-VL = AHF00220-VL) as referred to above:

ATGGGCTGGAGCTGGATCCTGCTGTTCCTCCTGAGCGTGACAGCAGGAGT

GCACAGCGACATCCAGATGACCCAGTCTCCTAGCTCCCTGTCCGCCTCTG

TGGGCGACAGGGTGACCATCACATGCAAGGCCAGCCAGGATATCAACAGC

TACCTGTCCTGGTATCAGCAGAAGCCCGGCAAGGCCCCTAAGCTGCTGAT

CTACCGGGCCAATAGACTGGTGGACGGAGTGCCATCCCGGTTCAGCGGAT

CCGGCTCTGGCACCGATTTCACCTTTACAATCTCTAGCCTGCAGCCAGAG

GACATCGCCACATACTATTGTCTGCAGTATGATGAGTTCCCCCTGACCTT

TGGCGGCGGCACAAAGCTGGAGATCAAGCGAACGGTGGCTGCACCATCTG

TCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGTT

AG

SEQ ID NO: 21 is the DNA sequence of the AHF00217-VL as referred to above:

ATGGGCTGGAGCTGGATCCTGCTGTTCCTCCTGAGCGTGACAGC

AGGAGTGCACAGCGACATCCAGATGACCCAGTCTCCTAGCTCCCTGTCCG

CCTCTGTGGGCGACAGGGTGACCATCACATGCAAGGCCAGCCAGGATATC

AACAGCTACCTGTCCTGGTATCAGCAGAAGCCCGGCAAGGCCCCTAAGCT

GCTGATCTACCGGGCCAATAGACTGGTGGACGGAGTGCCATCCCGGTTCA

GCGGATCCGGCTCTGGCACCGATTACACCTTTACAATCTCTAGCCTGCAG

CCAGAGGACATCGCCACATACTATTGTCTGCAGTATGATGAGTTCCCCCT

GACCTTTGGCGGCGGCACAAAGCTGGAGATCAAGCGAACGGTGGCTGCAC

-continued

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAAGCAGACTACGAGAAACACAAAGTCTACGCCTGCGAAGT

CACCCATCAGGGCCTGAGCTCGCCCGTCACAAAGAGCTTCAACAGGGGAG

AGTGTTAG.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming but would be a routine undertaking for those of ordinary skill in the art having the benefit of this disclosure.

Cancer

Figure 1:
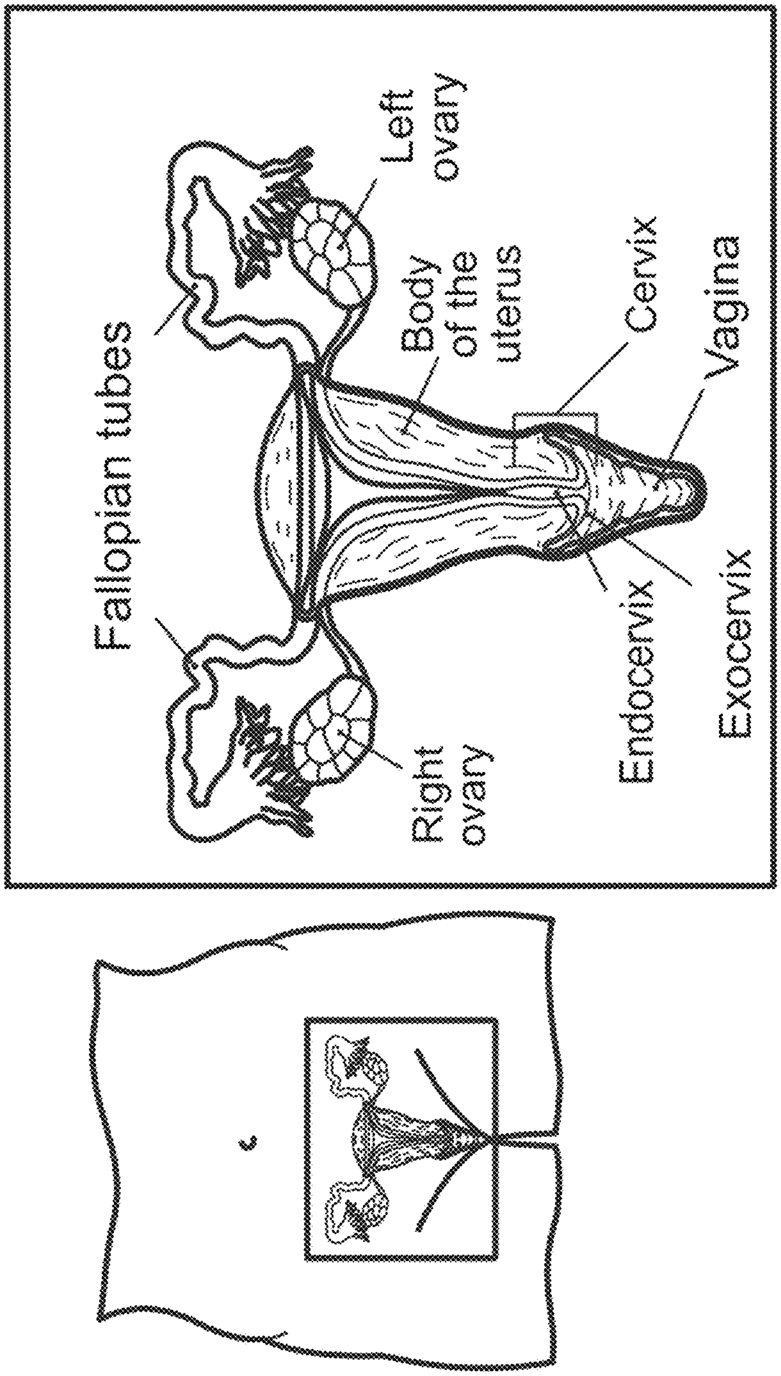
FIG. 1 summarizes key statistics concerning ovarian and pancreatic cancer.

Ovarian cancer is the most lethal gynecologic malignance and pancreatic cancer is the most lethal cancer overall. Standard of care of both ovarian and pancreatic cancer (FIG. 1) involves surgery and chemotherapy. However, patient survival has not been significantly improved over the past decade, partly due to the lack of novel therapeutics.

Figure 2:
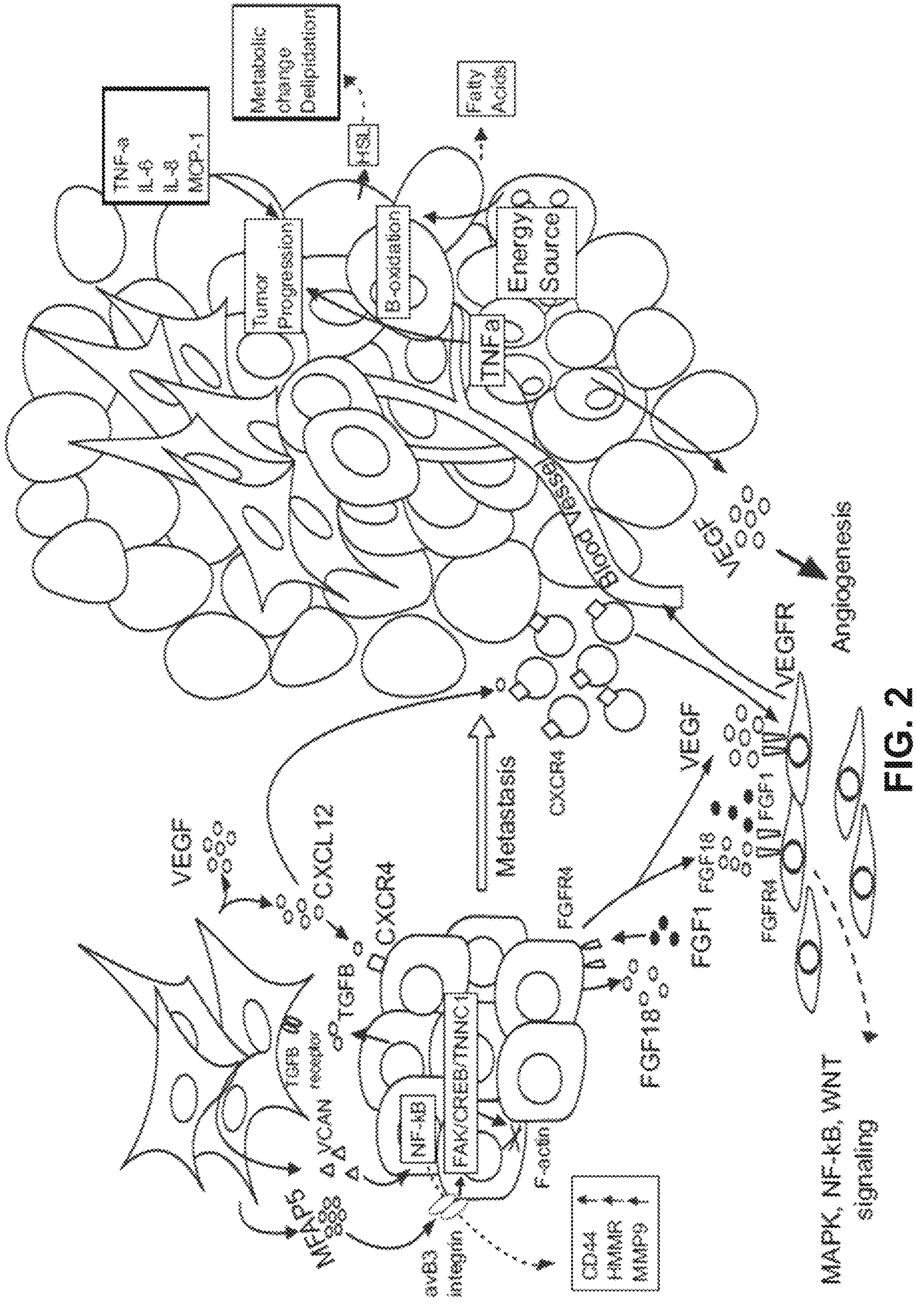
FIG. 2 shows inter-cellular communication in the complex tumor microenvironment at primary and metastatic sites.

One critically important, yet often overlooked, component to the tumor progression process is the tumor microenvironment. Primarily composed of fibroblasts and extracellular matrix proteins (ECM) as well as endothelial cells and lymphocytic infiltrate, the tumor microenvironment has been shown to directly affect cell growth, migration, and differentiation (FIG. 2). Since the tumor microenvironment has the potential to promote tumor initiation and progression, thereby, presenting a unique approach to treat cancer.

Figure 3:
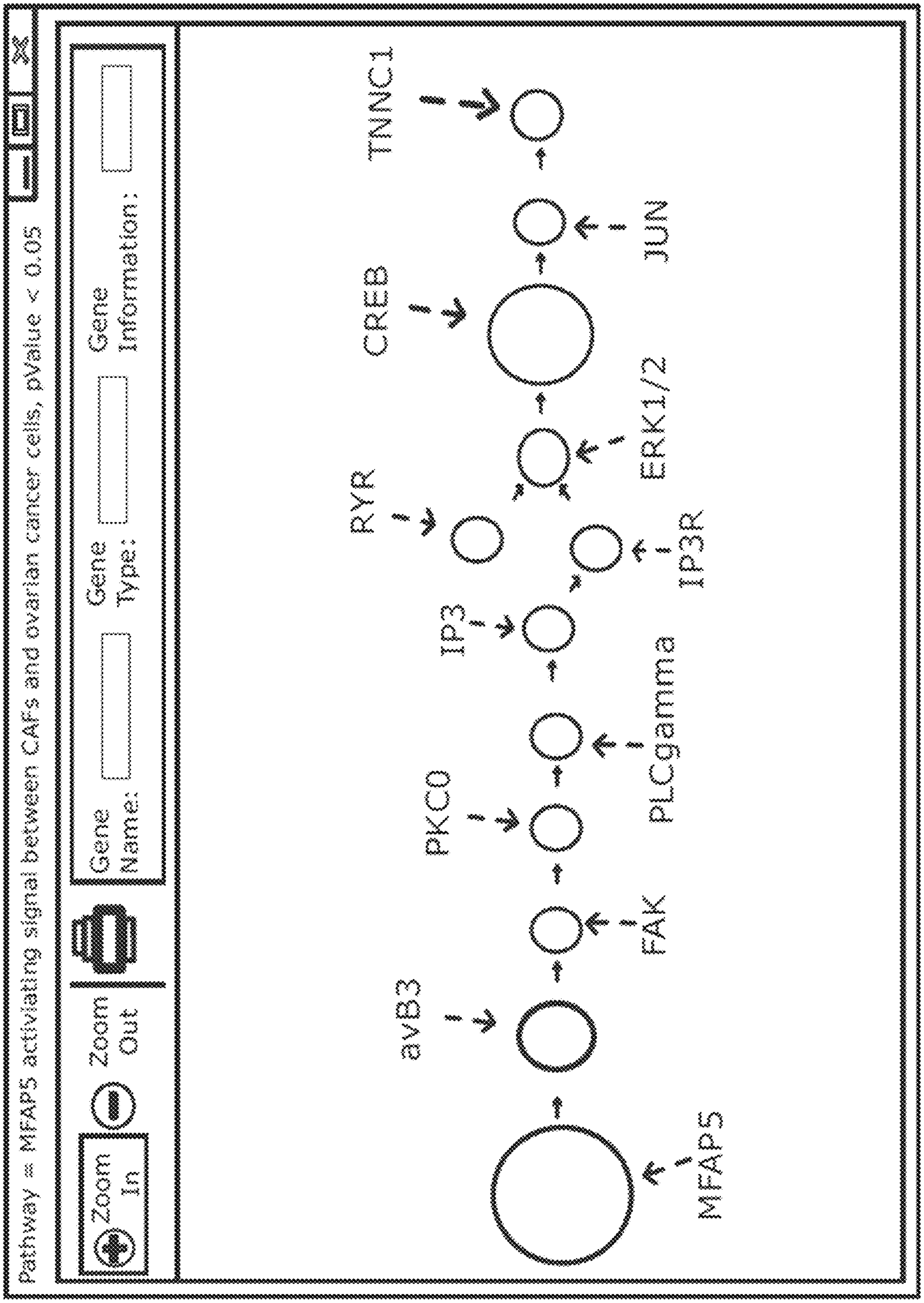
FIG. 3 shows the discovery of cancer drug targets with tumor microenvironment computational modeling.
Figure 4:
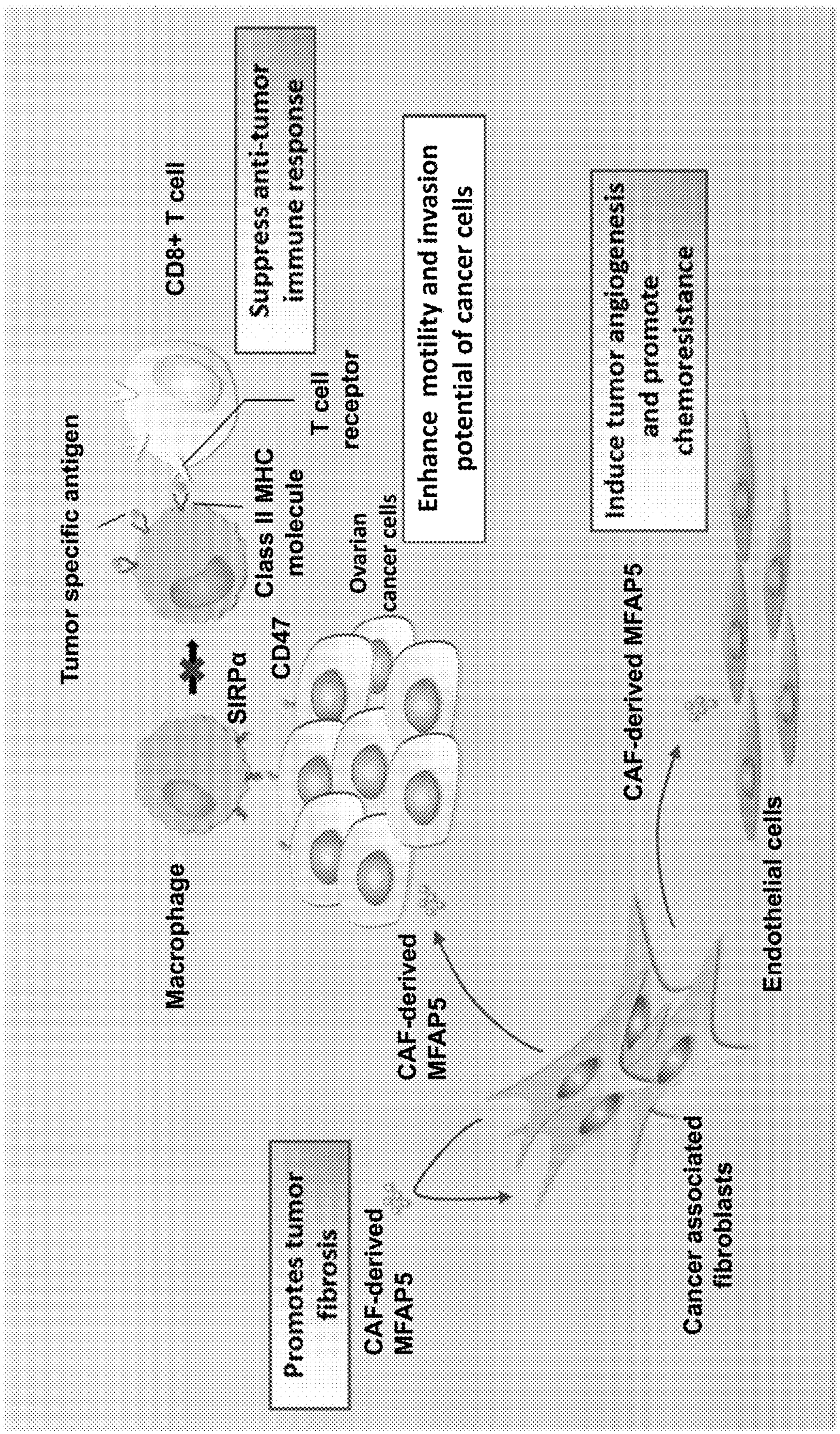
FIG. 4 shows MFAP5 is a novel target for cancer treatment.

In the present methods, a proprietary system biology technology, denoted "CCCExplorer," has been developed to identify MFAP5 as a key candidate that mediates crosstalk between fibroblast and cancer cells in tumor microenvironment using multicellular RNAseq data (FIG. 3). These data suggested that microfibrillar-associated protein 5 (MFAP5) is highly expressed by ovarian and pancreatic cancer associated fibroblasts (CAFs) and is associated with poor patient survival (FIG. 4). Further association study on the functional roles of MFAP5 on ovarian cancer revealed that CAF-derived MFAP5 could promote cancer cell migration and invasion, tumor angiogenesis and chemoresistance of tumor cells. In vivo studies using mouse model confirmed the roles of MFAP5 in promoting tumor progression. On the other hand, knock-down of MFAP5 in the microenvironment suppressed tumor growth, suggesting that MFAP5 can serve as a therapeutic target in ovarian cancer treatment.

Figure 5:
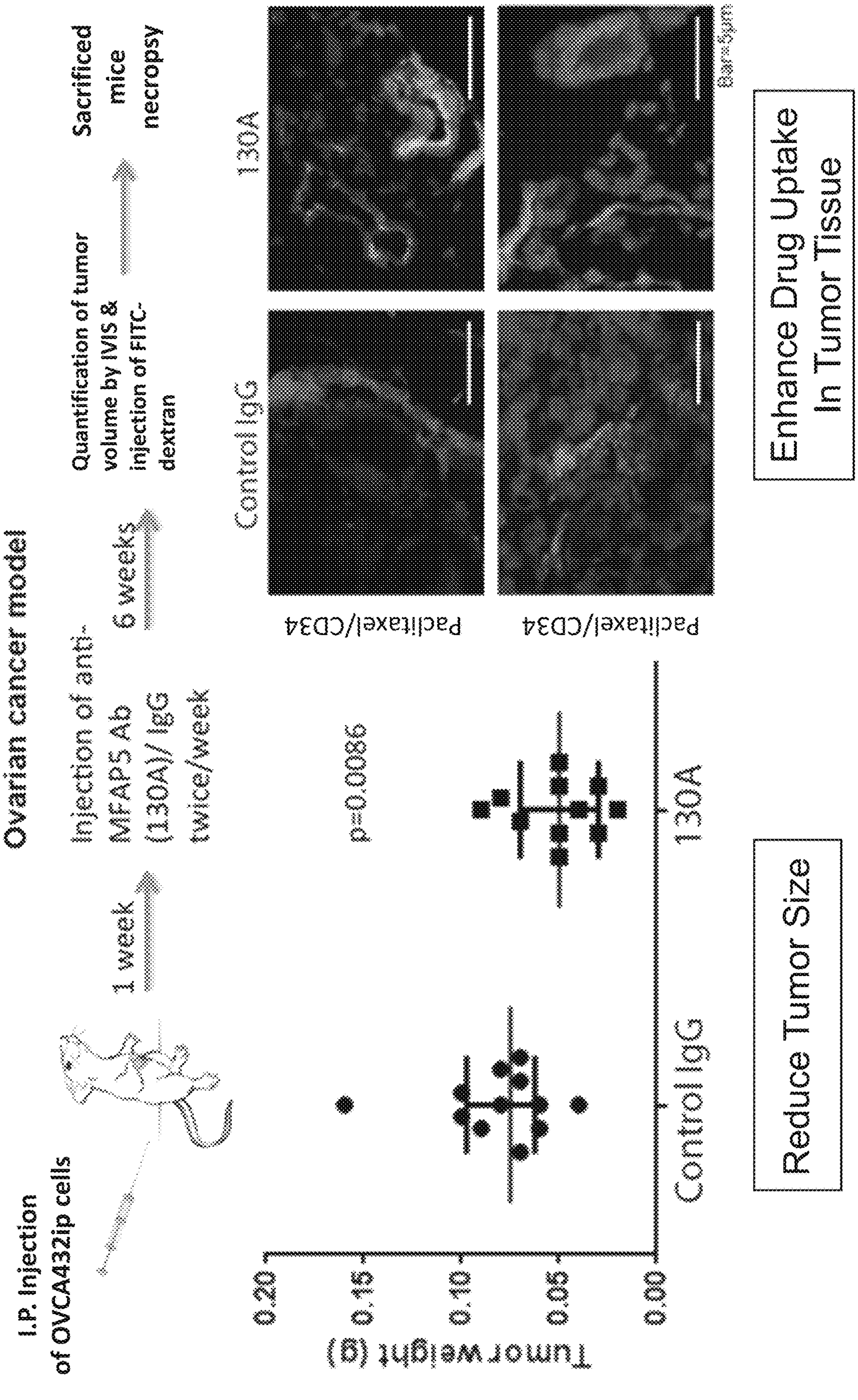
FIG. 5 shows the use of Mfap5-targeting monoclonal antibody in the treatment of cancer in ovarian and pancreatic animal models.
Figure 5:
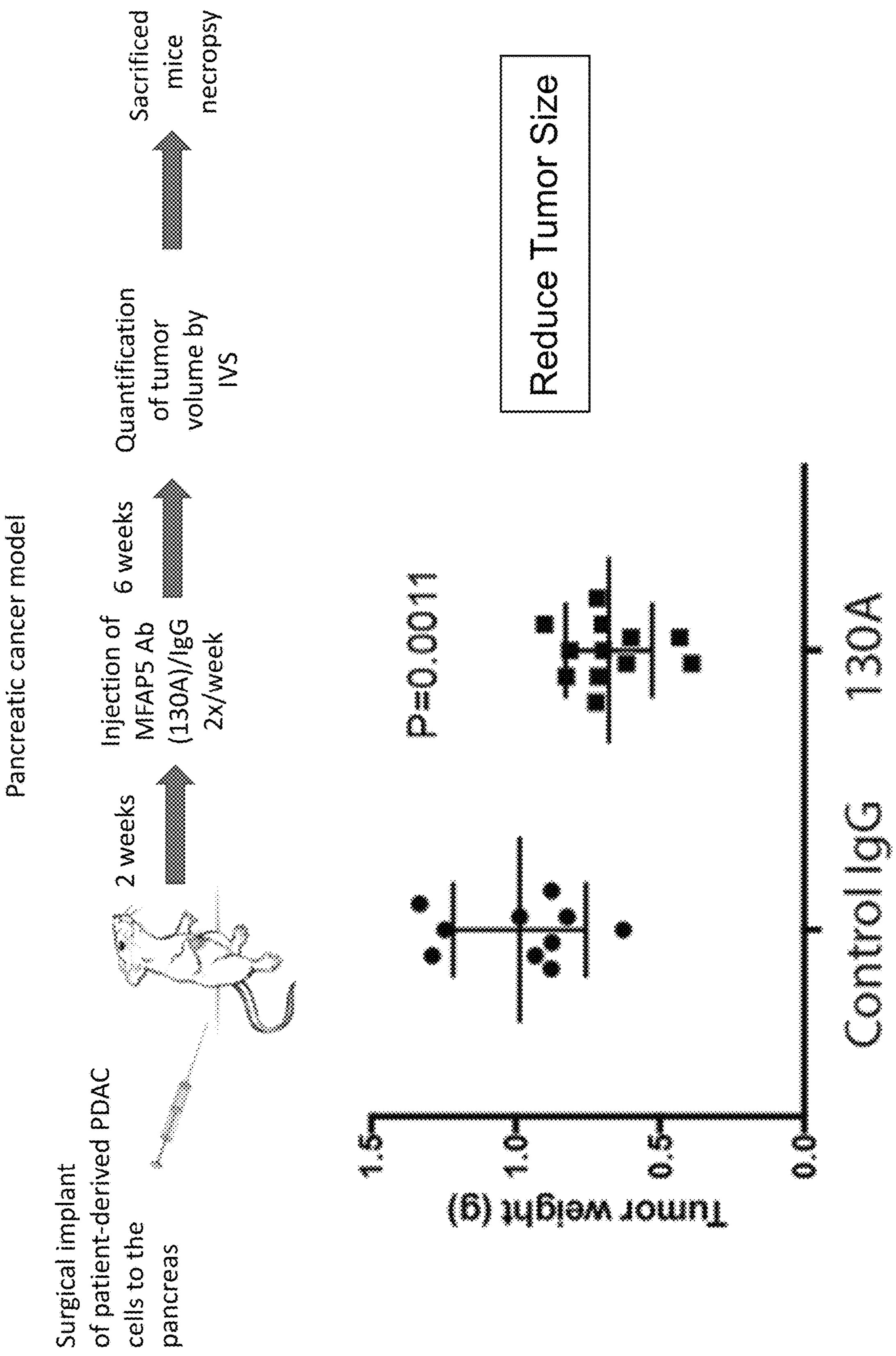

To develop novel therapeutic agents that target MFAP5, multiple anti-MFAP5 mouse monoclonal antibodies were generated (FIG. 5). Further analysis on binding-specificity and functional epitope was preformed, together with in vitro functional assays, three clones were identified which inhibited ovarian and pancreatic cancer cell motility and invasion potential. The efficacy of one of the antibody clones, 130A, on ovarian and pancreatic cancer treatment was tested in xenograft and PDX mouse models. Animal study results suggested the anti-MFAP5 monoclonal antibody that was developed suppressed tumor progression.

Figure 6:
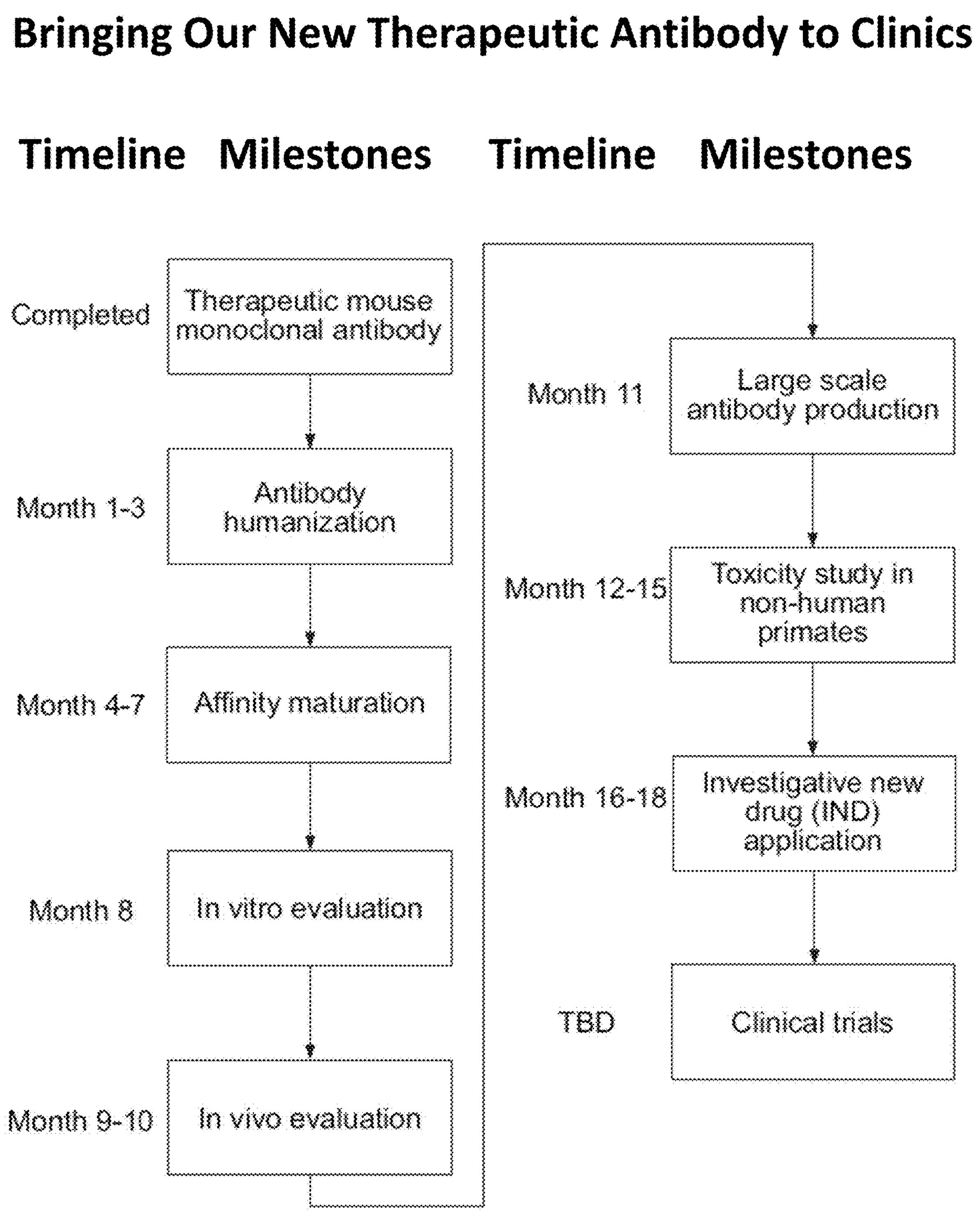
FIG. 6 shows an exemplary timeline for the fast-track of the new class of therapeutic antibodies disclosed herein to the clinic for use in treating ovarian and pancreatic cancer.

In the following examples, the functional roles of stromal MFAP5 in cancer progression was characterized and its prognostic significance was determined. These results also suggested that MFAP5 targeting monoclonal antibody can serve as a therapeutic agent in cancer treatment, which can be fast-tracked to clinical trials (see FIG. 6) for ready commercial development.

In particular embodiments, a chimeric antibody clone (mouse variable domains fused with human IgG backbone) has been described that was generated based on the anti-MFAP5 monoclonal antibody clone designated herein as "130A."

No current mainstream therapy of ovarian cancer has been focused on targeting stromal factors, despite the fact that tumor stromal could compose up to 70% of the total tumor mass. Therapy that targets both stromal and tumor could potentially be more effective. MFAP5 expression in the tumor microenvironment directly associates with patient survival and MFAP5 has essential roles in ovarian cancer progression. Furthermore, MFAP5-targeting antibodies demonstration inhibitory effect on ovarian and pancreatic cancer progression. Taken together, patients with high stromal MFAP5 expression could benefit by treatment with MFAP5-targeting monoclonal antibodies.

Stromal Microenvironment

The stromal microenvironment plays important roles in tumor progression and disease prognosis. However, strategies used to overcome the malignant phenotypes of cancer cells modulated by the microenvironment have not been thoroughly explored. The following examples evaluated the therapeutic efficacy of a newly-developed monoclonal antibody that targets microfibril associated protein 5 (MFAP5), a cancer associated fibroblast-derived secretory protein, in ovarian and pancreatic cancer animal models. The results demonstrated that anti-MFAP5 monoclonal antibody treatment suppressed intratumoral microvessel leakiness, enhanced paclitaxel bioavailability and inhibited tumor progression in both ovarian and pancreatic cancer mouse models, which suggested that MFAP5 blockade using such monoclonal antibodies represents a powerful new therapeutic approach for treating these diseases and improving patient survival. Furthermore, the use of such MAbs in combination with existing chemotherapeutic agents can provide improved results over the use of chemotherapy alone.

Recent studies demonstrate the role of the tumor microenvironment in tumor progression. However, strategies used to overcome the malignant phenotypes of cancer cells modulated by the microenvironment have not been thoroughly explored. In this study, the therapeutic efficacy of a newly developed monoclonal antibody targeting microfibrillar-associated protein 5 (MFAP5), which is secreted predominately by CAFs, was evaluated in ovarian and pancreatic cancer animal models.

Monoclonal antibodies were developed using human MFAP5 recombinant protein as an antigen in mice and antibodies from hybridoma clones were evaluated for their specificity to human and murine MFAP5. An Octet RED384 system was used to determine the kinetics of binding affinity and the specificity of the antibody clones, which were followed by epitope mapping and functional characterization by in vitro assays. The therapeutic efficacy of a lead anti-MFAP5 antibody clone 130A in tumor suppression was evaluated by ovarian tumor- and pancreatic tumor-bearing mouse models.

Three hybridoma clones, which produced antibodies with high affinity and specificity to MFAP5, were selected for functional studies. Antibody clone 130A, which recognizes a common epitope shared between human and murine MFAP5 protein, were further selected for in vivo studies. Results showed that clone 130A down-regulated MFAP5-induced collagen production in CAFs, suppressed intratumoral microvessel leakiness, and enhanced paclitaxel bioavailability in both ovarian and pancreatic cancer mouse models.

These data suggest that MFAP5 blockade using an immunologic approach inhibits fibrosis, induces tumor vessel normalization and enhances chemosensitivity in ovarian and pancreatic cancer, and can be used as a novel therapeutic agent.

Antibodies

The terms "antibody" and "immunoglobulin", as used herein, refer broadly to any immunological binding agent, including polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the difference classes of immunoglobulins are termed $\alpha$, $\delta$, $\varepsilon$, $\gamma$ and $\mu$, respectively. The subunit structures and three-dimensional configurations of different classes of immunoglobulins are well known.

Generally, where antibodies rather than antigen binding regions are used in the invention, IgG and/or IgM are preferred because they are the most common antibodies in the physiological situation and because they are most easily made in a laboratory setting.

The "light chains" of mammalian antibodies are assigned to one of two clearly distinct types: kappa ($\kappa$) and lambda ($\lambda$), based on the amino acid sequences of their constant domains. There is essentially no preference to the use of $\kappa$ or $\lambda$ light chains in the antibodies of the present invention.

The use of monoclonal antibodies (MAbs) or derivatives thereof is much preferred. MAbs are recognized to have certain advantages, e.g., reproducibility and large-scale production, that makes them suitable for clinical treatment. The invention thus provides monoclonal antibodies of the murine, human, monkey, rat, hamster, rabbit and even frog or chicken origin. Murine, human or humanized monoclonal antibodies will generally be preferred.

As will be understood by those in the art, the immunological binding reagents encompassed by the term "antibody" extend to all antibodies from all species, and antigen binding fragments thereof, including dimeric, trimeric and multimeric antibodies; bispecific antibodies; chimeric antibodies; human and humanized antibodies; recombinant and engineered antibodies, and fragments thereof.

The term "antibody" is thus used to refer to any antibody-like molecule that has an antigen binding region, and this term includes antibody fragments such as Fab', Fab, $F(ab')_2$, single domain antibodies (DABs), Fv, scFv (single chain Fv), linear antibodies, diabodies, and the like. The techniques for preparing and using various antibody-based constructs and fragments are well known in the art. Diabodies in particular are further described in EP404097 and PCT Intl. Pat. Appl. Publ. No. WO 93/11161 (each of which is specifically incorporated herein in its entirety by express reference thereto).

"Humanized" Antibodies

In certain embodiments, the antibodies employed will be "humanized," part-human, or human antibodies. "Humanized" antibodies are generally chimeric monoclonal antibodies from mouse, rat, or other non-human species, bearing human constant and/or variable region domains ("part-human chimeric antibodies"). Various humanized monoclonal antibodies for use in the present invention will be chimeric antibodies wherein at least a first antigen binding region, or complementarity determining region (CDR), of a mouse, rat or other non-human monoclonal antibody is operatively attached to, or "grafted" onto, a human antibody constant region or "framework."

"Humanized" monoclonal antibodies for use herein may also be monoclonal antibodies from non-human species wherein one or more selected amino acids have been exchanged for amino acids more commonly observed in human antibodies. This can be readily achieved using routine recombinant technology, and particularly, site-specific mutagenesis.

Entirely human, rather than "humanized", antibodies may also be prepared and used in the present invention. Such human antibodies may be obtained from healthy subjects by simply obtaining a population of mixed peripheral blood lymphocytes from a human subject, including antigen-presenting and antibody-producing cells, and stimulating the cell population in vitro by admixing with an immunogenically effective amount of a MFAP5 sample. The human anti-MFAP5 antibody-producing cells, once obtained, are used in hybridoma and/or recombinant antibody production.

Further techniques for human monoclonal antibody production include immunizing a transgenic animal, preferably a transgenic mouse, which comprises a human antibody library with an immunogenically effective amount of a MFAP5 sample. This also generates human anti-MFAP5 antibody-producing cells for further manipulation in hybridoma and/or recombinant antibody production, with the advantage that spleen cells, rather than peripheral blood cells, can be readily obtained from the transgenic animal or mouse.

Human antibodies generally have at least three potential advantages for use in human therapy. First, because the effector portion is human, it may interact better with the other parts of the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, the half-life in the human circulation will be similar to naturally occurring human antibodies, allowing smaller and less frequent doses to be given.

Various methods for preparing human anti-MFAP5 antibodies are provided herein. In addition to human antibodies, "humanized" antibodies have many advantages. "Humanized" antibodies are generally chimeric or mutant monoclonal antibodies from mouse, rat, hamster, rabbit or other species, bearing human constant and/or variable region domains or specific changes. Techniques for generating a so-called "humanized" anti-MFAP5 antibody are well known to those of skill in the art.

Humanized antibodies also share the foregoing advantages. First, the effector portion is still human. Second, the human immune system should not recognize the framework or constant region as foreign, and therefore the antibody response against such an injected antibody should be less than against a totally foreign mouse antibody. Third, injected humanized antibodies, as opposed to injected mouse antibodies, will presumably have a half-life more similar to naturally occurring human antibodies, also allowing smaller and less frequent doses.

A number of methods have been described to produce humanized antibodies. Controlled rearrangement of antibody domains joined through protein disulfide bonds to form new, artificial protein molecules or "chimeric" antibodies can be utilized. Recombinant DNA technology can also be used to construct gene fusions between DNA sequences encoding mouse antibody variable light and heavy chain domains and human antibody light and heavy chain constant domains.

DNA sequences encoding the antigen binding portions or complementarity determining regions (CDR's) of murine monoclonal antibodies can be grafted by molecular means into the DNA sequences encoding the frameworks of human antibody heavy and light chains. The expressed recombinant products are called "reshaped" or humanized antibodies and comprise the framework of a human antibody light or heavy chain and the antigen recognition portions, CDR's, of a murine monoclonal antibody.

Another method for producing humanized antibodies is described in U.S. Pat. No. 5,639,641, specifically incorporated herein in its entirety by express reference thereto. The method provides, via resurfacing, humanized rodent antibodies that have improved therapeutic efficacy due to the presentation of a human surface in the variable region. In the method: (1) position alignments of a pool of antibody heavy and light chain variable regions is generated to give a set of heavy and light chain variable region framework surface exposed positions, wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5A of any atom of any residue of the complementarity determining regions of the rodent antibody; and (5) the humanized rodent antibody having binding specificity is produced.

A similar method for producing humanized antibodies is described in U.S. Pat. Nos. 5,693,762; 5,693,761; 5,585,089; and 5,530,101 (each of which is specifically incorporated herein in its entirety by express reference thereto). These methods generally involve producing humanized immunoglobulins having one or more complementarity determining regions (CDR's) and possible additional amino acids from a donor immunoglobulin and a framework region from an accepting human immunoglobulin. Each humanized immunoglobulin chain usually comprises, in addition to the CDR's, amino acids from the donor immunoglobulin framework that are capable of interacting with the CDR's to effect binding affinity, such as one or more amino acids that are immediately adjacent to a CDR in the donor immunoglobulin or those within about 3A as predicted by molecular modeling. The heavy and light chains may each be designed by using any one, any combination, or all of the various position criteria as described in U.S. Pat. Nos. 5,693,762; 5,693,761; 5,585,089; and 5,530,101 (each of which is specifically incorporated herein in its entirety by express reference thereto). When combined into an intact antibody, the humanized immunoglobulins are substantially non-immunogenic in humans and retain substantially the same affinity as the donor immunoglobulin to the original antigen.

An additional method for producing humanized antibodies is described in U.S. Pat. Nos. 5,565,332 and 5,733,743 (each of which is specifically incorporated herein in its entirety by express reference thereto). This method generally combines the concept of humanizing antibodies with the phagemid libraries also described in detail herein. In an overall sense, the method utilizes sequences from the antigen binding site of an antibody or population of antibodies directed against an antigen of interest. Thus, for a single rodent antibody, sequences comprising part of the antigen binding site of the antibody may be combined with diverse repertoires of sequences of human antibodies that can, in combination, create a complete antigen binding site.

The antigen binding sites created by this process differ from those created by CDR grafting, in that only the portion of sequence of the original rodent antibody is likely to make contacts with antigen in a similar manner. The selected human sequences are likely to differ in sequence and make alternative contacts with the antigen from those of the original binding site. However, the constraints imposed by binding of the portion of original sequence to antigen and the shapes of the antigen and its antigen binding sites, are likely to drive the new contacts of the human sequences to the same region or epitope of the antigen. This process has therefore been termed "epitope imprinted selection" (EIS).

Starting with an animal antibody, one process results in the selection of antibodies that are partly human antibodies. Such antibodies may be sufficiently similar in sequence to human antibodies to be used directly in therapy or after alteration of a few key residues. Sequence differences between the rodent component of the selected antibody with human sequences could be minimized by replacing those residues that differ with the residues of human sequences, for example, by site directed mutagenesis of individual residues, or by CDR grafting of entire loops. However, antibodies with entirely human sequences can also be created. EIS therefore offers a method for making partly human or entirely human antibodies that bind to the same epitope as animal or partly human antibodies respectively. In EIS, repertoires of antibody fragments can be displayed on the surface of filamentous phase and the genes encoding fragments with antigen binding activities selected by binding of the phage to antigen.

Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567 (each of which is specifically incorporated herein in its entirety by express reference thereto). PCT Intl. Pat. Appl. Publ. Nos. WO 98/45331 and WO 98/45332 are believed to be particularly instructive and are also specifically incorporated herein in their entirety by express reference thereto to further exemplify the principles of humanization as applied to anti-MFAP5 antibodies.

Antibody Fragments and Derivatives

Irrespective of the source of the original MFAP5-blocking, anti-MFAP5 antibody, either the intact antibody, antibody multimers, or any one of a variety of functional, antigen-binding regions of the antibody may be used in the present invention. Exemplary functional regions include diabodies, linear antibodies and scFv, Fv, Fab', Fab, $F(ab')_2$ fragments of the anti-MFAP5 antibodies. Techniques for preparing such constructs are well known to those in the art and are further exemplified herein.

The choice of antibody construct may be influenced by various factors. For example, prolonged half-life can result from the active re-adsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

Antibody fragments can be obtained by proteolysis of the whole immunoglobulin by the non-specific thiol protease, papain. Papain digestion yields two identical antigen-binding fragments, termed "Fab fragments," each with a single antigen-binding site, and a residual "Fc fragment."

Papain must first be activated by reducing the sulfhydryl group in the active site with cysteine, 2 mercaptoethanol, or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion-exchange chromatography.

The usual procedure for preparation of $F(ab')_2$ fragments from IgG of rabbit and human origin is limited proteolysis by the enzyme pepsin. The conditions, 100× antibody excess w/w in acetate buffer at pH 4.5, 37° C., suggest that antibody is cleaved at the C-terminal side of the inter-heavy-chain disulfide bond. Rates of digestion of mouse IgG may vary with subclass and conditions should be chosen to avoid significant amounts of completely degraded IgG. In particular, $IgG_{2b}$ is susceptible to complete degradation. The other subclasses require different incubation conditions to produce optimal results, all of which is known in the art.

Pepsin treatment of intact antibodies yields an $F(ab')_2$ fragment that has two antigen-combining sites and is still capable of cross-linking antigen. Digestion of rat IgG by pepsin requires conditions including dialysis in 0.1 M acetate buffer, pH 4.5, and then incubation for four hours with 1% w/w pepsin; $IgG_1$ and $IgG_{2a}$ digestion is improved if first dialyzed against 0.1 M formate buffer, pH 2.8, at 4° C., for 16 hrs followed by acetate buffer. $IgG_{2b}$ gives more consistent results with incubation in staphylococcal V8 protease (3% wt./wt.) in 0.1 M sodium phosphate buffer, pH 7.8, for four hrs at 37° C.

An Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. $F(ab')_2$ antibody fragments were originally produced as pairs of Fab' fragments that have hinge cysteines between them. Other chemical couplings of antibody fragments are also known.

An "Fv fragment" is the minimum antibody fragment that contains a complete antigen-recognition and binding site. This region consists of a dimer of one heavy chain and one light chain variable domain in tight, con-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the sFv to form the desired structure for antigen binding.

The following patents are specifically incorporated herein in their entirety by express reference thereto for supplementing the present teachings regarding the preparation and use of functional, antigen-binding regions of antibodies, including scFv, Fv, Fab', Fab and $F(ab')_2$ fragments of the anti-VEGF antibodies: U.S. Pat. Nos. 5,855,866; 5,965,132; 6,051,230; 6,004,555; and 5,877,289.

"Diabodies" are small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described in EP 404,097 and PCT Intl. Pat. Appl. Publ. No. WO93/11161, each of which is specifically incorporated herein in its entirety by express reference thereto. "Linear antibodies," which can be bispecific or monospecific, comprise a pair of tandem Fd segments ($V_H$-$C_H1$-$V_H$-$C_H1$) that form a pair of antigen binding regions.

In using a Fab' or antigen binding fragment of an antibody, with the attendant benefits on tissue penetration, one may derive additional advantages from modifying the fragment to increase its half-life. A variety of techniques may be employed, such as manipulation or modification of the antibody molecule itself, as well as conjugation to inert carriers. Any conjugation solely for the purpose of increasing half-life (rather than to deliver an agent to a target), should be approached carefully in that Fab' and other fragments are chosen to penetrate tissues. Nonetheless, conjugation to non-protein polymers, such PEG and the like, is also contemplated to be useful in certain applications of the disclosed antibody compositions.

Modifications other than conjugation are therefore based upon modifying the structure of the antibody fragment to render it more stable, and/or to reduce the rate of catabolism in the body. One mechanism for such modifications is the use of D-amino acids in place of L-amino acids. Those of ordinary skill in the art will understand that the introduction of such modifications needs to be followed by rigorous testing of the resultant molecule to ensure that it still retains the desired biological properties. Further stabilizing modifications include the use of the addition of stabilizing moieties to either the N-terminal or the C-terminal, or both, which is generally used to prolong the half-life of biological molecules. By way of example only, one may wish to modify the termini by acylation or amination.

Moderate conjugation-type modifications for use with the present disclosure include incorporating a salvage receptor binding epitope into the antibody fragment. Techniques for achieving this include mutation of the appropriate region of the antibody fragment or incorporating the epitope as a peptide tag that is attached to the antibody fragment. PCT Intl. Pat. Appl. Publ. No. WO 96/32478 is specifically incorporated herein in its entirety by express reference thereto for the purposes of further exemplifying such technology. Salvage receptor binding epitopes are typically regions of three or more amino acids from one or two lops of the Fc domain that are transferred to the analogous position on the antibody fragment. The salvage receptor binding epitopes of WO 98/45331 are also specifically incorporated herein by reference for use with the present invention.

Exemplary Definitions

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. The following references provide one of skill with a general definition of many of the terms used in this invention: *Dictionary of Biochemistry and Molecular Biology*, (2nd Ed.) J. Stenesh (Ed.), Wiley-Interscience (1989); *Dictionary of Microbiology and Molecular Biology* (3rd Ed.), P. Singleton and D. Sainsbury (Eds.), Wiley-Interscience (2007); *Chambers Dictionary of Science and Technology* (2nd Ed.), P. Walker (Ed.), Chambers (2007); *Glossary of Genetics* (5th Ed.), R. Rieger et al. (Eds.), Springer-Verlag (1991); and *The HarperCollins Dictionary of Biology*, W. G. Hale and J. P. Margham, (Eds.), HarperCollins (1991).

Although any methods and compositions similar or equivalent to those described herein can be used in the practice or testing of the present invention, the preferred methods, and compositions are described herein. For purposes of the present invention, the following terms are defined below for sake of clarity and ease of reference:

In accordance with long standing patent law convention, the words "a" and "an," when used throughout this application and in the claims, denote "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

The terms "antibody" and "immunoglobulin", as used herein, refer broadly to any immunological binding agent, including polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the difference classes of immunoglobulins are termed $\alpha$, $\delta$, $\varepsilon$, $\gamma$ and $\mu$, respectively. The subunit structures and three-dimensional configurations of different classes of immunoglobulins are well known.

Biocompatible" refers to a material that, when exposed to living cells, will support an appropriate cellular activity of the cells without causing an undesirable effect in the cells, such as a change in a living cycle of the cells, a change in a proliferation rate of the cells, or a cytotoxic effect.

The term "biologically-functional equivalent" is well understood in the art and is further defined in detail herein. Accordingly, sequences that have about 85% to about 90%; or more preferably, about 91% to about 95%; or even more preferably, about 96% to about 99%; of nucleotides that are identical or functionally-equivalent to one or more of the nucleotide sequences provided herein are particularly contemplated to be useful in the practice of the methods and compositions set forth in the instant application.

As used herein, "biomimetic" shall mean a resemblance of a synthesized material to a substance that occurs naturally in a human body and which is not rejected by (e.g., does not cause an adverse reaction in) the human body.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof, that is pharmaceutically acceptable for administration to the relevant animal. The use of one or more delivery vehicles for chemical compounds in general, and chemotherapeutics in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed chemotherapeutic compositions.

"Chemotherapeutic agents", as used herein, refer to classical chemotherapeutic agents or drugs used in the treatment of malignancies. This term is used for simplicity notwithstanding the fact that other compounds may be technically described as chemotherapeutic agents in that they exert an anti-cancer effect. However, "chemotherapeutic" has come to have a distinct meaning in the art and is being used according to this standard meaning. A number of exemplary chemotherapeutic agents is described herein. Those of ordinary skill in the art will readily understand the uses and appropriate doses of chemotherapeutic agents, although the doses may well be reduced when used in combination with the present invention.

A new class of drugs that may also be termed "chemotherapeutic agents" are agents that induce apoptosis. Any one or more of such drugs, including genes, vectors, antisense constructs and ribozymes, as appropriate, may also be used in conjunction with the present invention. Currently preferred second agents are anti-angiogenic agents, such as angiostatin, endostatin, vasculostatin, canstatin and maspin.

Other exemplary anti-cancer agents include, e.g., neomycin, podophyllotoxin(s), TNF-$\alpha$, $\alpha_v\beta_3$ antagonists, calcium ionophores, calcium-flux inducing agents, and any derivative or prodrug thereof. Currently preferred anti-tubulin drugs include colchicine, taxol, vinblastine, vincristine, vindescine, a combretastatin or a derivative or prodrug thereof.

"Detectable or reporter agents" indirectly detectable in vitro include those that function in conjunction with further exogenous agent(s), such as detectable enzymes that yield a colored product on contact with a chromogenic substrate. Indirect detection in vitro also extends to detectable or reporter components or systems that comprise the first binding region that binds to an accessible component of a tumor cell, tumor vasculature (preferably) or tumor stroma (preferably) in combination with at least one detecting antibody that has immunospecificity for the first binding region. The "detecting antibody" is preferably a "secondary antibody" that is attached to a direct or indirect detectable agent, such a radiolabel or enzyme. Alternatively, a "secondary and tertiary antibody detection system" may be used, including a first detecting antibody that has immunospecificity for the first binding region in combination with a second detecting antibody that has immunospecificity for the first detecting antibody, the second detecting antibody being attached to a direct or indirect detectable agent.

The term "effective amount," as used herein, refers to an amount that is capable of treating or ameliorating a disease or condition or otherwise capable of producing an intended therapeutic effect.

As used herein, the term "expression" refers to the biological production of a product encoded by a coding sequence. In most cases, a polynucleotide (i.e., DNA) sequence, including the coding sequence, is transcribed to form a messenger-RNA (mRNA). The messenger-RNA is then translated to form a polypeptide product that has a relevant biological activity. The process of expression may involve further processing steps to the RNA product of transcription, such as splicing to remove introns, and/or post-translational processing of a polypeptide product.

The term "for example" or "e.g.," as used herein, is used merely by way of example, without limitation intended, and should not be construed as referring only those items explicitly enumerated in the specification.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state.

"Isolated substantially away from other coding sequences" means that the coding segment or isolated gene portion of interest forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

As used herein, the term "kit" may be used to describe variations of the portable, self-contained enclosure that includes at least one set of reagents, components, or pharmaceutically-formulated compositions to conduct one or more of the assay methods of the present invention. Optionally, such kit may include one or more sets of instructions for use of the enclosed reagents, such as, for example, in a laboratory or clinical application.

The "light chains" of mammalian antibodies are assigned to one of two clearly distinct types: kappa (κ) and lambda (λ), based on the amino acid sequences of their constant domains. There is essentially no preference to the use of κ or λ light chains in the antibodies of the present disclosure.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

As used herein, the term "monoclonal," when used in reference to an antibody, refers to an antibody that is based upon, obtained from or derived from a single clone, including any eukaryotic, prokaryotic, or phage clone. The term monoclonal antibody is often abbreviated "MAb" in the singular, and "MAbs" in the plural.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally-occurring animals.

As used herein, the term "operably linked" refers to a linkage of two or more polynucleotides or two or more nucleic acid sequences, or at least one of each, in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner. A patient can be of any age at which the patient is able to respond to inoculation with an immunogen by generating an immune response. In particular embodiments, the mammalian patient is preferably human.

The phrase "pharmaceutically-acceptable" refers to molecular entities and compositions that preferably do not produce an allergic or similar untoward reaction when administered to a mammal, and, in particular, when administered to a human.

As used herein, "pharmaceutically-acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

As used herein, "polymer" means a chemical compound or mixture of compounds formed by polymerization and including repeating structural units. Polymers may be constructed in multiple forms and compositions or combinations of compositions.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures.

For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing or suppressing need not be absolute to be deemed medically useful.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from about 2 to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules including at least one amino acid polymer. Polypeptides and proteins of the present invention also include polypeptides and proteins that are or have been post-translationally modified and include any sugar or other derivative(s) or conjugate(s) added to the backbone amino acid chain.

"Purified," as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

A significant reduction is a "reproducible", i.e., consistently observed, reduction in binding. A "significant reduction" in terms of the present application is defined as a reproducible reduction (in 130A binding to MFAP5 in an ELISA) of at least about 70%, about 75% or about 80% at any ratio between about 1:10 and about 1:100. Antibodies with even more stringent cross-blocking activities will exhibit a reproducible reduction (in 130A binding to MFAP5 in an ELISA or other suitable assay) of at least about 82%, about 85%, about 88%, about 90%, about 92% or about 95% or so at any ratio between about 1:10 and about 1:100. Complete or near-complete cross-blocking, such as exhibiting a reproducible reduction in 130A binding to MFAP5 of about 99%, about 98%, about 97% or about 96% or so, although by no means required to practice the invention, is certainly not excluded.

The term "subject," as used herein, describes an organism, including mammals such as primates, to which treatment with the compositions according to the present invention can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

As used herein, the term "substantially free" or "essentially free" in connection with the amount of a component preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

As used herein, the term "substantially homologous" encompasses sequences that are similar to the identified sequences, such that antibodies raised against peptides having the identified sequences will react with peptides having the substantially homologous sequences. In some variations, the amount of detectable antibodies induced by the homologous sequence is identical to the amount of detectable antibodies induced by the identified sequence. In other variations, the amounts of detectable antibodies induced are substantially similar, thereby providing immunogenic properties. For example, "substantially homologous" can refer to at least about 75%, preferably at least about 80%, and more preferably at least about 85% or at least about 90% identity, and even more preferably at least about 95%, more preferably at least about 97% identical, more preferably at least about 98% identical, more preferably at least about 99% identical, and even more preferably still, at least substantially or entirely 100% identical (i.e., "invariant").

As used herein, "synthetic" shall mean that the material is not of a human or animal origin.

The term "therapeutically-practical period" means the period of time that is necessary for one or more active agents to be therapeutically effective. The term "therapeutically-effective" refers to reduction in severity and/or frequency of one or more symptoms, elimination of one or more symptoms and/or underlying cause, prevention of the occurrence of symptoms and/or their underlying cause, and the improvement or a remediation of damage.

A "therapeutic agent" may be any physiologically or pharmacologically active substance that may produce a desired biological effect in a targeted site in a subject. The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally occurring, produced by synthetic or recombinant methods, or a combination thereof. Drugs that are affected by classical multidrug resistance, such as *vinca* alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as a therapeutic agent. Cytokines may be also used as the therapeutic agent. Examples of such cytokines are lymphokines, monokines, and traditional polypeptide hormones. A cancer chemotherapy agent may be a preferred therapeutic agent. For a more detailed description of anticancer agents and other therapeutic agents, those skilled in the art are referred to any number of instructive manuals including, but not limited to, the *Physician's Desk Reference* and Hardman and Limbird (2001).

"Treating" or "treatment of" as used herein, refers to providing any type of medical or surgical management to a subject. Treating can include, but is not limited to, administering a composition comprising a therapeutic agent to a subject. "Treating" includes any administration or application of a compound or composition of the invention to a subject for purposes such as curing, reversing, alleviating, reducing the severity of, inhibiting the progression of, or reducing the likelihood of a disease, disorder, or condition or one or more symptoms or manifestations of a disease, disorder, or condition. In certain aspects, the compositions of the present invention may also be administered prophylactically, i.e., before development of any symptom or manifestation of the condition, where such prophylaxis is warranted. Typically, in such cases, the subject will be one that has been diagnosed for being "at risk" of developing such a disease or disorder, either as a result of familial history, medical record, or the completion of one or more diagnostic or prognostic tests indicative of a propensity for subsequently developing such a disease or disorder.

The section headings used throughout are for organizational purposes only and are not to be construed as limiting the subject matter described. All documents, or portions of documents, cited in this application (including, but not limited to, patents, patent applications, articles, books, and treatises) are expressly incorporated herein in their entirety by express reference thereto. In the event that one or more of the incorporated literature and similar materials defines a term in a manner that contradicts the definition of that term in this application, this application controls.

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

Anticancer Immunotherapy by MFAP5 Blockade Inhibits Fibrosis and Enhances Chemosensitivity in Ovarian and Pancreatic Cancer

Materials and Methods

Generation of Antibody-Producing Hybridomas

Immunization and hybridoma generation procedures were conducted using established protocols (Hu et al., 2014; Qin et al., 2018; Voo et al., 2013). Briefly, two 6-week-old female BALB/c mice were immunized once every 3 days with the MFAP5 protein (GenScript USA, Inc.) by five 20 μL injections of each of the solutions emulsified with adjuvant into the footpad. After the fifth injection, serum samples were obtained from both mice to confirm by ELISA, the presence of serum antibodies against the target. Extra boosts were administered as required. Popliteal lymph nodes from the immunized mice were harvested around Day 20, and lymph cells were fused with Sp2/0 myeloma to establish hybridomas, plated under selection media (HAT). Screening for selection of positive clones against the protein, was performed by ELISA using an irrelevant protein as negative control. After selection of hybridoma candidates master cells, MAbs were purified using MabSelect SuRe antibody purification resin (GE Healthcare) and eluted with low pH Ag/Ab elution buffer. Validation and quality control tests of purified antibody: specificity (binding screening by ELISA), purity (SDS-PAGE), endotoxin (Lonza Endotoxin kit) and isotype (ELISA Sigma) were conducted following recommendations of Rigor and reproducibility by International Working Group for Antibody Validation (Uhlen et al., 2016).

Anti-MFAP5 Antibody "130A" Suppressed In Vivo Ovarian Tumor Growth

To determine the inhibitory effects of anti-MFAP5 monoclonal antibodies on ovarian tumor progression in vivo, $3\times10^6$ luciferase-labeled OVCA432 cells were intraperitoneally injected into nude mice. One week after tumor cell injection, mice were randomized into the treatment and control groups (12 mice/group). They were injected twice weekly with 15 mg/kg anti-MFAP5 antibody clone 130A or 15 mg/kg control normal mouse IgG, respectively, for a total of 6 weeks. Tumor progression was monitored using an IVIS 200 bioluminescence/fluorescence imaging system. To determine the effect of the anti-MFAP5 antibody on intratumoral microvessel leakiness, 100 μL of 10 mg/mL FITC-dextran (relative molecular mass, 200,000 Da; Sigma-Aldrich) was injected via the tail vein into mice before the mice were sacrificed. Tumor weights were recorded, and 6-μm frozen tissue sections were prepared from tumors harvested using a CM1850 cryostat (Leica Microsystems). FITC-dextran signals were quantified by fluorescent microscopy.

Anti-MFAP5 Antibody "130A" Increased Paclitaxel Bioavailability in Ovarian Tumors Nude mice were intraperitoneally injected with $3\times10^6$ luciferase-labeled OVCA432 cells. One week after cancer cell injection, tumor-bearing mice were intraperitoneally injected with 15 mg/kg isotype control mouse IgG or anti-MFAP5 antibody clone 130A twice weekly for a total of 4 weeks. One dose of Oregon green-conjugated paclitaxel (1 mg/kg; Life Technologies) was injected via the tail vein using sterile PBS as vehicle into both MFAP5-targeting monoclonal antibody treated and control IgG treated animals 1 hour before they were sacrificed. At the experimental endpoint, tumor weights were recorded, and 6-μm frozen tissue sections were prepared from tumors harvested using a CM1850 cryostat. Oregon Green 488 signals were quantified by fluorescent microscopy and the amount of fluorophore conjugated paclitaxel in the tumor tissue samples was then compared between the two group of mice. While evaluation of the tumor suppressive effect of paclitaxel was not one of the aims of this study, it is worth noting that it has been reported that linking Oregon green to paclitaxel increases the polarity of the drug and reduces its toxicity (Uhlen et al., 2016).

Immunohistochemical Analysis

Immunolocalization of MFAP5 was performed on a FFPE pancreatic tumor tissue array, which contains samples from 91 patients (HPan-Ade170Sur-01; US Biomax, Inc.) using a commercially available anti-MFAP5 (1:500, HPA010553; Sigma-Aldrich) antibody. MFAP5 expression was visualized using a Betazoid 3,3'-diaminobenzidine chromogen kit (Biocare Medical). For tumor samples obtained from mice, immunolocalization of CD34 (1:100, GTX28158; GeneTex) was performed. Stromal MFAP5 expression and $CD34^+$ microvessel density was quantified as previously described (Leung et al., 2014; Leung et al., 2018).

Statistical Analysis

The SPSS 20 (IBM Corporation) and Prism 7.0 (GraphPad Software) software programs were used to perform statistical tests. All in vitro studies were repeated independently in triplicate. A two-tailed Student's i-test was used to determine differences in sample means for data with normally distributed means. The Mann-Whitney U test was used for analysis of nonparametric data. P-values less than 0.05 were considered statistically significant.

Results

Development and Characterization of Anti-MFAP5 Mabs

Figure 7A:
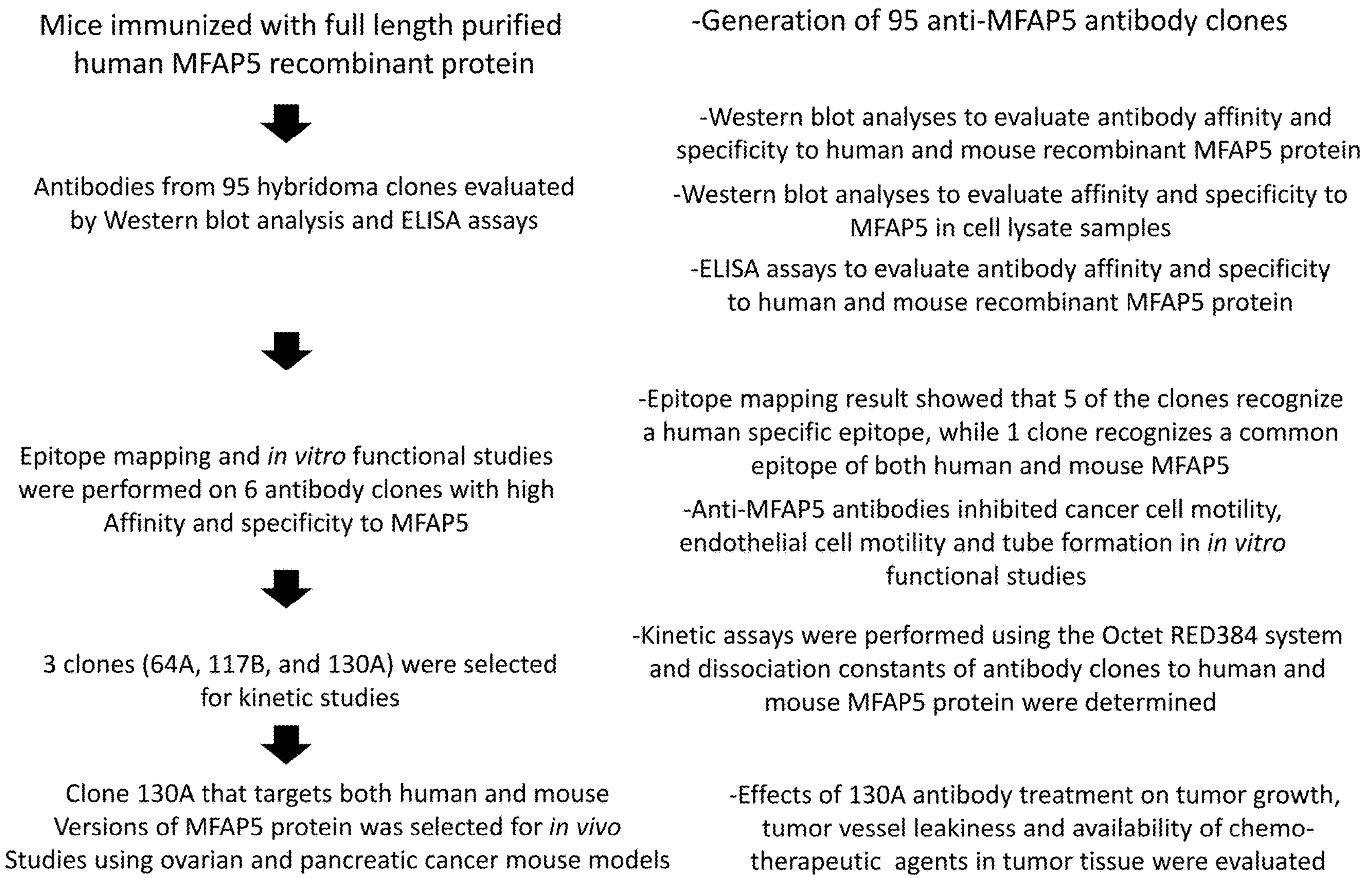
Figure 7B:
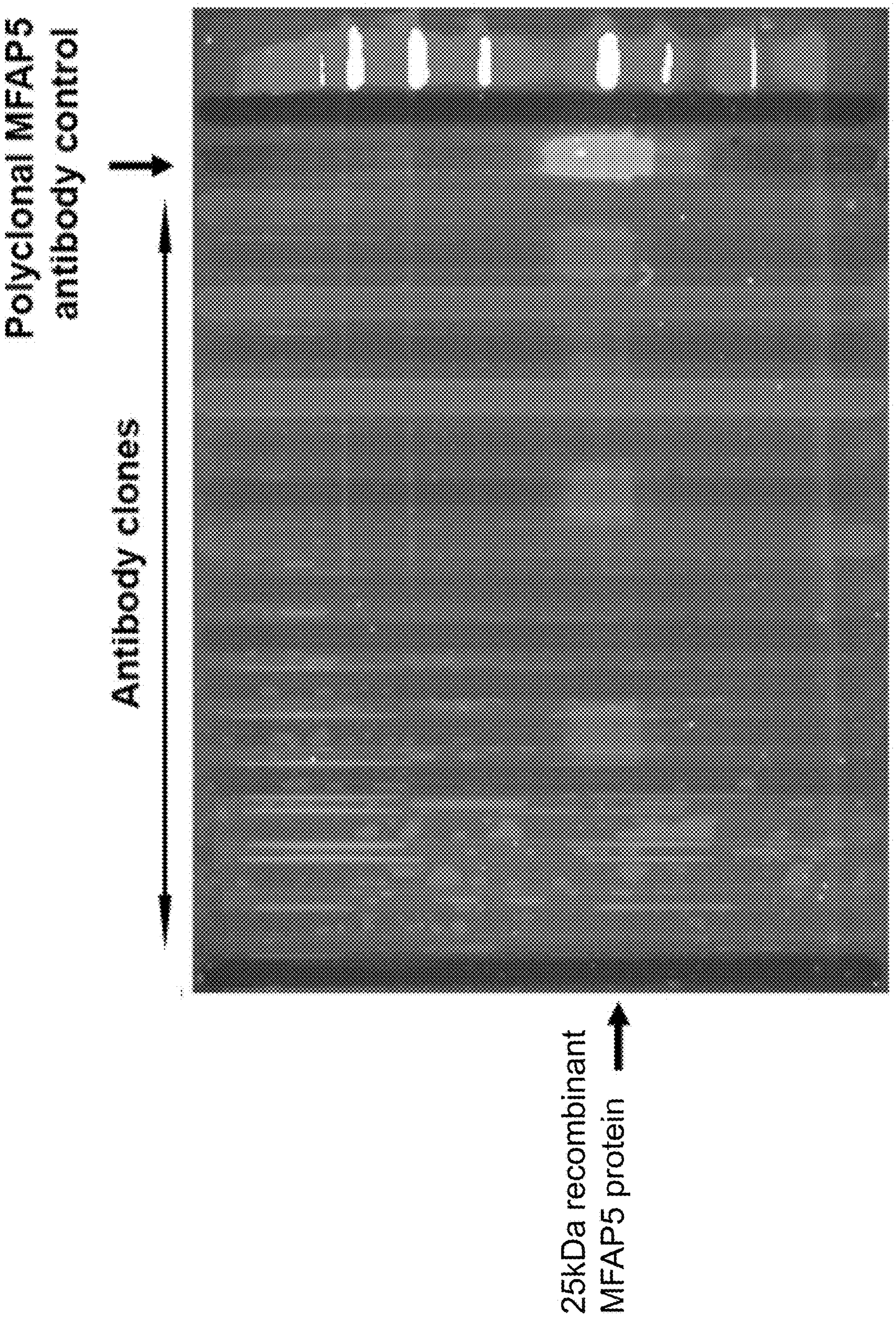
Figure 7D:
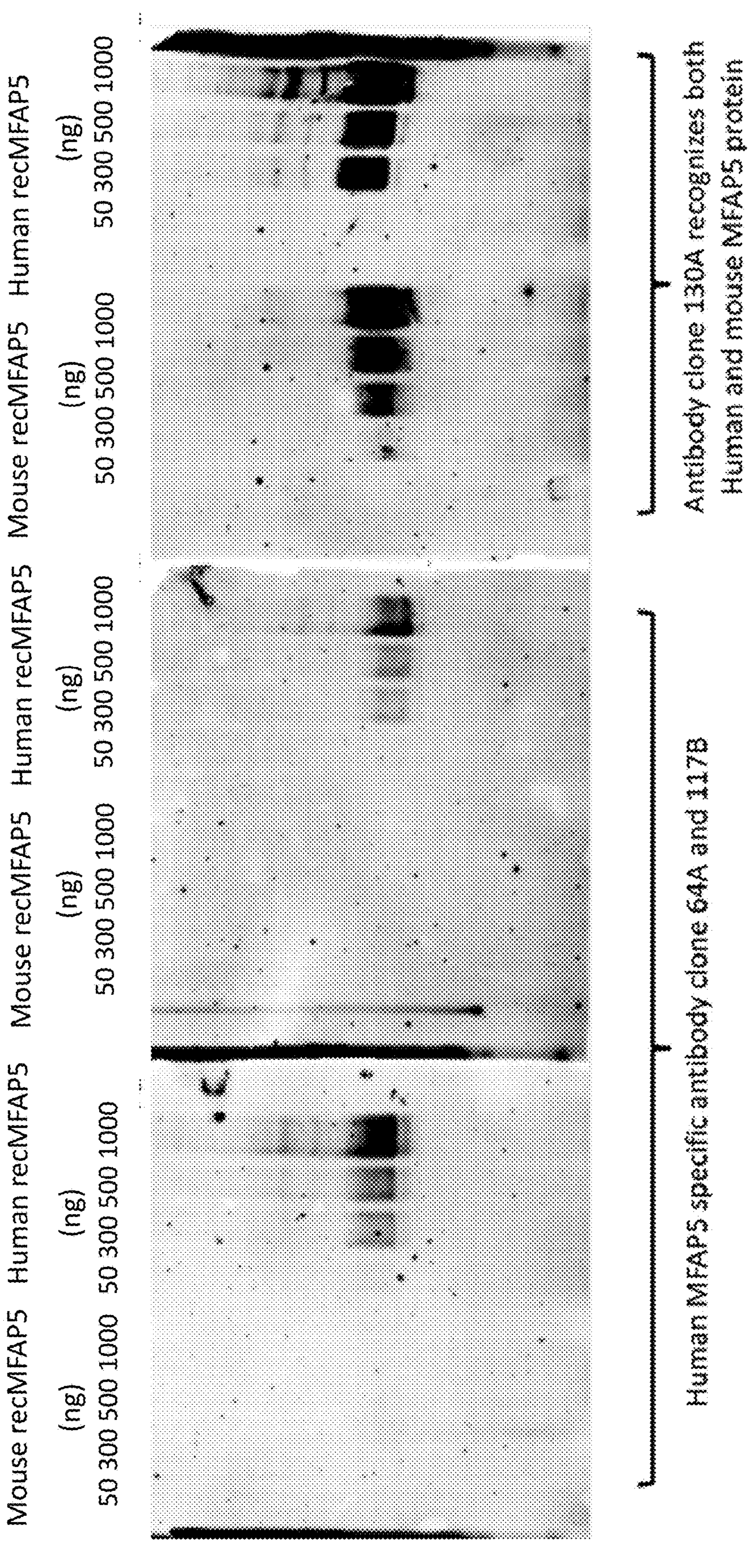

Previous studies showed that down-regulation of endogenous MFAP5 in CAFs suppressed ovarian tumor growth and angiogenesis (Leung et al., 2014; Leung et al., 2018), suggesting that targeting CAF-derived MFAP5 may be a new modality in ovarian cancer treatment. Since MFAP5 is a secretory protein, the inventors tested whether blocking MFAP5 using an immunological approach could inhibit tumor growth. First, MFAP5-targeting monoclonal antibodies were developed using purified full-length human MFAP5 recombinant protein (recMFAP5) as an antigen to immunize mice (FIG. 7A). Using an enzyme-linked immunosorbent assay, 95 positive hybridoma clones were identified, which generated MAbs that could bind to human recMFAP5. Western blot analysis using a Bio-Rad multiscreen apparatus was performed to identify antibody clones that had strong binding affinity for human MFAP5 (FIG. 7B). Epitope mapping performed on six of these clones (50B, 52B, 64A, 75B, 117B and 130A). Three candidates (antibody clones 64A, 117B and 130A), which have the highest affinity and specificity to MFAP5 protein, were chosen for further studies. Epitope mapping results showed that clone 64A and 117B recognized the same human MFAP5 protein sequence (DETVLAVLA) (SEQ ID NO:3), while clone 130A was specific to a consensus peptide sequence (LCRQMAGLPPRR) (SEQ ID NO:4) common for both human (SEQ ID NO:1) and murine MFAP5 proteins (SEQ ID NO:2) (see FIG. 7C, FIG. 12A, and FIG. 12B). The specificity of each anti-MFAP5 antibody clone was further validated by Western blot analysis (FIG. 7D).

Figure 7E:
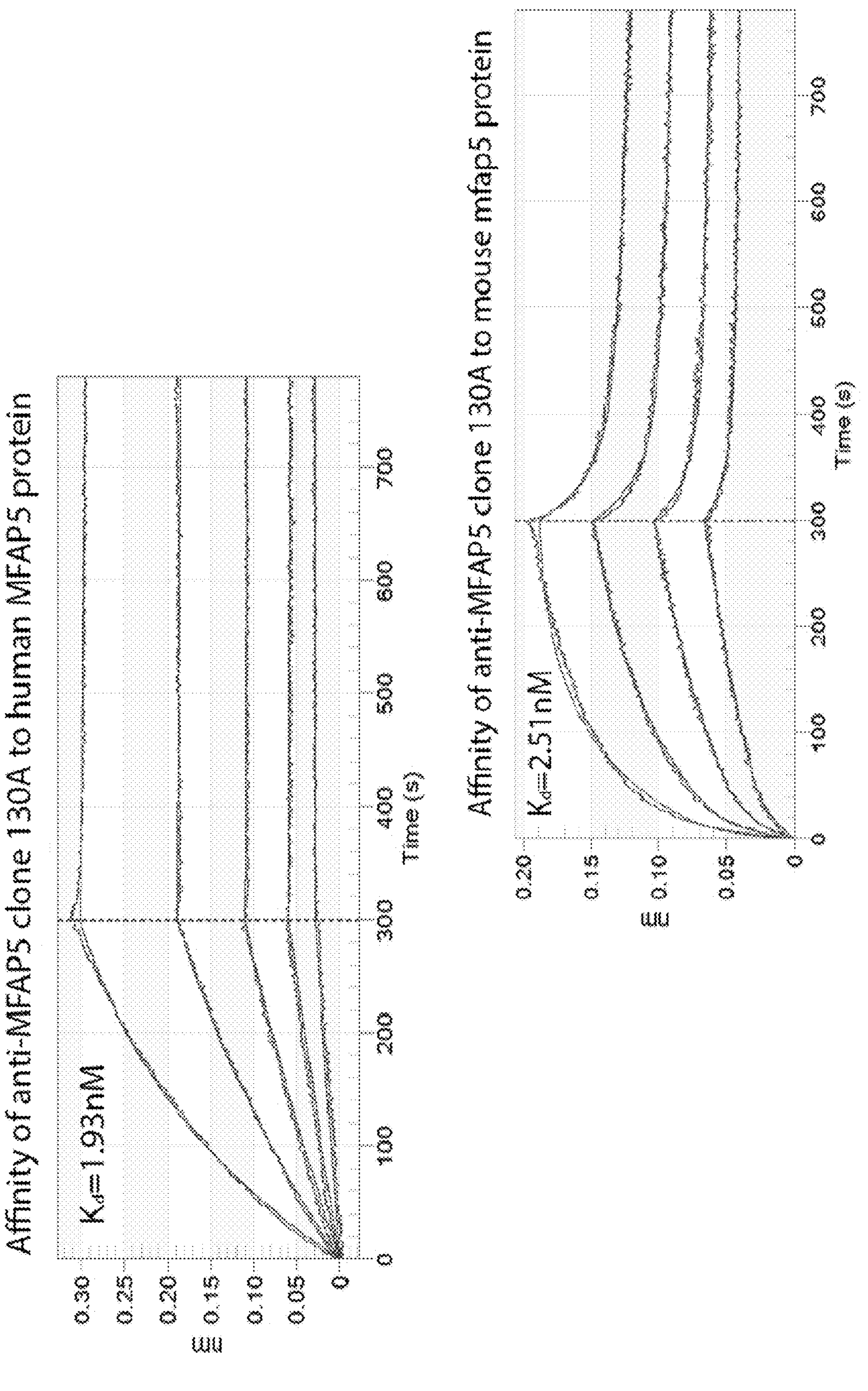
Figure 12C:
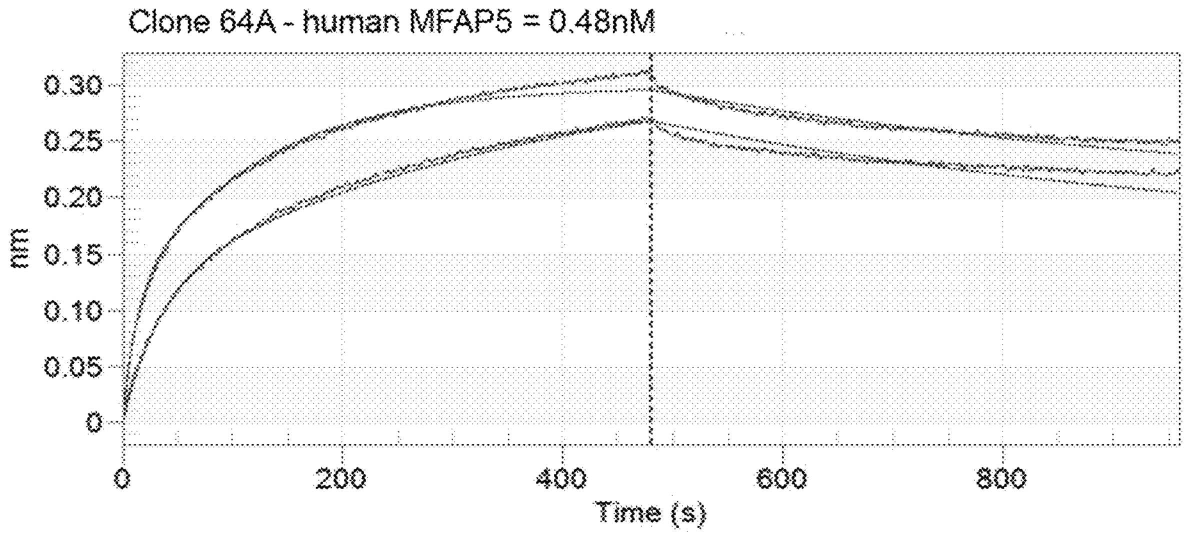
Figure 12D:
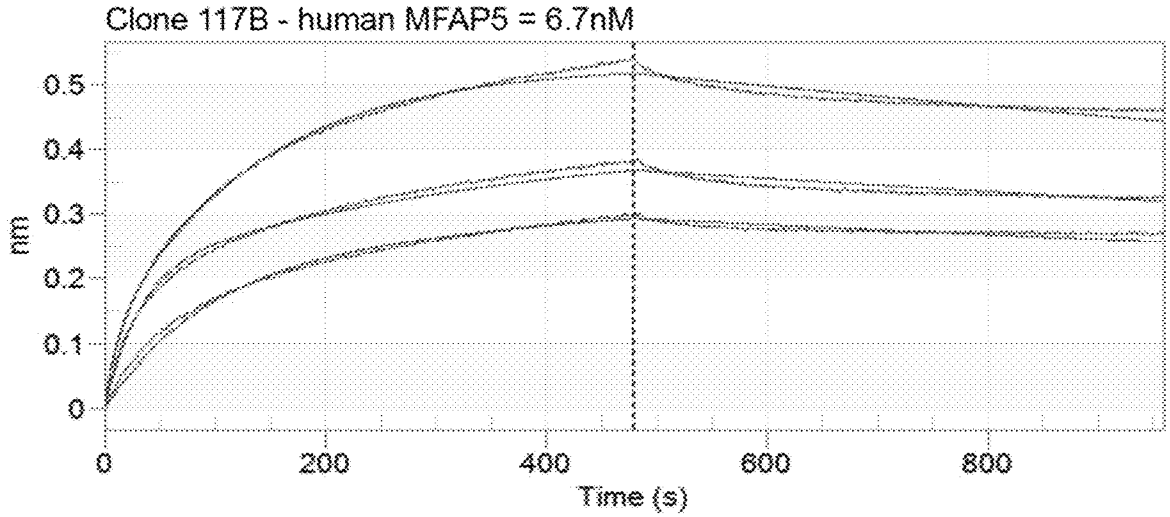

Focusing on the three antibody clones, binding kinetics experiments were performed using the Octet RED384 system (Pall ForteBio LLC). Kinetic assays showed that the dissociation constant ($K_d$) of clone 130A for human and mouse MFAP5 protein were 1.93 nM and 2.51 nM, respectively, suggesting that clone 130A has high binding affinity to both human MFAP5 and mouse MFAP5 protein (FIG. 7E). On the other hand, the dissociation constant ($K_d$) of clone 64A and 117B for human MFAP5 protein was 0.48 nM and 6.7 nM, respectively (see FIG. 12C and FIG. 12D).

Figure 7F:
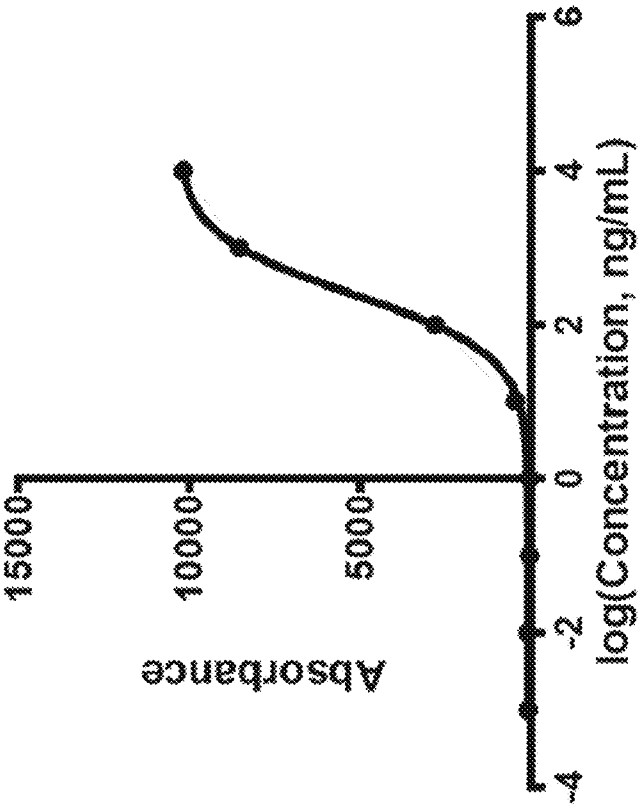
Figure 7G:
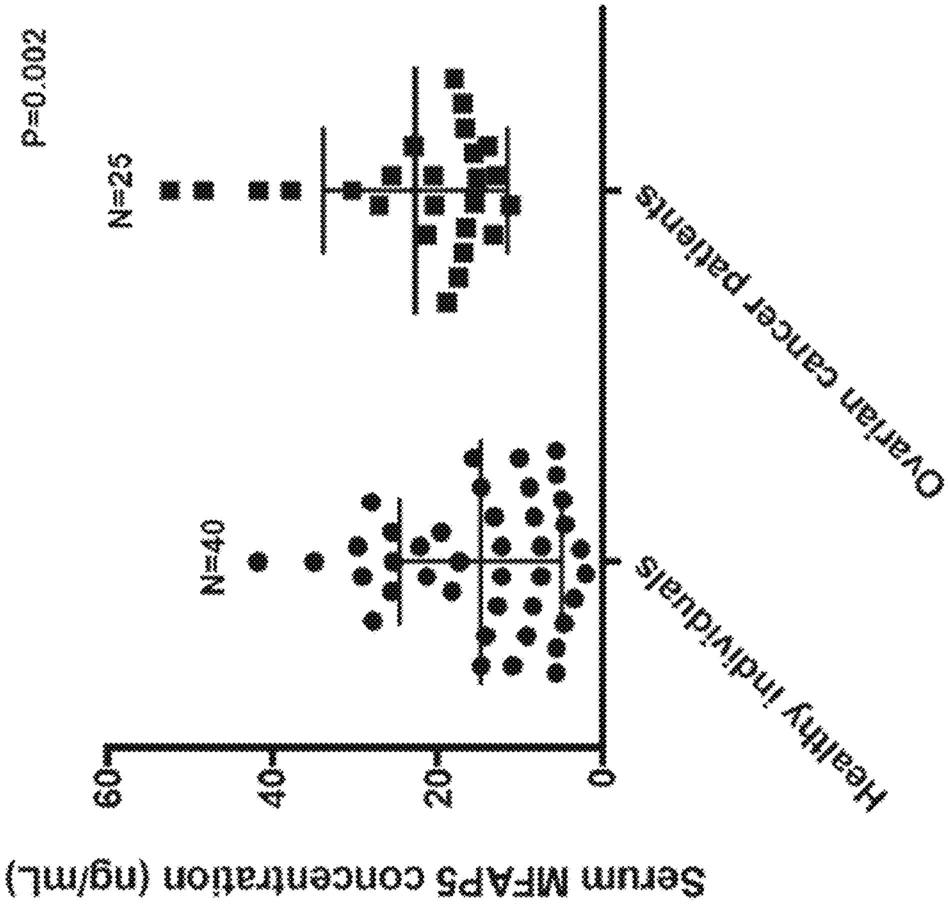

To determine whether the antibody recognized native secretory MFAP5, ELISAs using 130A antibody (FIG. 7F) were performed on serum samples obtained from healthy individuals and pre-operative age-matched patients with advanced stage high grade serous ovarian cancer. The results showed that serum samples obtained from cancer patients had significantly higher levels of MFAP5 than the serum from healthy individuals (FIG. 7G). These data suggested that MFAP5 was a tumor-associated antigen, and that circulating MFAP5 could be detected by the 130A anti-MFAP5 antibody.

Figure 8B:
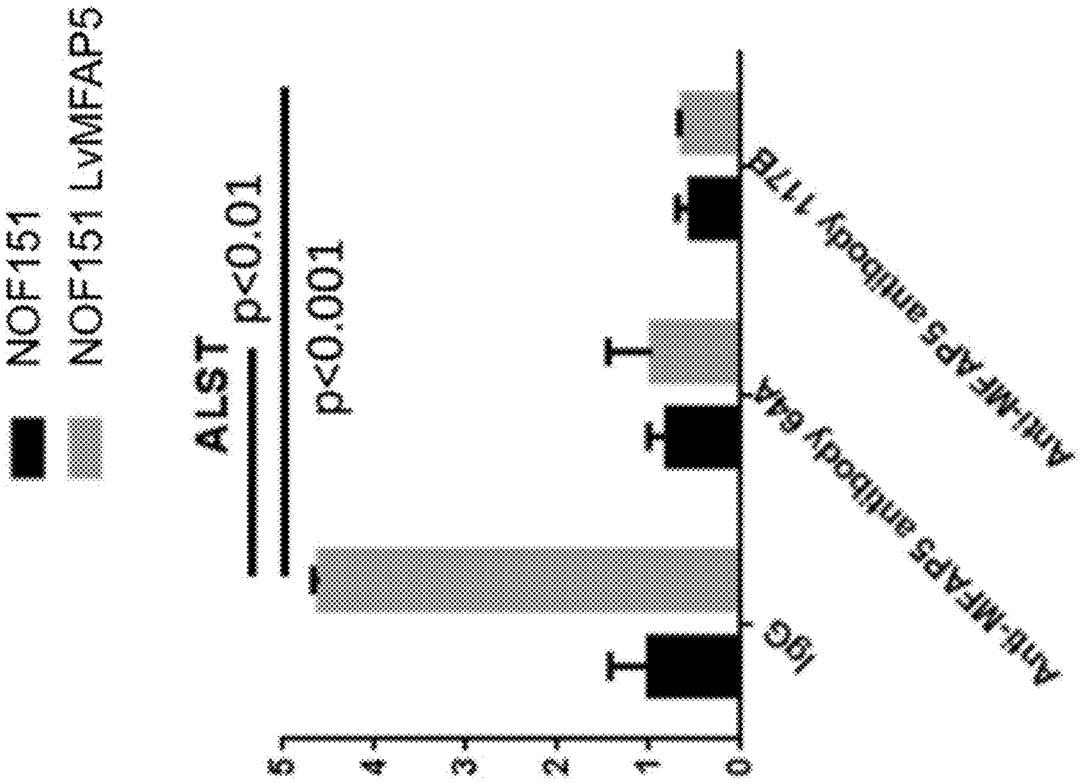
FIG. 8A, FIG. 8B, FIG. 8C, FIG. 8D, FIG. 8E, FIG. 8F, and FIG. 8G show anti-MFAP5 antibody suppresses cancer cell and endothelial cell motility in vitro.
Figure 8A:
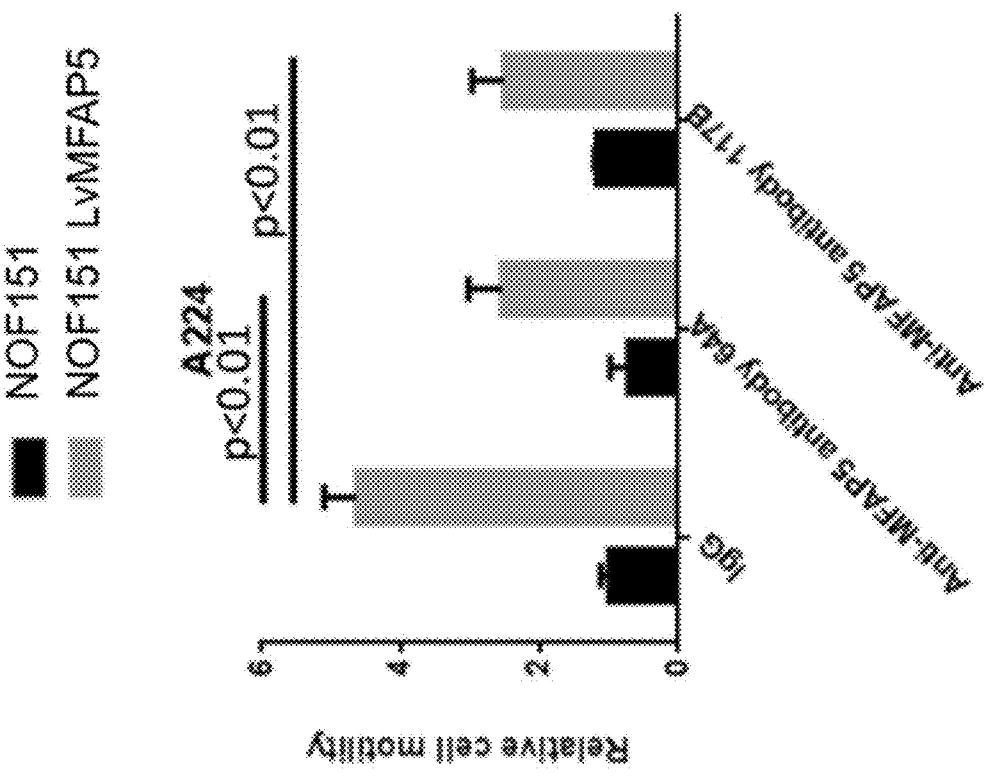
Figure 13:
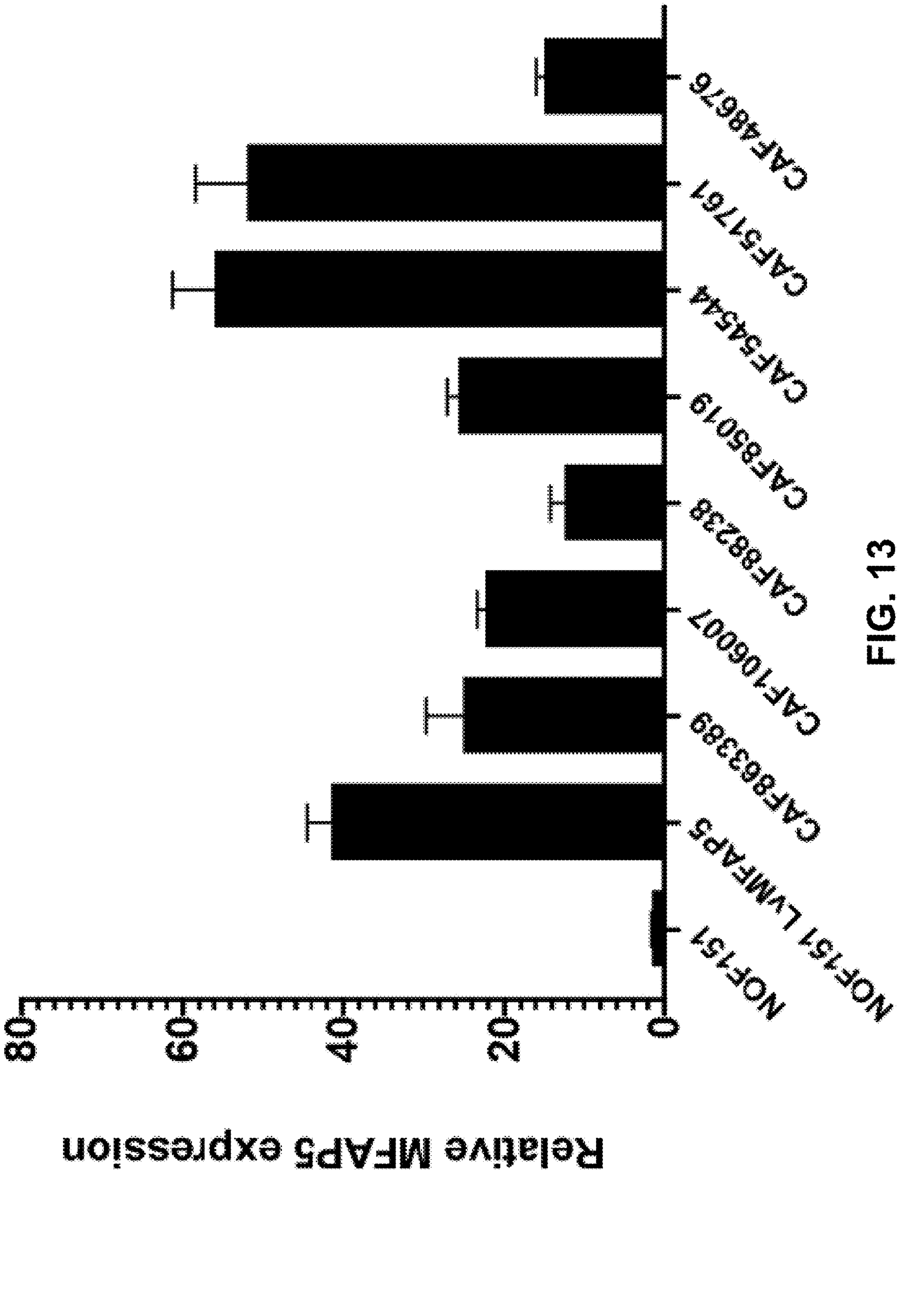
FIG. 13 shows characterization of MFAP5 overexpression ovarian fibroblast line NOF151 LvMFAP5. Quantitative real-time PCR analysis on NOF151, NOF151 LvMFAP5 and seven primary CAF cultures showed that MFAP5 expression level of NOF151 LvMFAP5 was approximately 40 times higher than its parental line NOF151 and was comparable to the primary CAF cultures tested (Range=12.44-55.99 times higher than NOF151; Mean=29.78 times higher than NOF151; Standard deviation=17.30)

Anti-MFAP5 Antibody Suppresses Ovarian Cancer Cell and Endothelial Cell Motility In Vitro To determine the biological effector functions of monoclonal anti-MFAP5 antibodies, the effects of antibody clones 64A, 117B and 130A on ovarian tumor motility and angiogenesis were determined. In Boyden chambers, A224 and ALST human ovarian cancer cells were co-cultured with ovarian fibroblasts NOF151 transfected with MFAP5 or the control vector. Cancer cell motility was determined in the presence of 64A and 117B antibody or control IgG. The results showed that ovarian cancer cells co-cultured with ovarian fibroblasts transfected with MFAP5 had a significant higher motility potential than the mock transfectant did, and the motility promoting effect of MFAP5 was abrogated in the presence of the monoclonal MFAP5-blocking antibodies but not the isotype control (FIG. 8A and FIG. 8B). MFAP5 expression of MFAP5 transfected NOF151 cells is comparable to that of primary CAF cultures (FIG. 13). These data suggest that the MFAP5-blocking antibodies developed effectively suppressed the effect of CAF-derived MFAP5 on ovarian cancer cell motility in vitro.

Figure 8D:
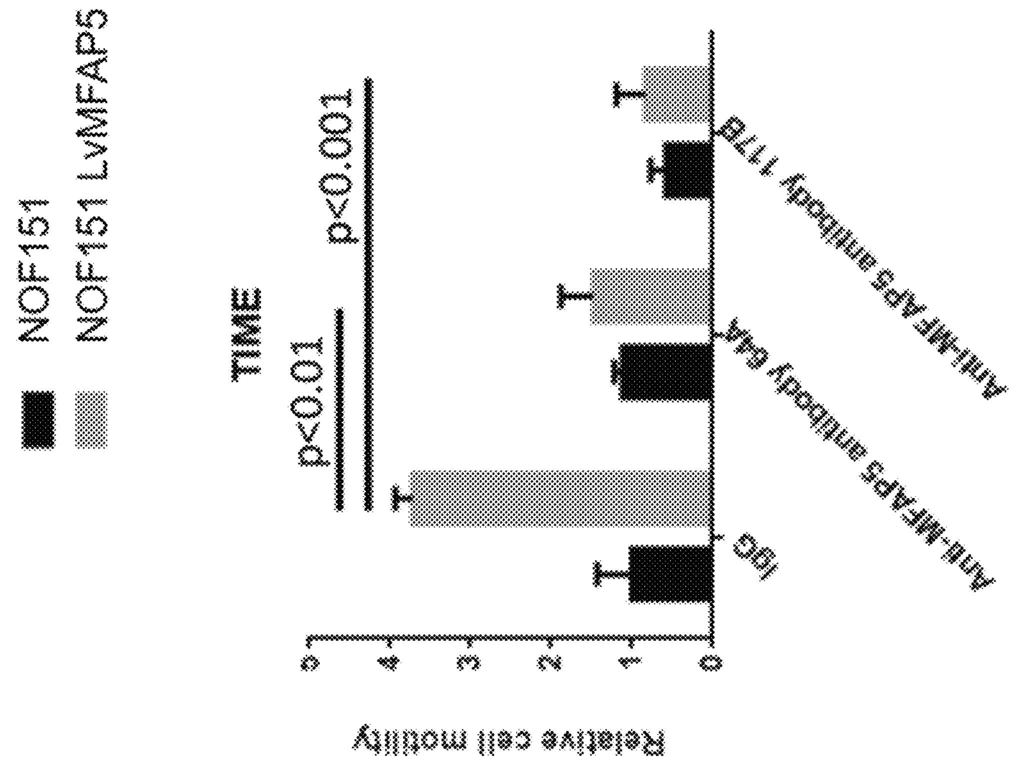
Figure 8C:
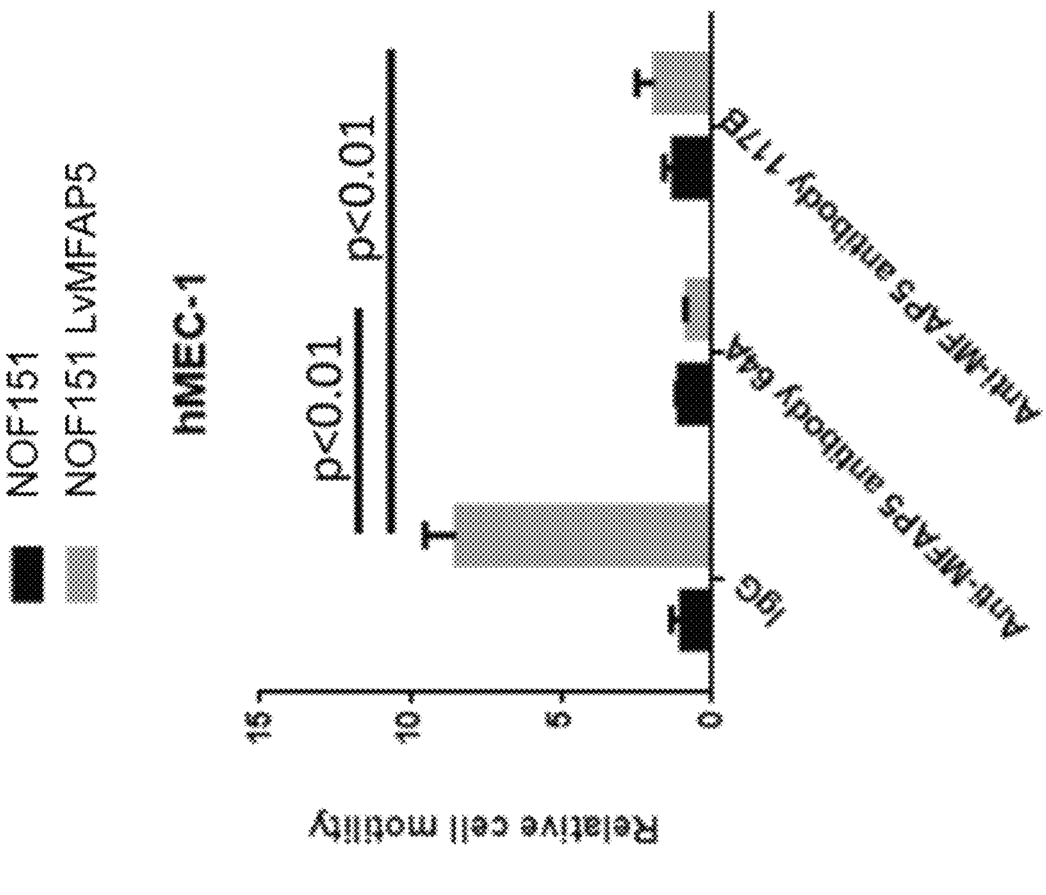
Figure 8E:
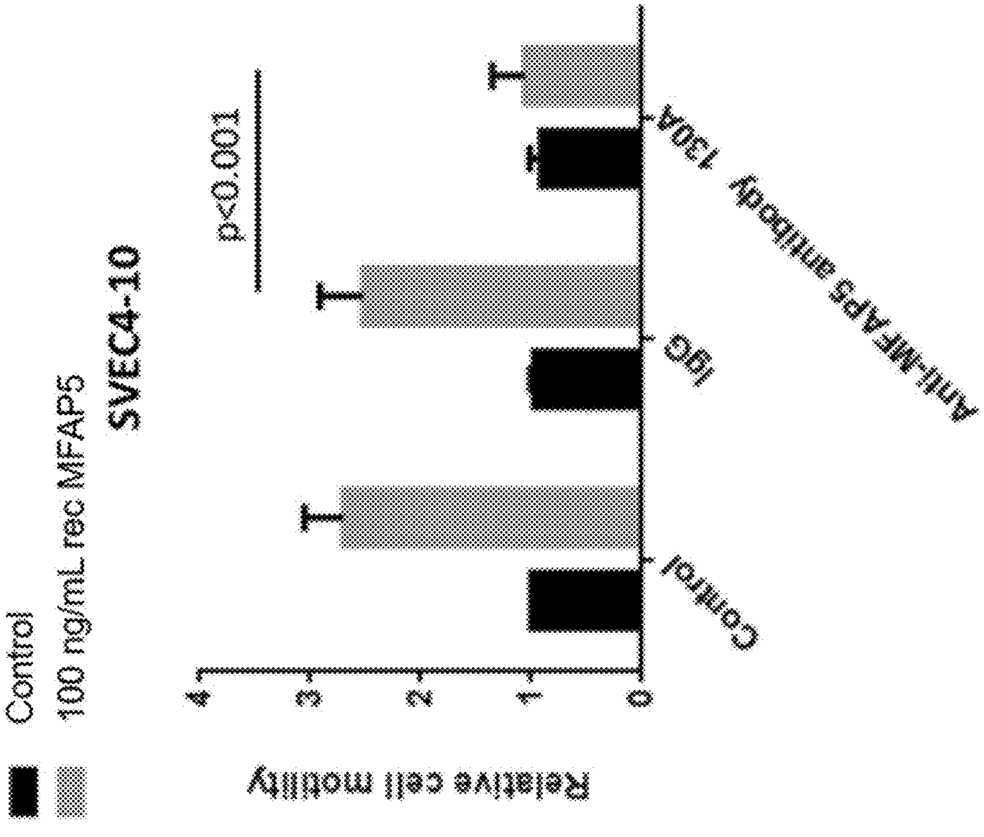

Besides the anti-motility effect on cancer cells, the anti-angiogenic effect of antibody clone 64A and 117B was determined. Human microvascular endothelial cells hMEC-1 and TIME were co-cultured with CAFs transfected with MFAP5 or the control vector and cell motility was determined in the presence MFAP5-blocking antibodies or control IgG. The results showed that hMEC-1 and TIME cells co-cultured with CAFs transfected with MFAP5 had a significant higher cell motility potential than the mock transfectant, and the effect was abrogated in the presence of 64A and 117B antibodies but not by the control IgG (FIG. 8C and FIG. 8D). In addition, for MAb clone 130A, which also recognizes and binds murine MFAP5, motility assays were performed on SVEC4-10 mouse endothelial cells treated with recombinant mouse MFAP5 protein in the presence of 130A antibody or the control IgG. The results showed that SVEC4-10 cells treated with recombinant mouse MFAP5 had significantly higher motility rates than those in the control buffer alone, and that the effect was abrogated in the presence of 130A antibody but not by the control IgG (FIG. 8E). These data suggested that the MFAP5-blocking antibodies suppressed human and mouse endothelial cell motility in vitro.

Anti-MFAP5 Ab Suppresses Pancreatic Cancer Cell Motility In Vitro

Figure 14A:
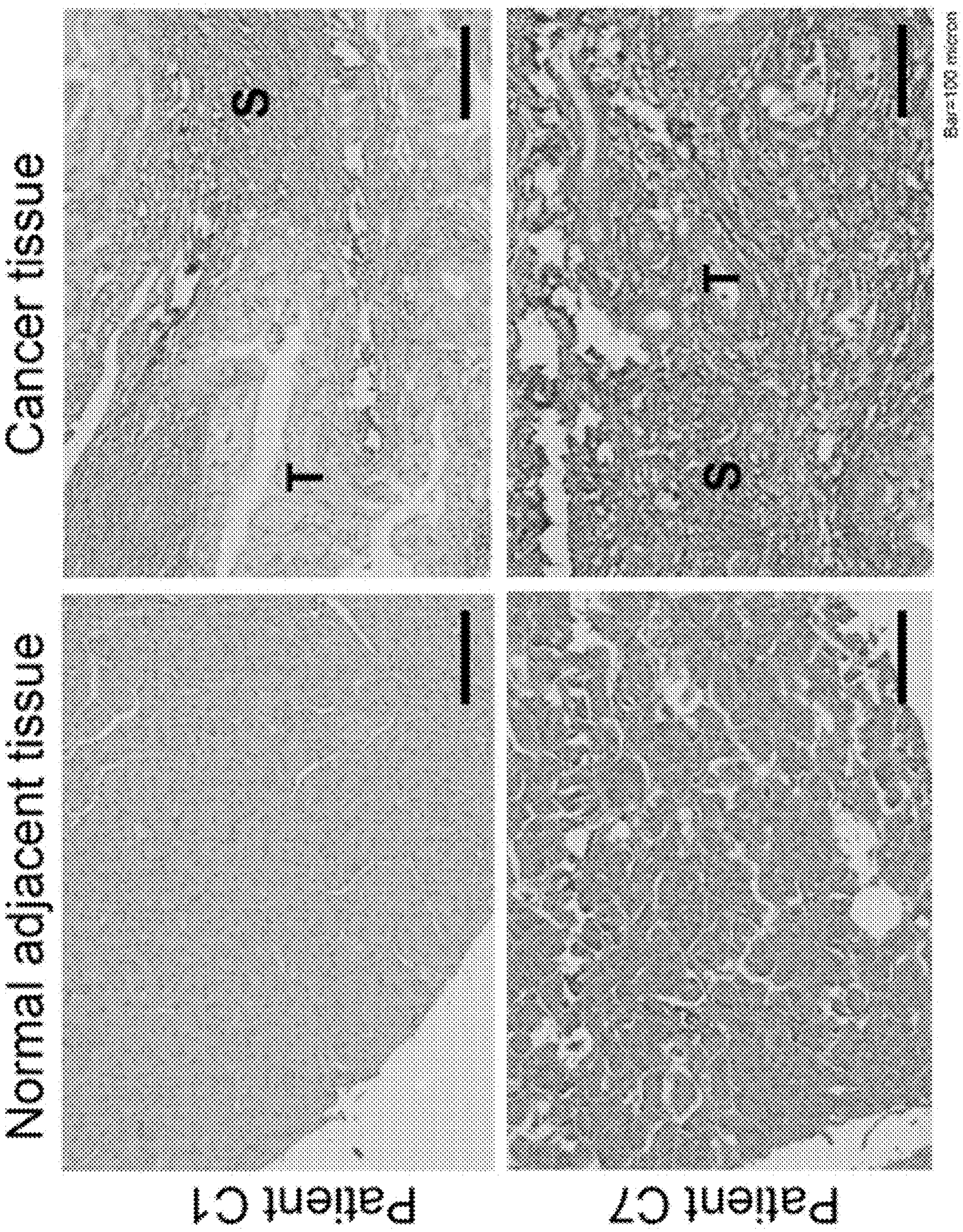
FIG. 14A and FIG. 14B show prognostic significance of stromal MFAP5 expression in pancreatic ductal adenocarcinoma.
Figure 14A:
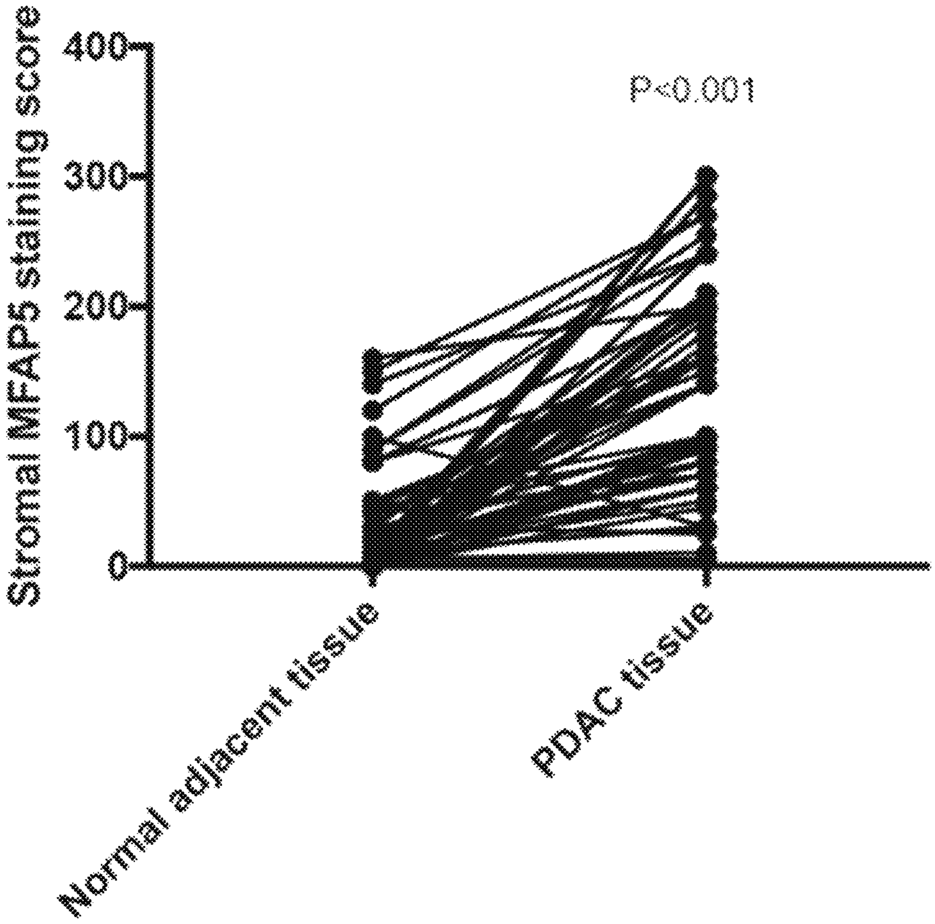
Figure 14B:
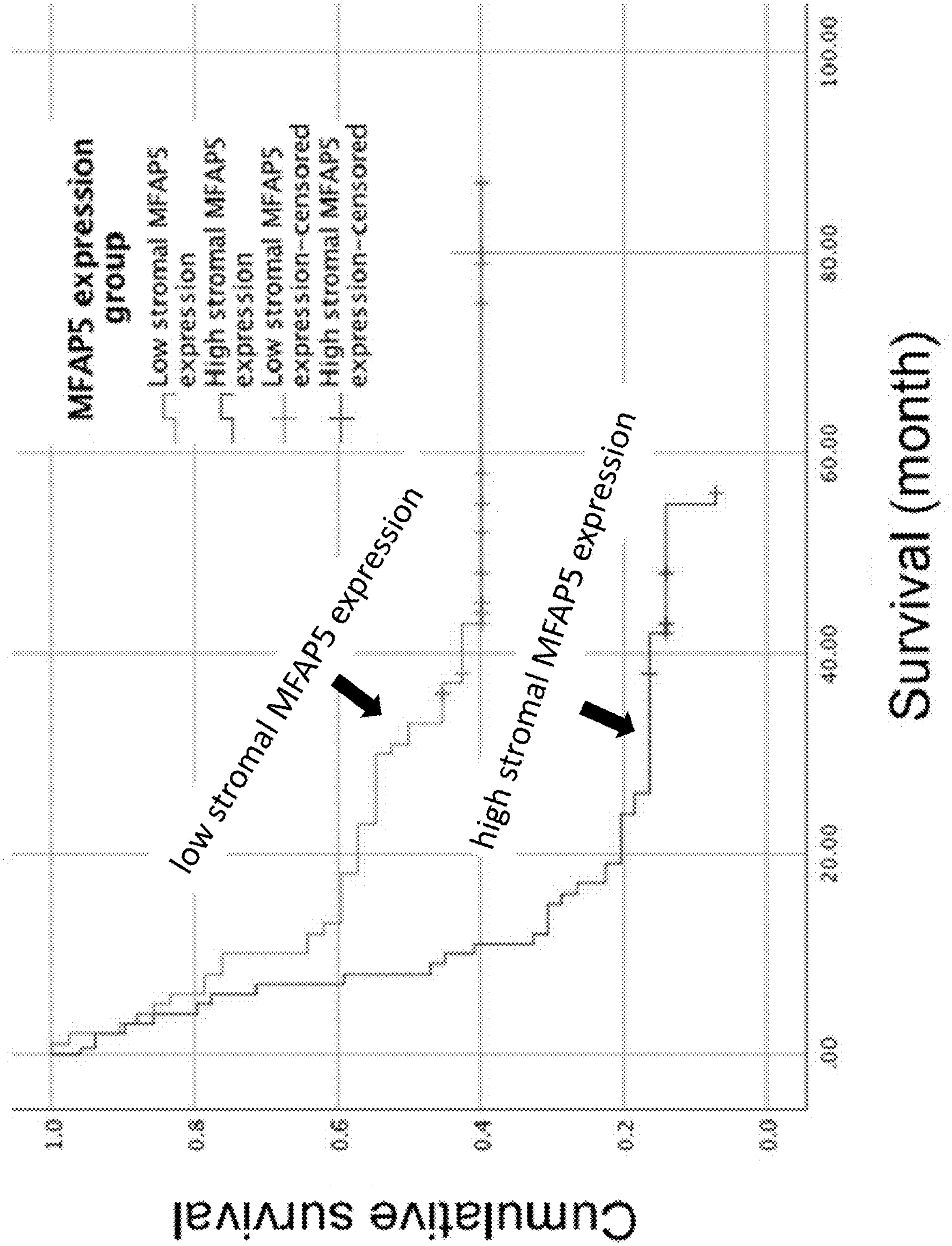

It was previously shown that MFAP5 expression levels were markedly higher in ovarian CAFs than in normal ovarian fibroblasts, and high stromal MFAP5 protein levels correlated with reduced survival in ovarian cancer patients (Leung et al., 2014; Leung et al., 2018). To evaluate the feasibility of applying MFAP5-targeting therapeutic agent as a treatment regimen for pancreatic ductal adenocarcinoma (PDAC), a type of cancer which is often supported and protected by the dense stromal component (Ohlund et al., 2017), immunostaining was performed on tumor tissue samples and the corresponding normal adjacent tissue samples obtained from 64 PDAC patients. Staining results suggested that while the majority of normal adjacent tissue was negative for MFAP5 expression, expression levels of MFAP5 was significantly higher in pancreatic CAFs ($P<0.001$) (FIG. 14A). In addition, survival analysis and log-rank test showed that high stromal MFAP5 expression in patients with PDAC is significantly associated to the reduction of overall survival duration ($N=91$, $P<0.001$) (FIG. 14B). Cox survival analysis adjusted with age and sex showed that high stromal MFAP5 expression in PDAC has a hazard ratio of 2.79 ($N=91$, $P<0.001$). These results indicated that the use of anti-MFAP5 antibody in the treatment of PDAC could be beneficial.

Figure 8F:
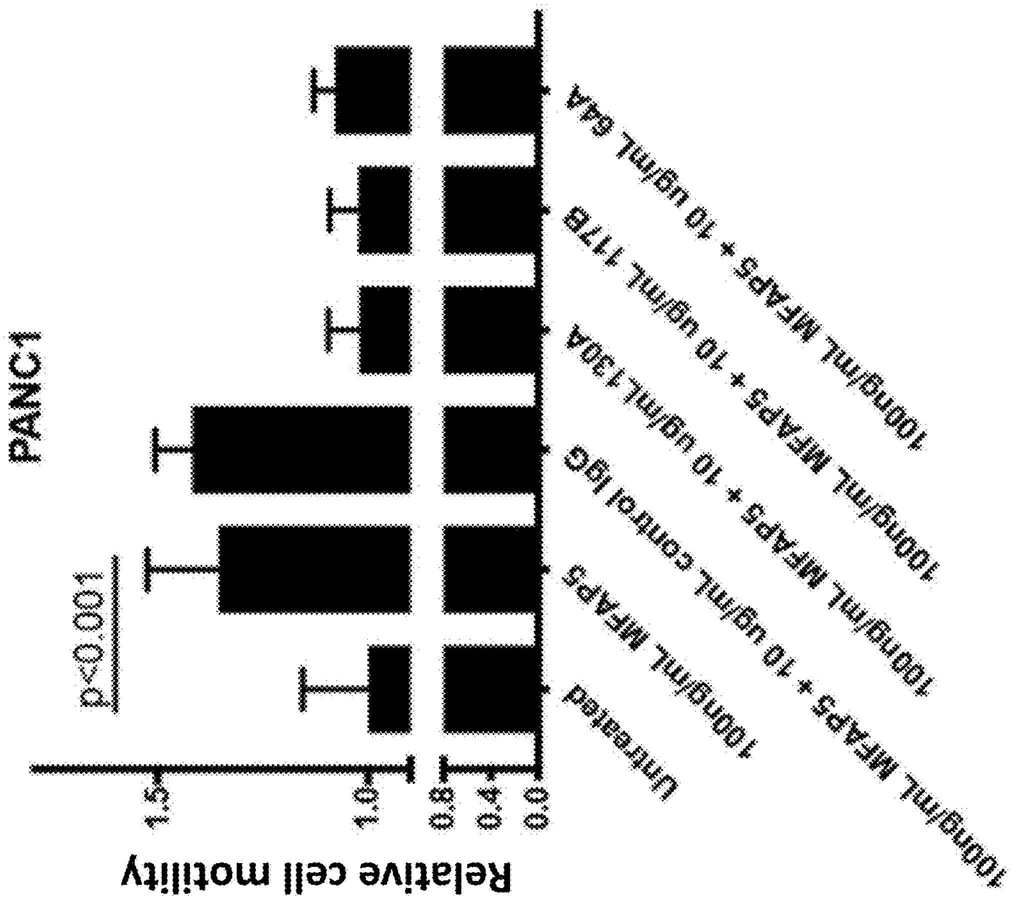
Figure 8G:
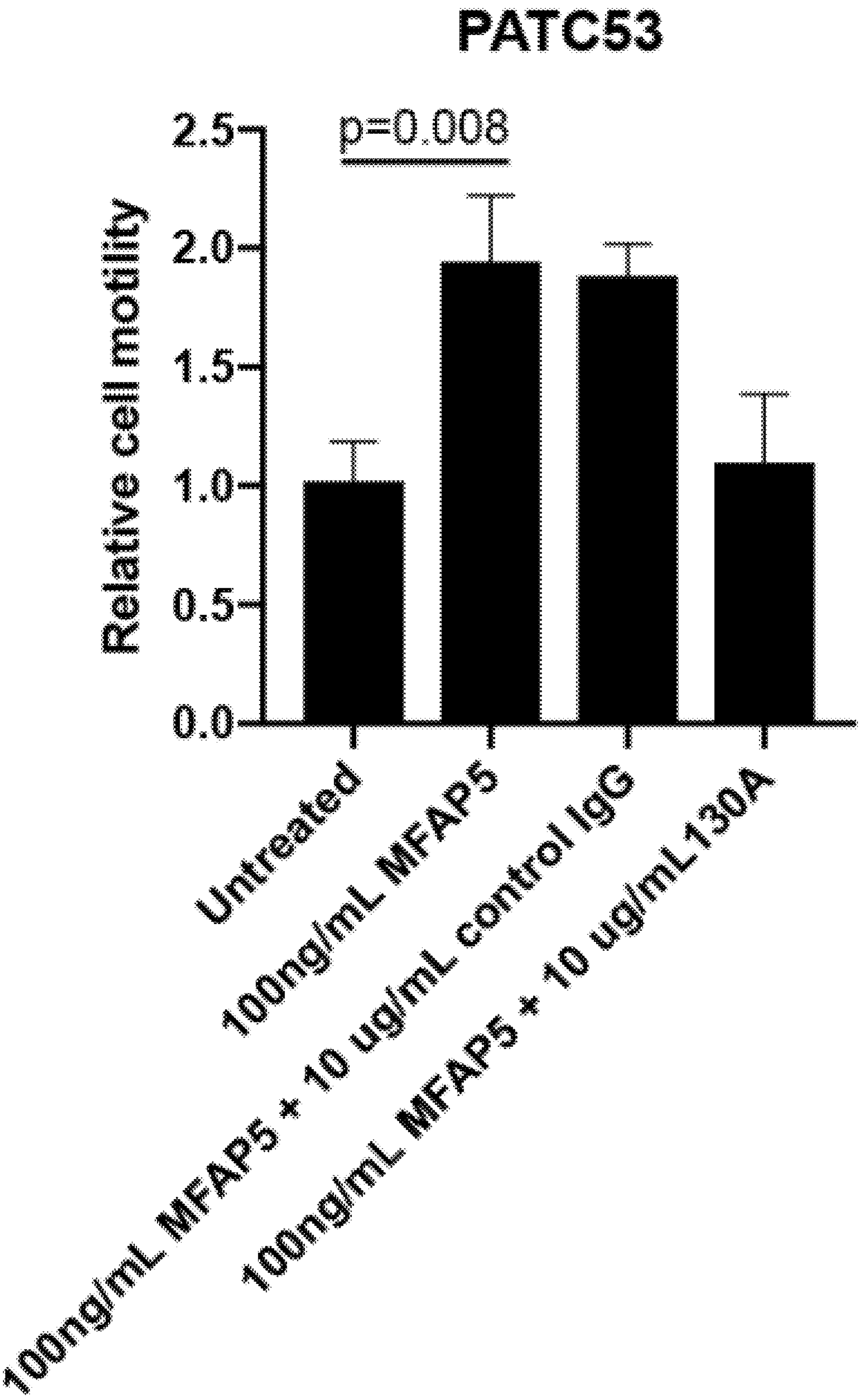

To evaluate the inhibitory roles of monoclonal anti-MFAP5 antibodies on PDAC cell in vitro, the effect of antibody clones 64A, 117B and 130A on PDAC cell motility was determined. In Boyden chambers, PANC1 human pancreatic cancer cells were treated with recombinant MFAP5 protein and antibodies, and cancer motility was determined by the number of cells that migrated through the porous membrane. Motility assay results showed that ovarian cancer cells treated with MFAP5 had a significant higher motility than untreated cells, and the motility promoting effect of MFAP5 was abrogated in the presence of the anti-MFAP5-blocking antibodies but not by the control IgG (FIG. 8F). Similarly, for PDAC PDX cell line PATC53, which was derived from a pancreatic cancer patient harboring a KRAS G12D mutation and a p53 R306* mutation, treatment with recombinant MFAP5 increased cancer cell motility, and the motility promoting effect of MFAP5 was abrogated in the presence of the anti-MFAP5-blocking antibody but not by the control IgG (FIG. 8G).

Anti-MFAP5 Antibody Suppresses Tumor Growth In Vivo

Figure 9A:
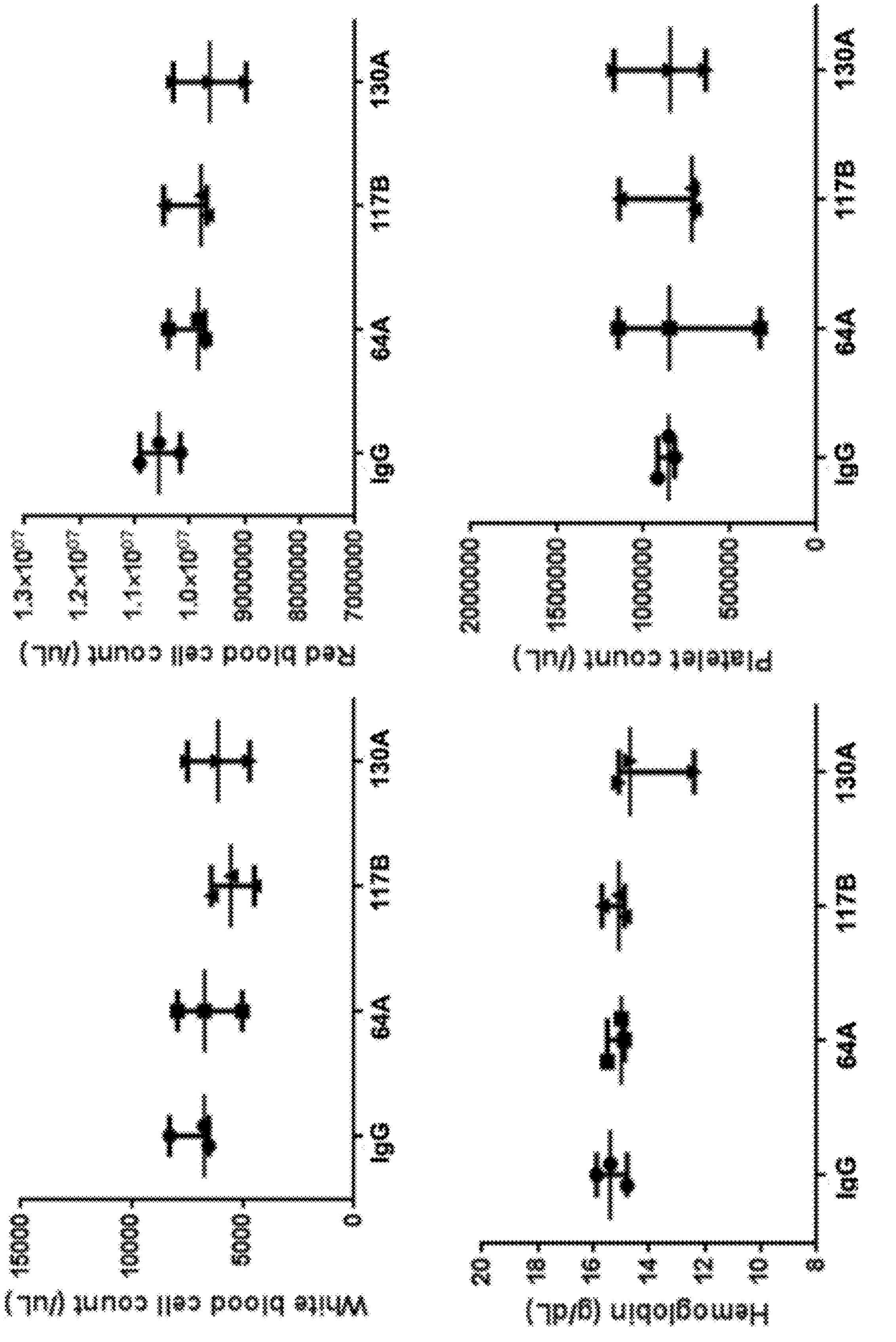
FIG. 9A, FIG. 9B, and FIG. 9C show toxicity analysis of therapeutic anti-MFAP5 monoclonal antibodies using animal models of ovarian cancer.
Figure 9B:
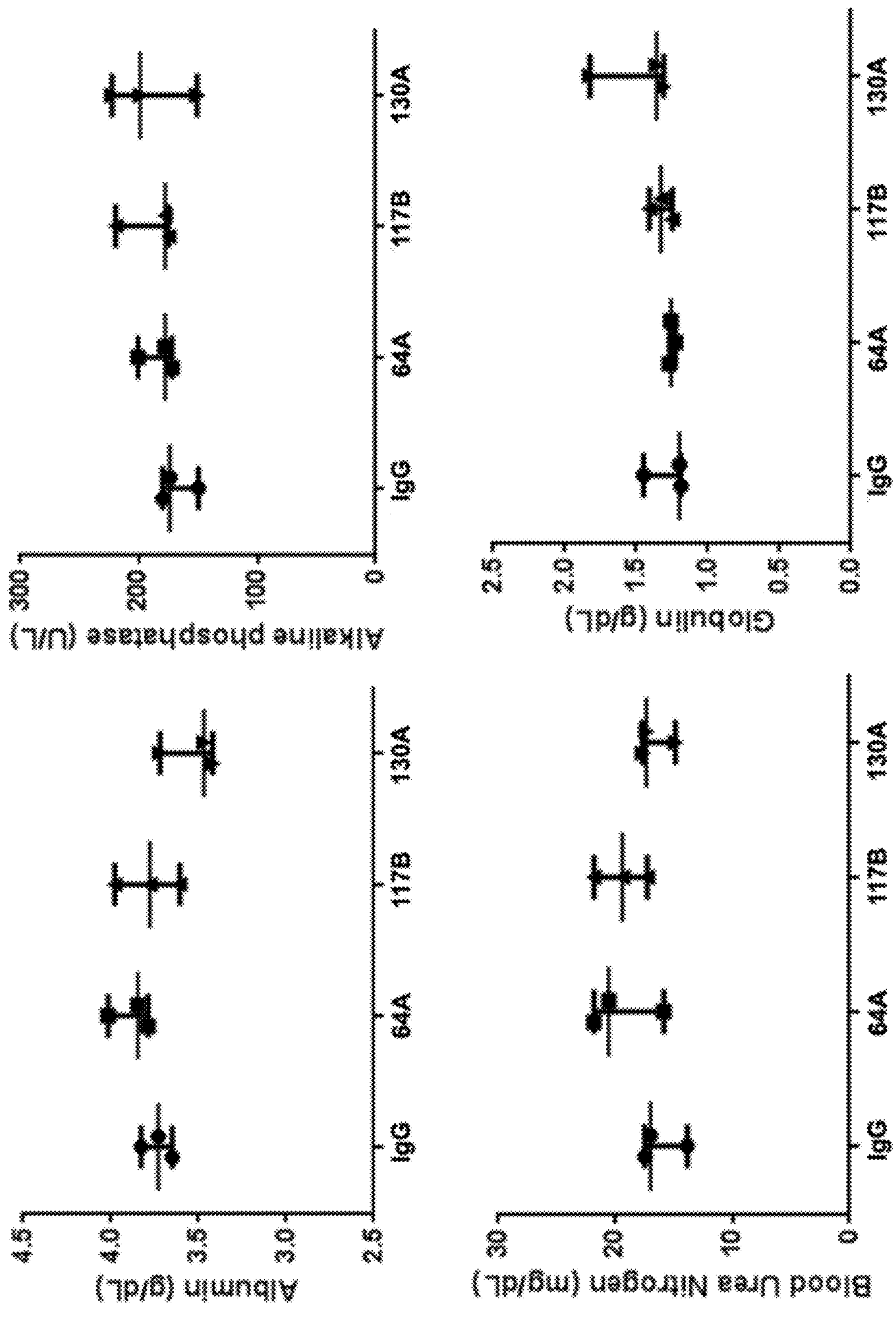
Figure 9B:
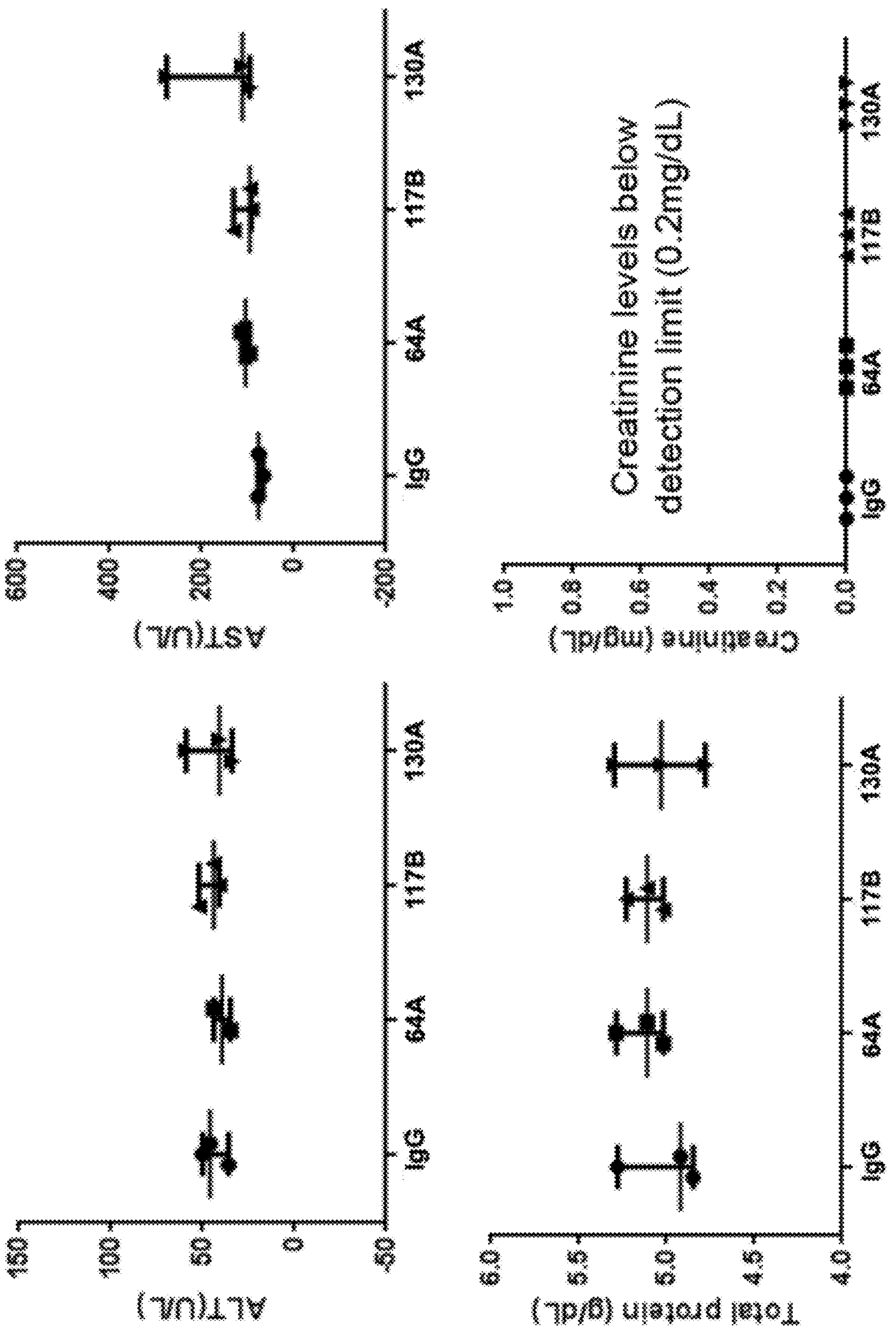
Figure 9C:
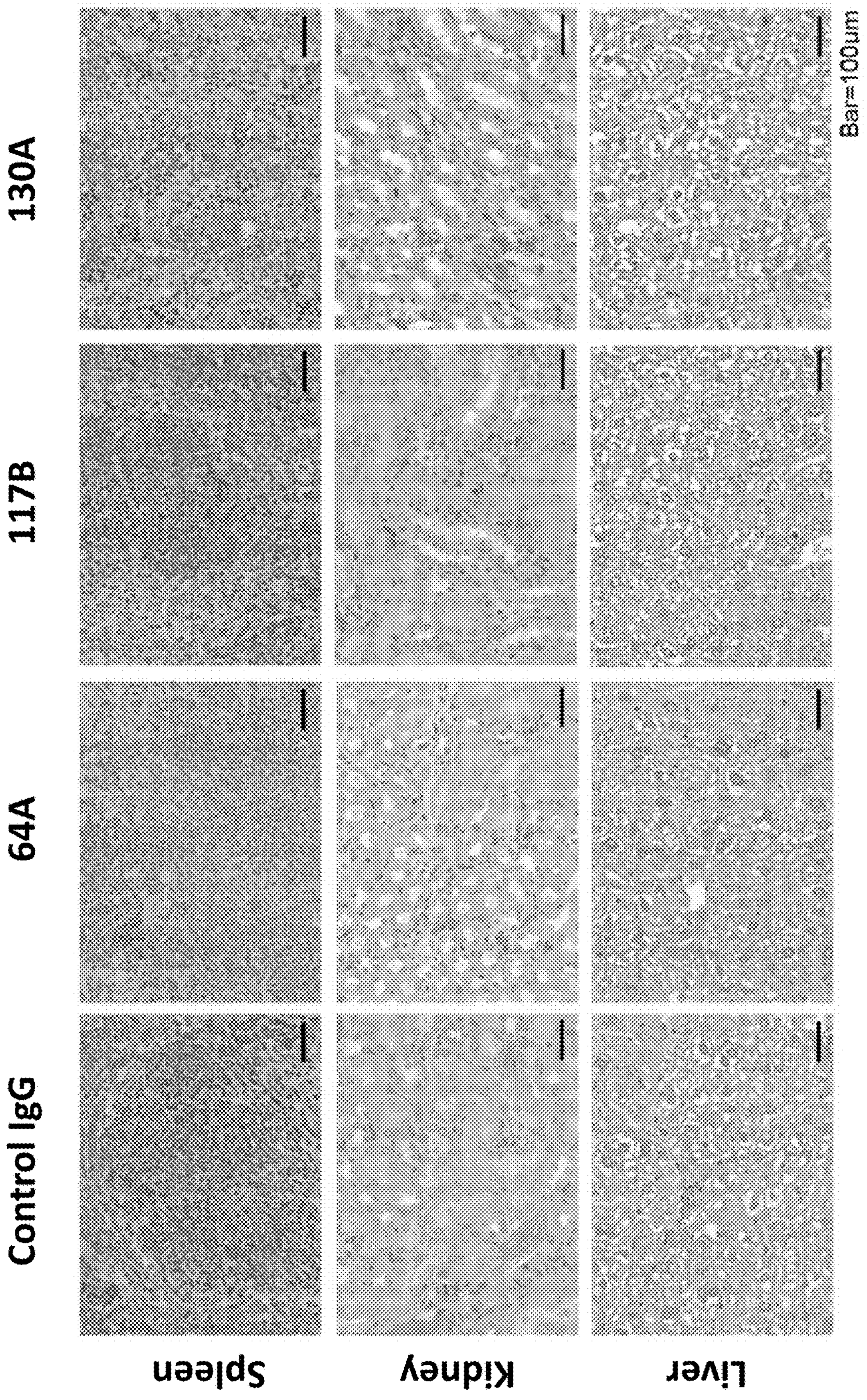
Figure 10A:
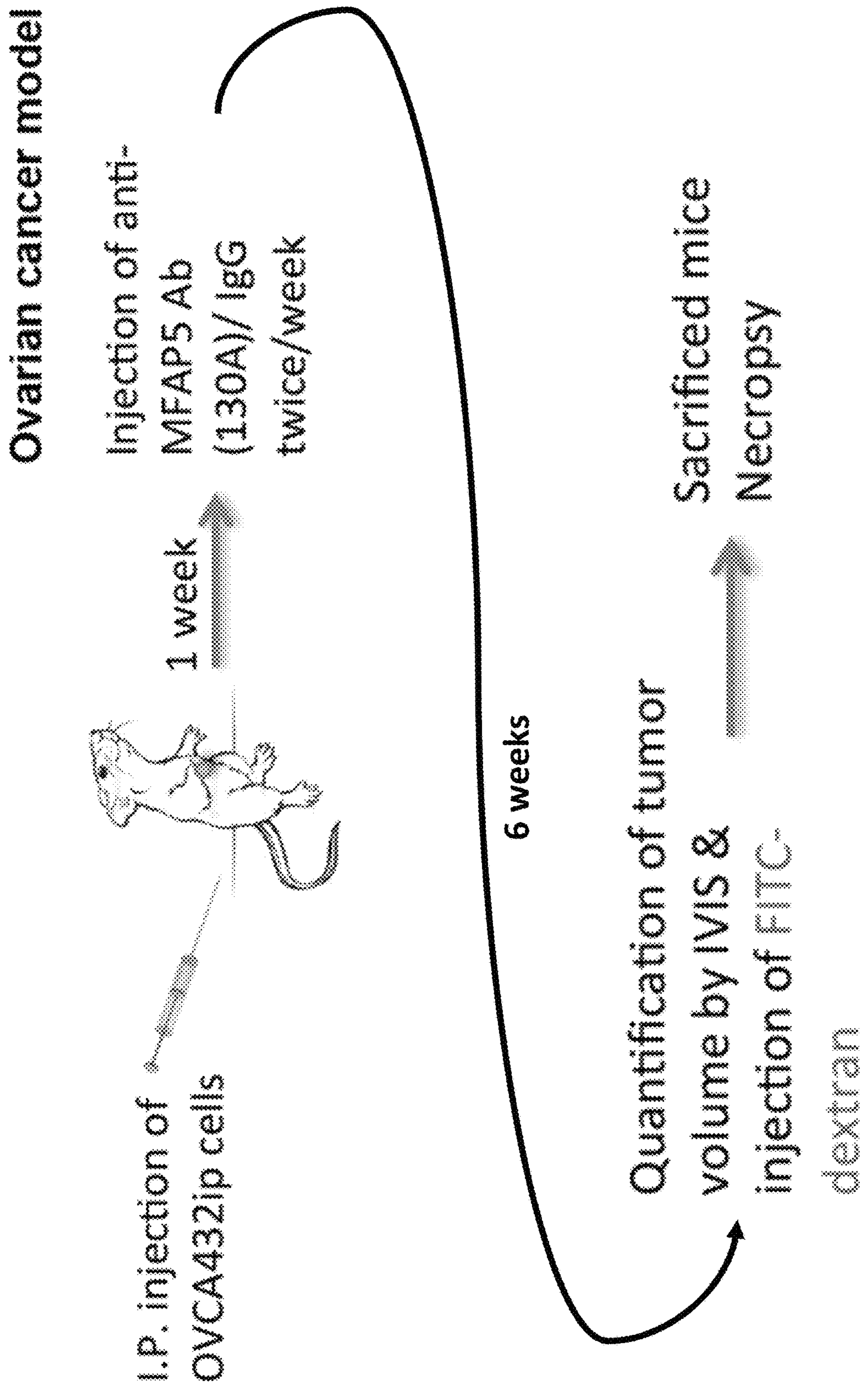
FIG. 10A, FIG. 10B, FIG. 10C, FIG. 10D, FIG. 10E, FIG. 10F, and FIG. 10G show MFAP5-targeting monoclonal antibody suppress ovarian and pancreatic cancer progression in mice.
Figure 10B:
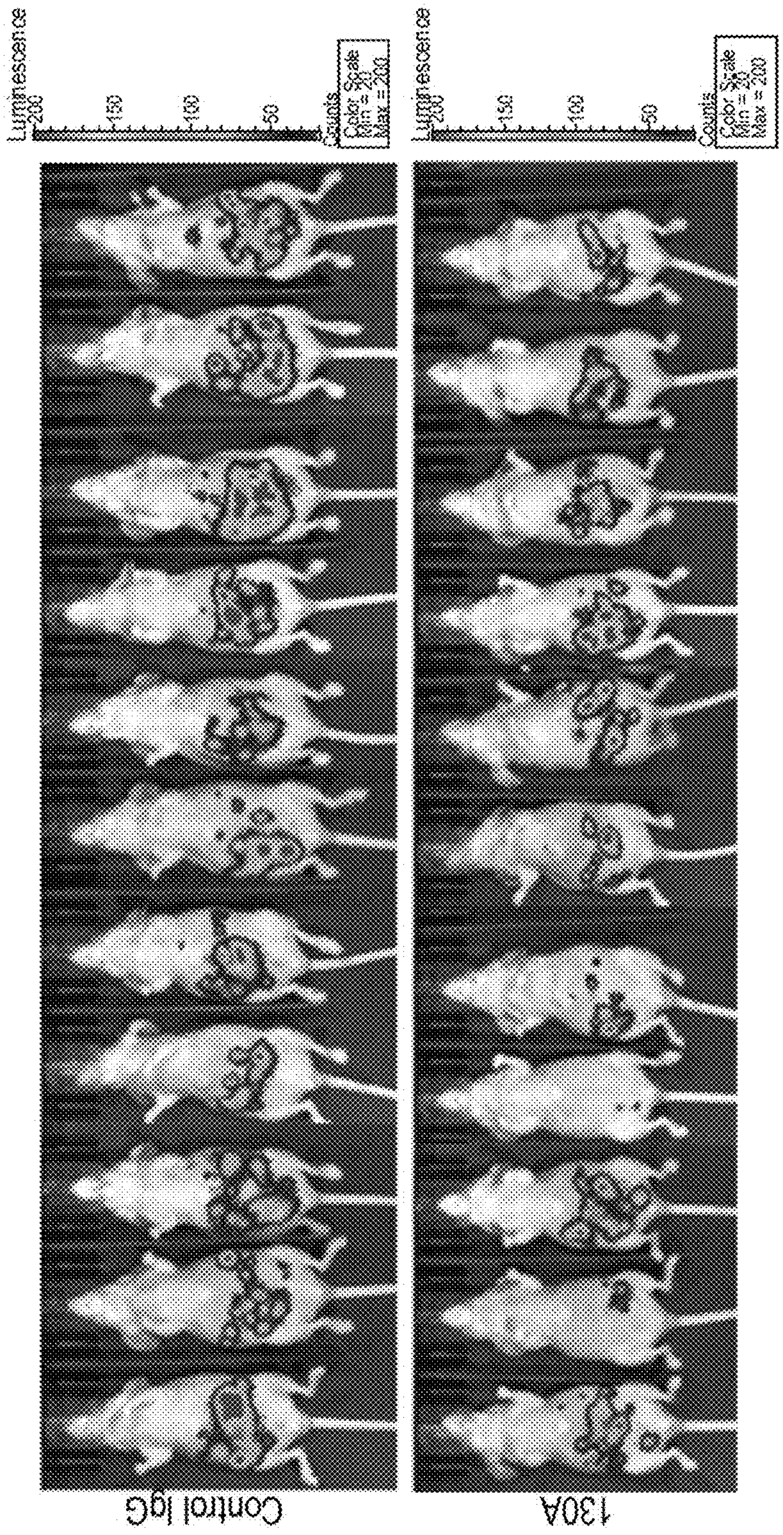
Figure 10B:
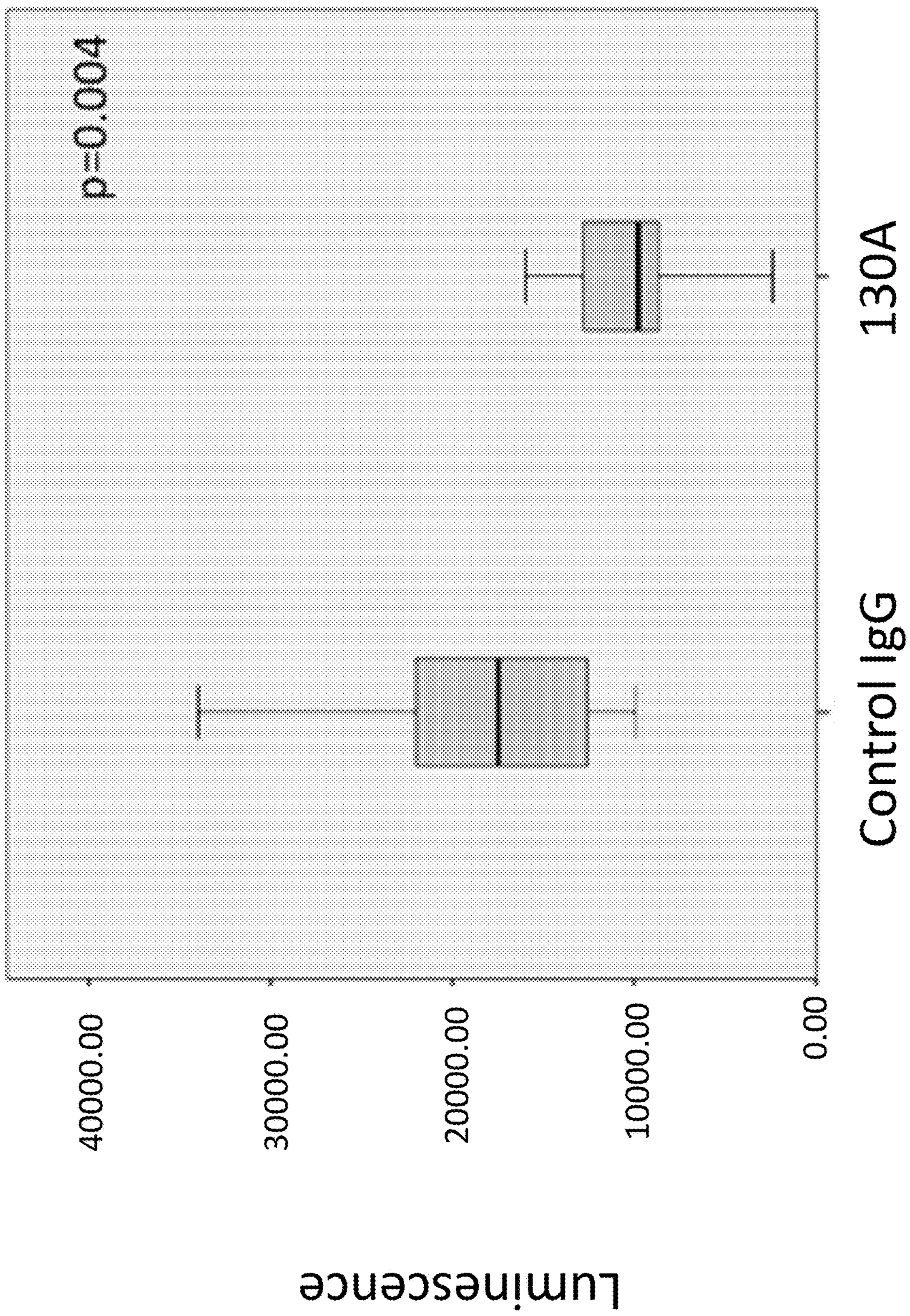
Figure 10C:
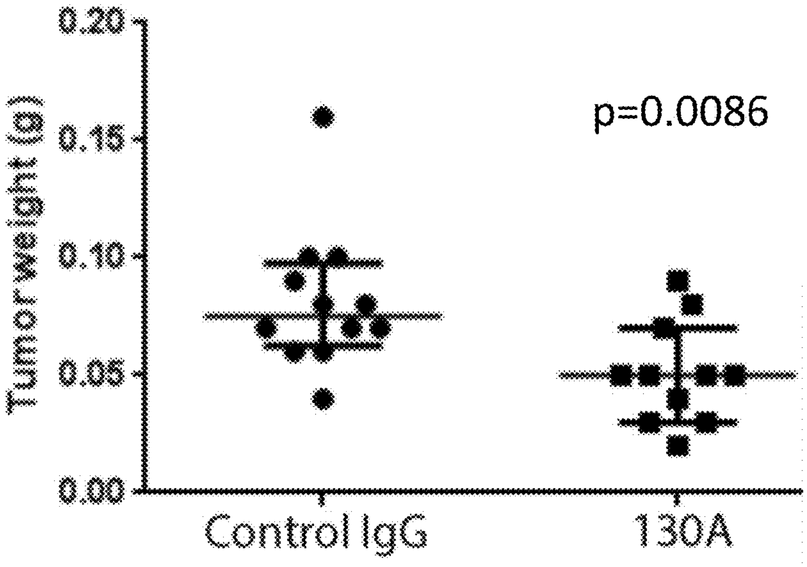

Next, the inhibitory effect of antibody clone 130A, which can recognize and block mouse stromal MFAP5 protein, was evaluated on tumor growth and angiogenesis using in vivo models. Tumor progression was monitored in nude mice injected intraperitoneally with luciferase-labeled OVCA432 ovarian cells treated with either 130A (15 mg/kg) or control normal mouse IgG (15 mg/kg; 12 mice/group). A dosage of 15 mg/kg (twice per week) was used since similar dosages have been used successfully in other FDA-approved antibody treatments targeting different tumor associated antigens. In addition, toxicity studies of monoclonal anti-MFAP5 antibodies showed that mice treated with MAbs (15 mg/kg, twice per week for two weeks) had no adverse effects in complete blood counts, serum ALT, AST, alkaline phosphatase and urea nitrogen levels, and major organ histology (FIG. 9A, FIG. 9B, and FIG. 9C), suggesting that 15 mg/kg was an optimal dose which could be used for mouse treatment (FIG. 10A). The results showed that mice treated with 130A had significantly lower luciferase activity and tumor weight than those treated with normal mouse IgG (FIG. 10B and FIG. 10C).

Figure 10D:
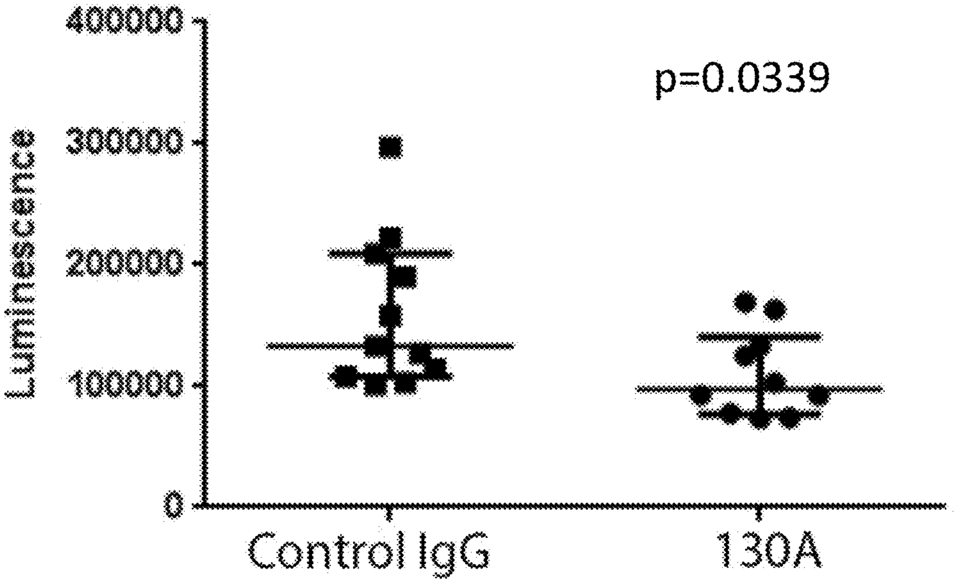
Figure 10D:
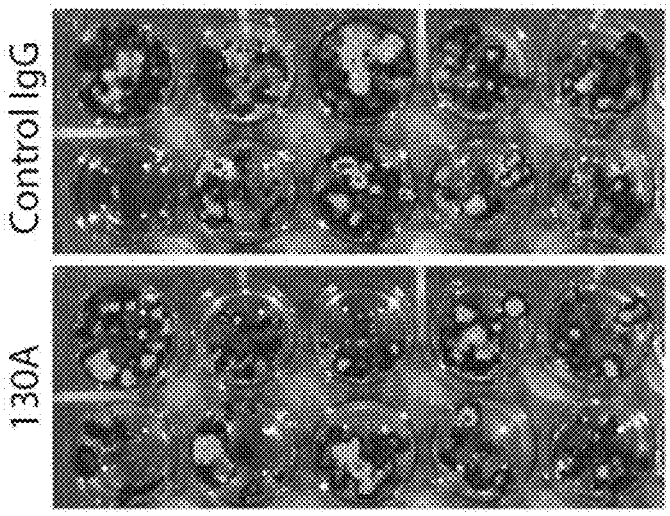
Figure 10E:
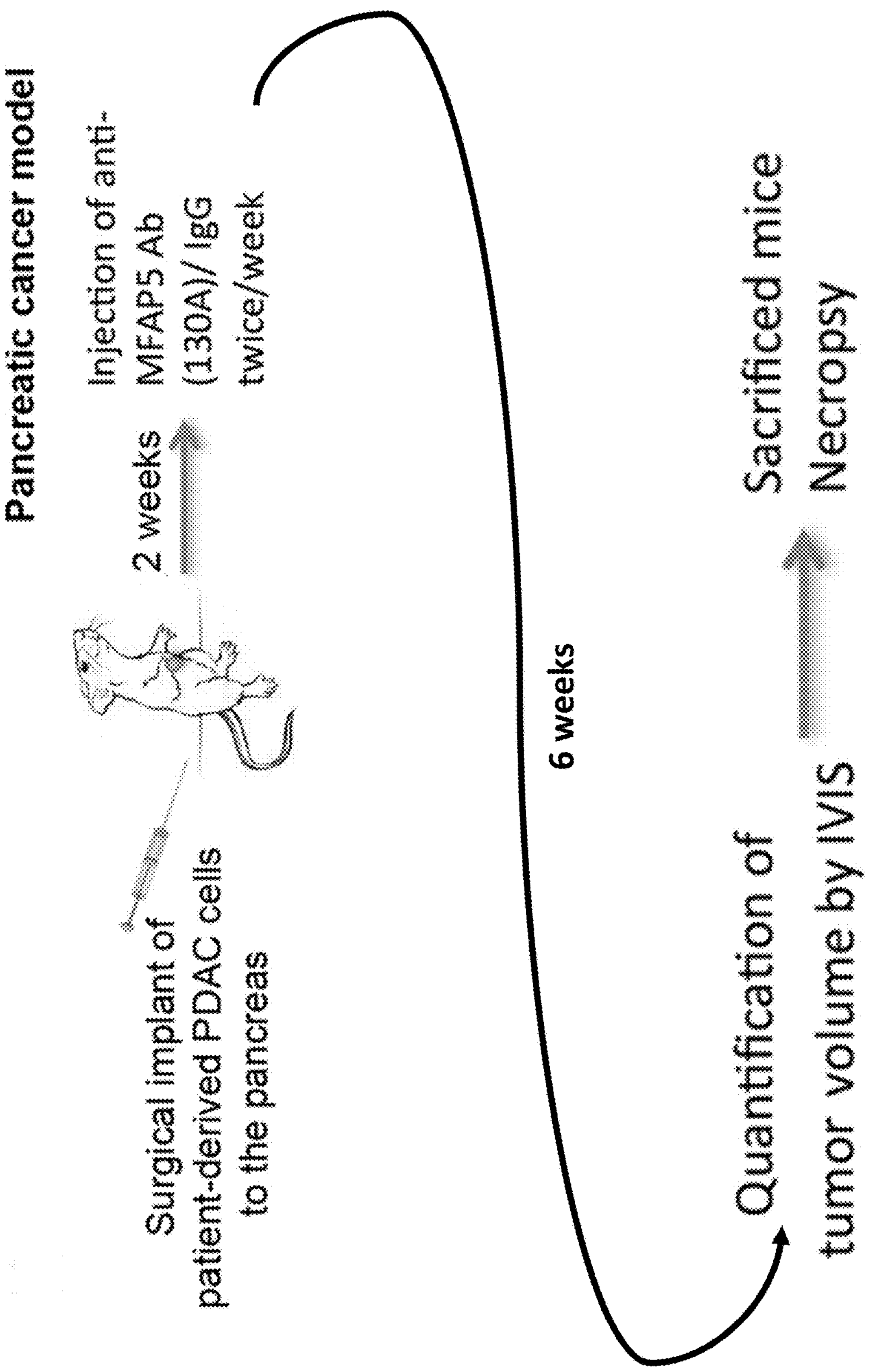
Figure 10F:
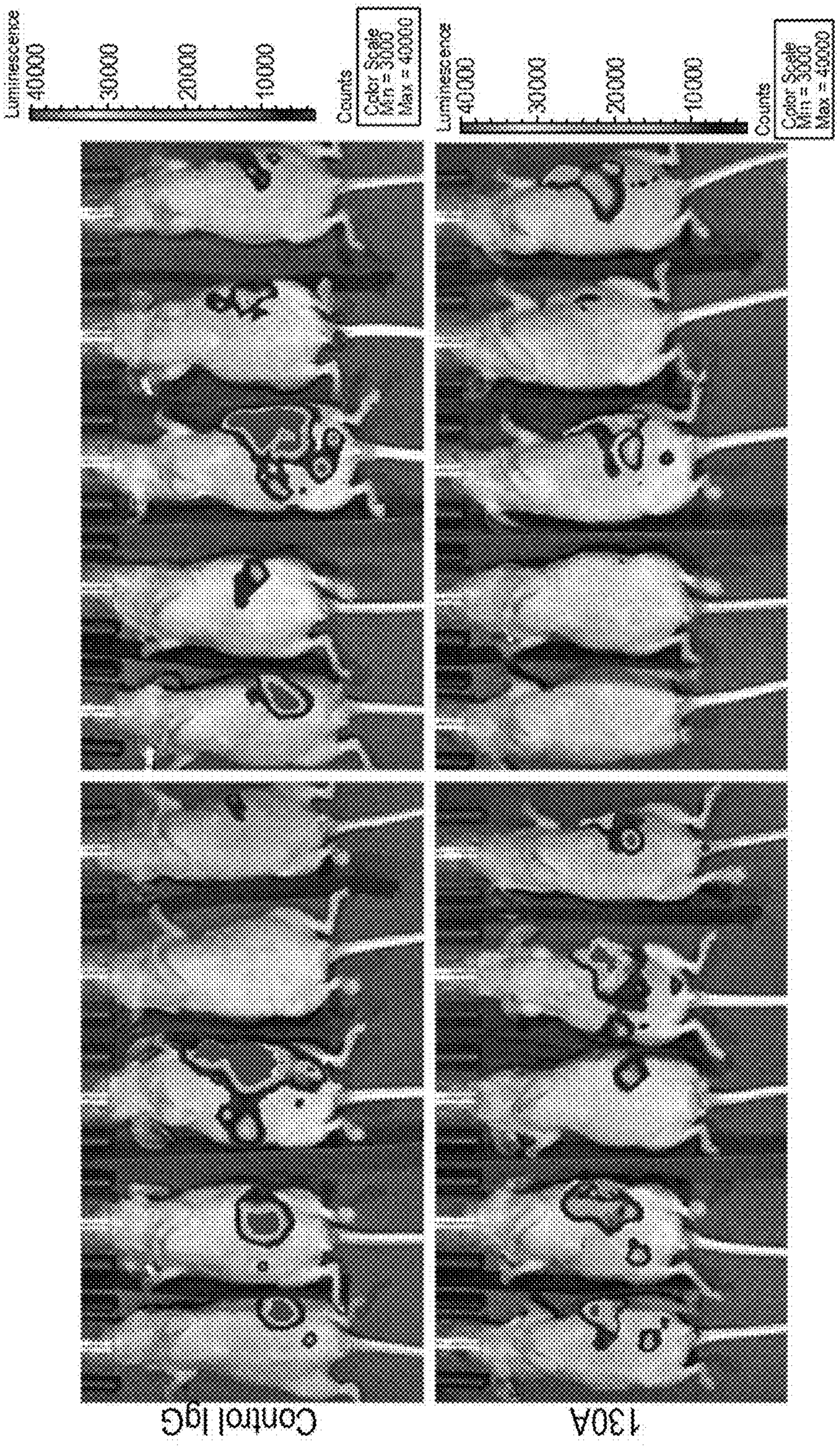
Figure 10F:
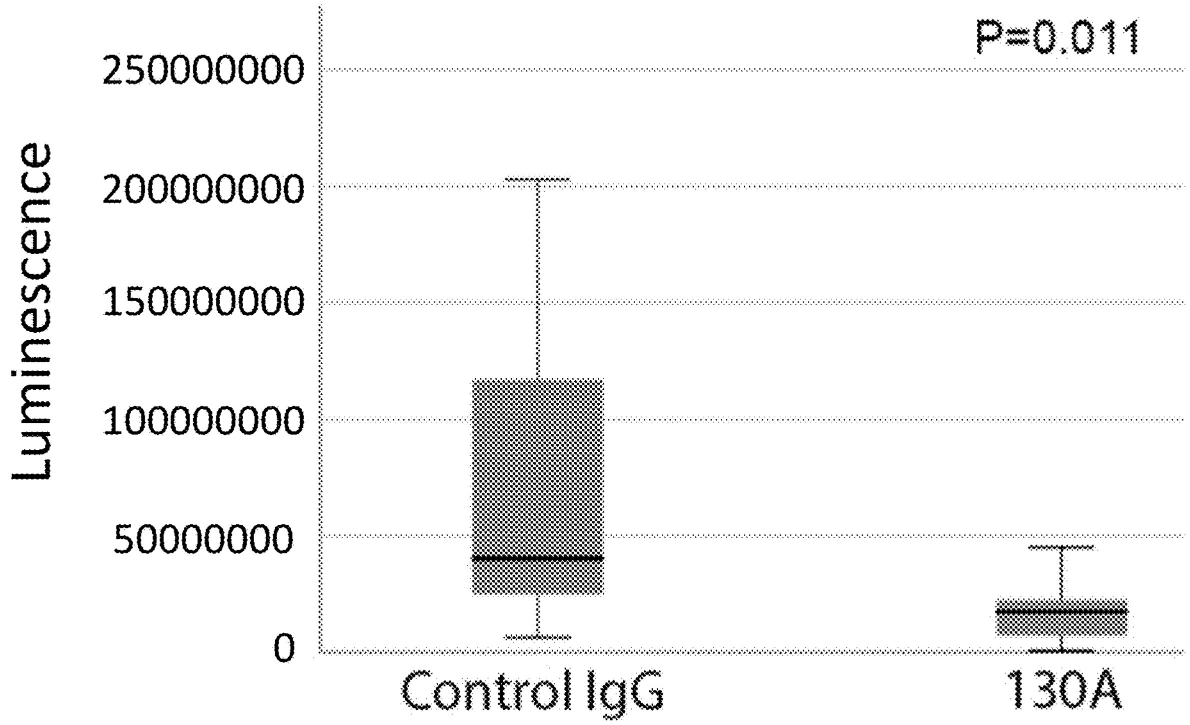
Figure 10G:
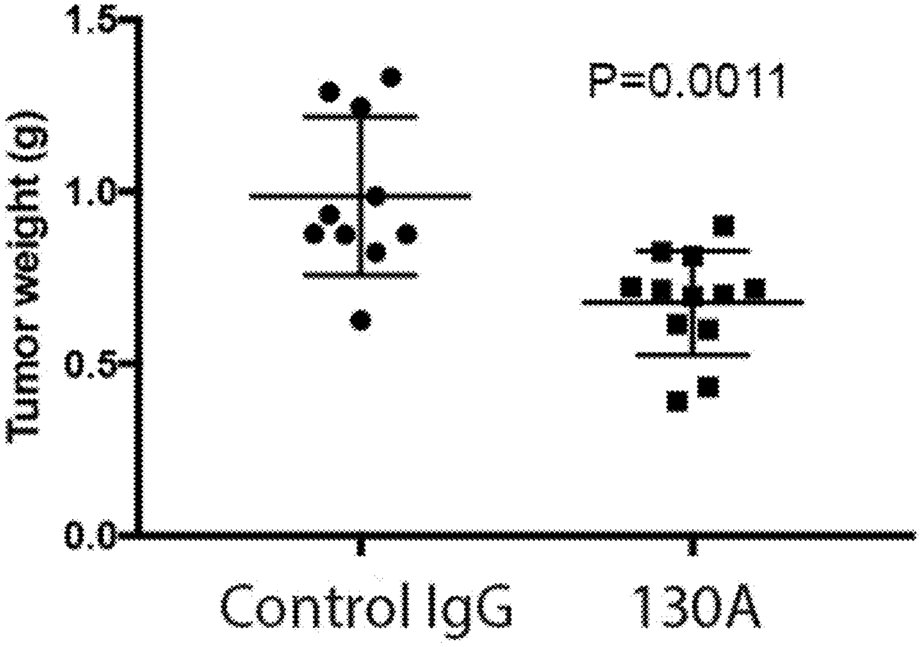

Besides using the ovarian cancer xenograft mouse model, experiments were performed on a PDAC patient-derived tumor xenograft (PDX) cell line PATC53 to determine the efficacy of 130A in suppressing PDAC progression. PDX cell line were injected into the pancreas of nude mice. They were treated with 15 mg/kg 130A MAb or the control IgG twice a week for 6 weeks (FIG. 10D). The results showed that mice treated with 130A MAb had significantly lower luminescence signals and tumor weight than those treated with the IgG control, suggesting that MFAP5 blockade by the 130A antibody suppresses PDAC growth in vivo (FIG. 10E and FIG. 10F).

Figure 15A:
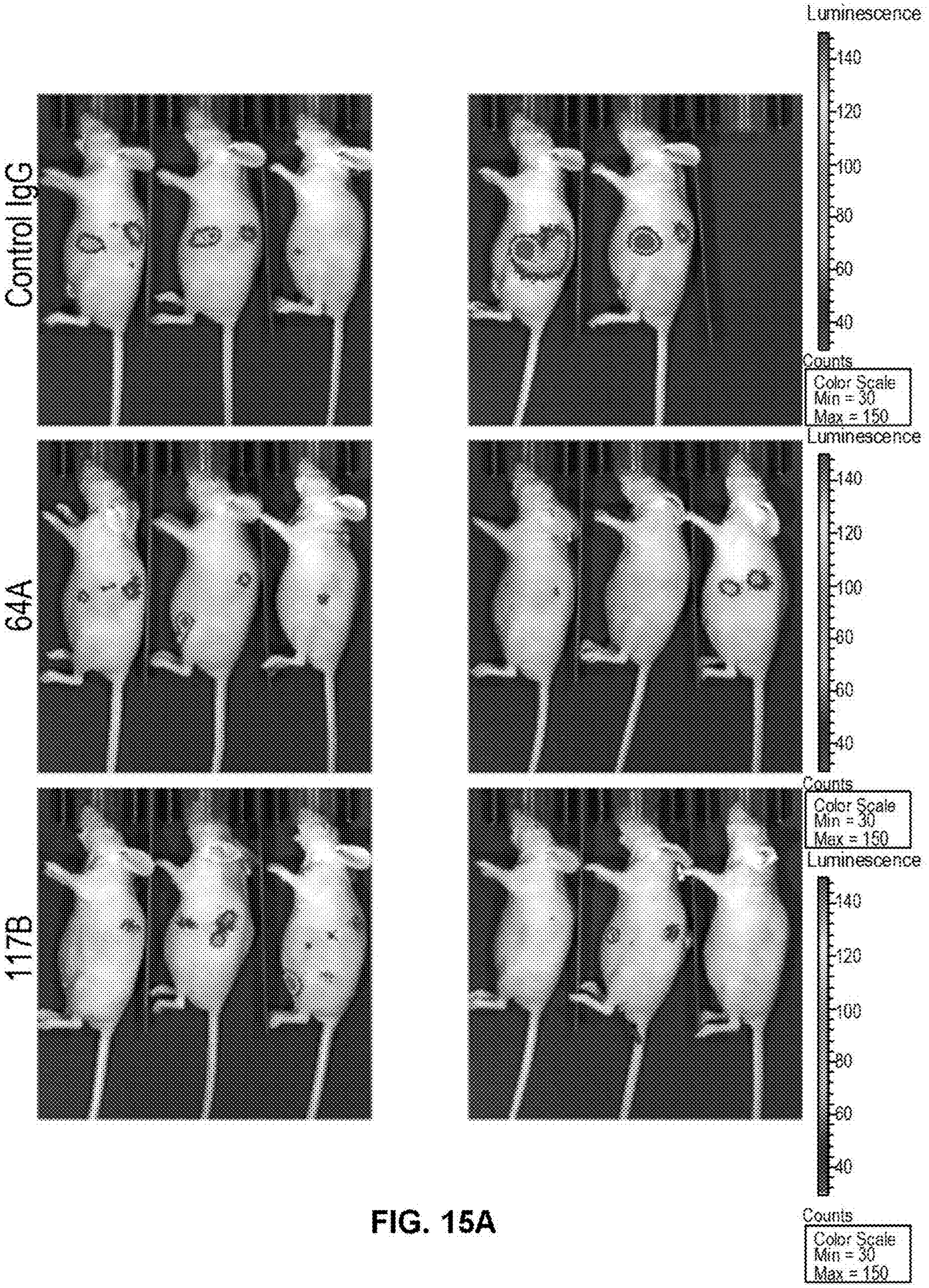
FIG. 15A, FIG. 15B, and FIG. 15C show MFAP5-targeting monoclonal antibody clones 64A and 117B suppress ovarian cancer progression in mice. To evaluate the therapeutic efficacy of antibody clones 64A and 117B, which target MFAP5 of human origin. OVCA3, a MFAP5 expressing human ovarian cancer cell line, was used. Luciferase labeled OVCA3 cancer cells were intraperitoneally injected into nude mice and animals were subsequently treated with either 64A, 117B or control normal mouse IgG at a dosage of 15 mg/kg (FIG. 15A). Animal study results showed that treatment of anti-MFAP5 monoclonal antibody clones 64A and 117B (FIG. 15B) significantly suppressed OVCA3 ovarian tumor growth in mice (P<0.001 and P=0.0029 respectively) (FIG. 15C)
Figure 15B:
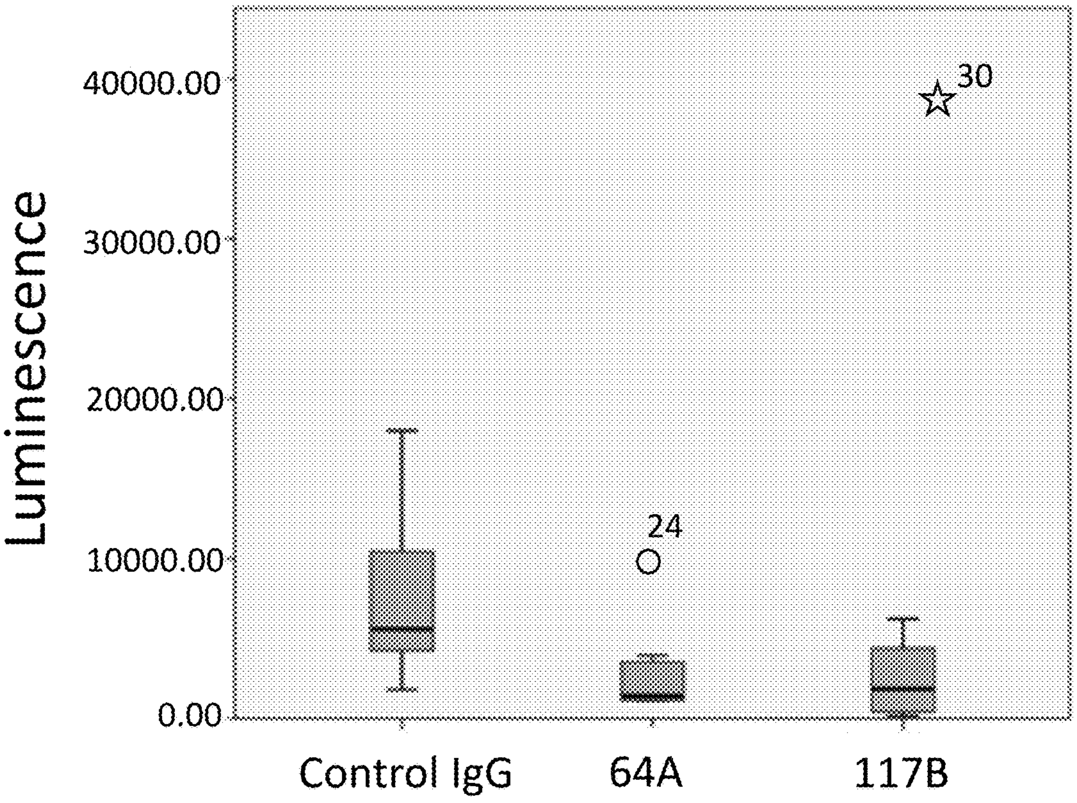
Figure 15C:
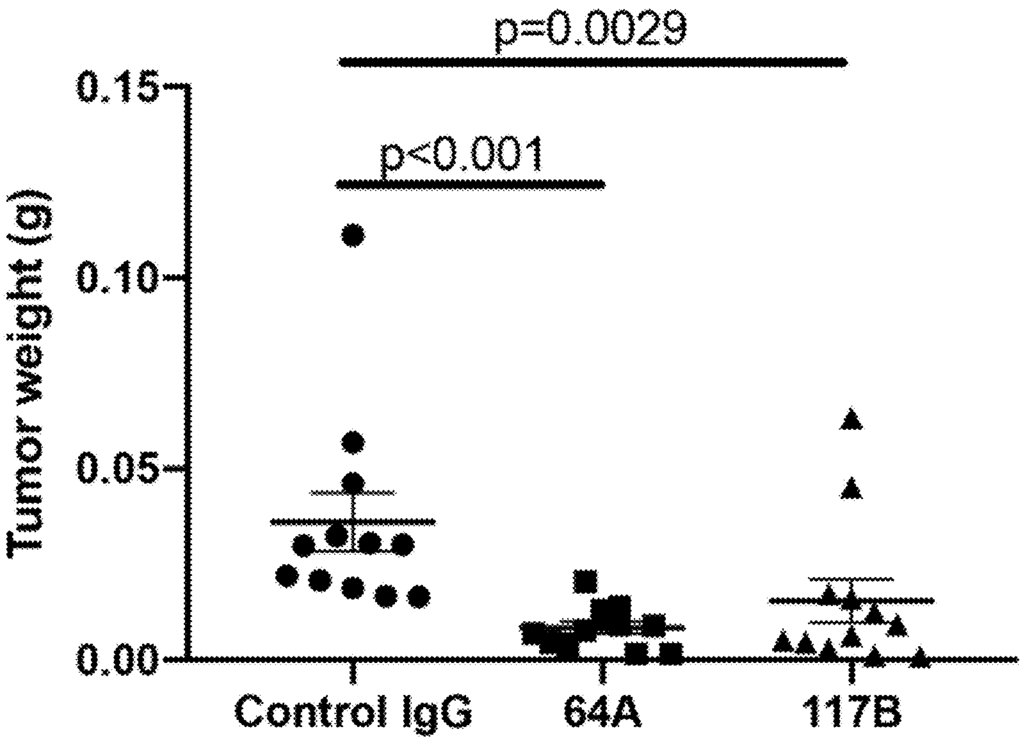
Figure 16A:
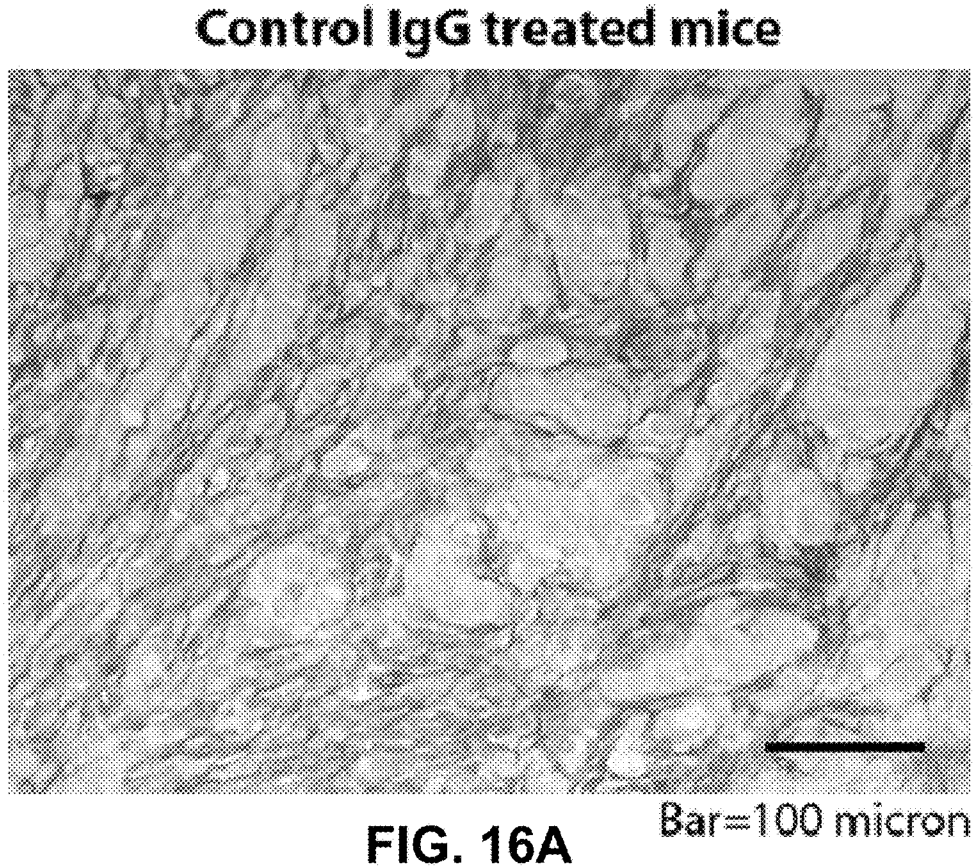
FIG. 16A, FIG. 16B, FIG. 16C, and FIG. 16D show MFAP5-targeting monoclonal antibody reduces cancer fibrosis in pancreatic cancer-bearing mice. Picrosirius red staining of collagen on tumor tissues obtained from PDAC PDX tumor-bearing mice treated with the control IgG (FIG. 16A or the 130A antibody (FIG. 16B) showed that tumors in mice treated with 130A had significantly lower collagen coverage (FIG. 16C) and density (FIG. 16D) in cancer associated stromal tissue than in those treated with IgG.
Figure 16B:
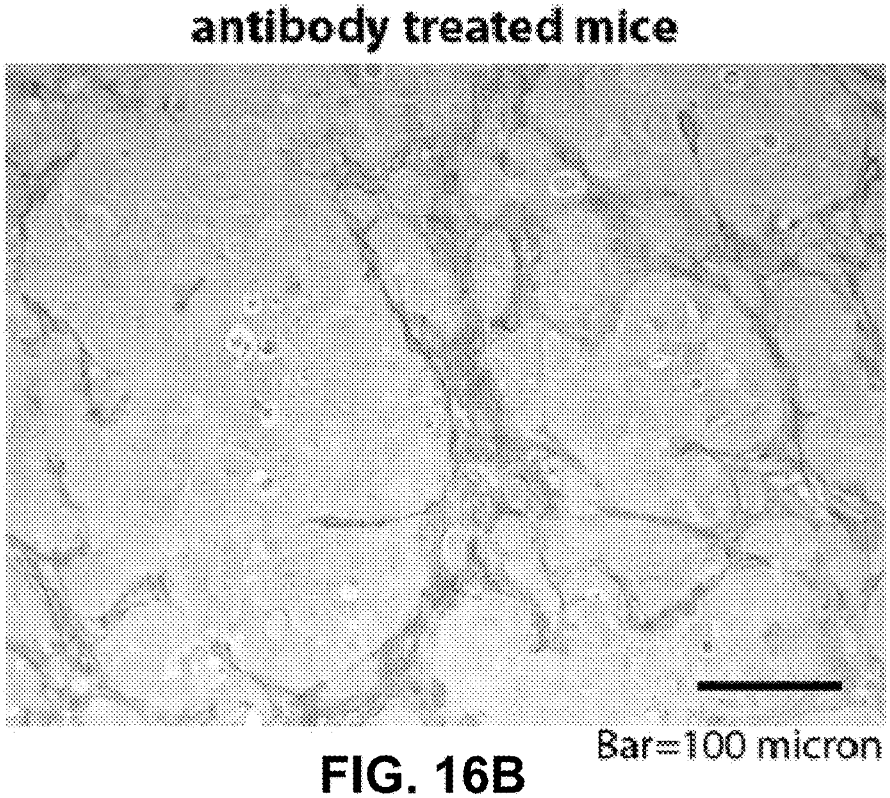
Figure 16C:
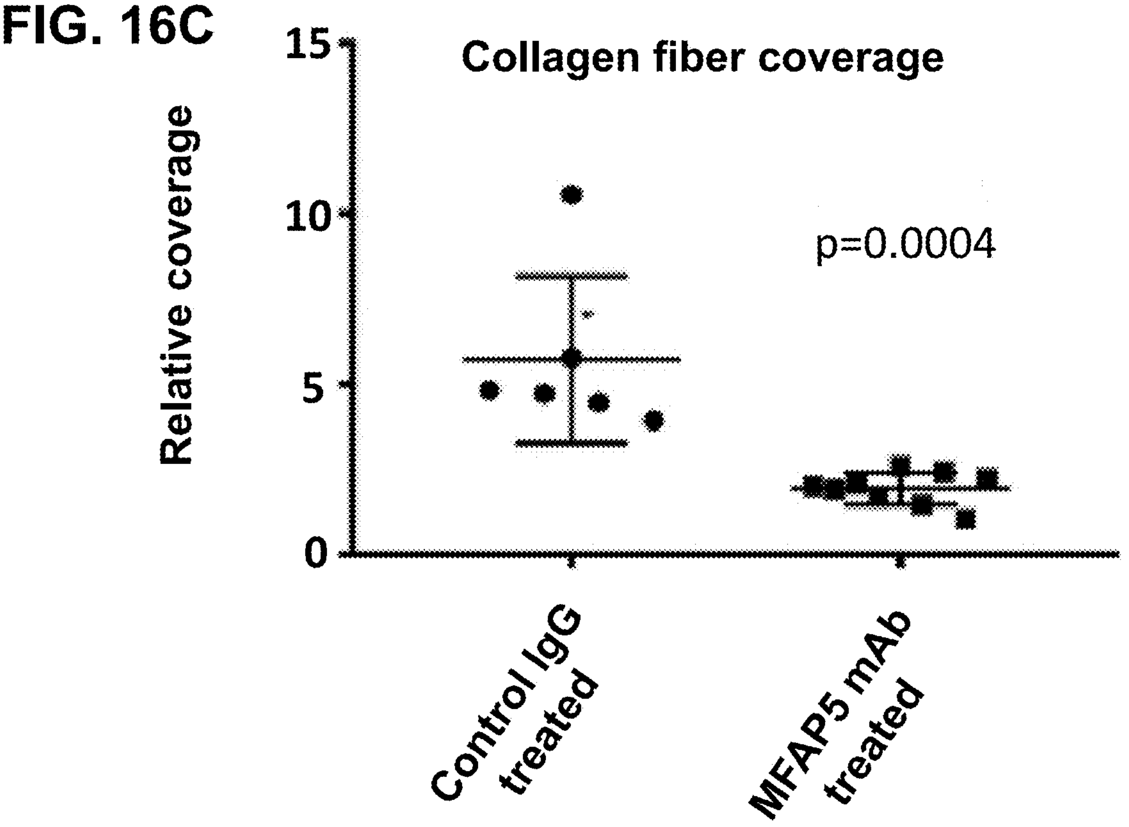
Figure 16D:
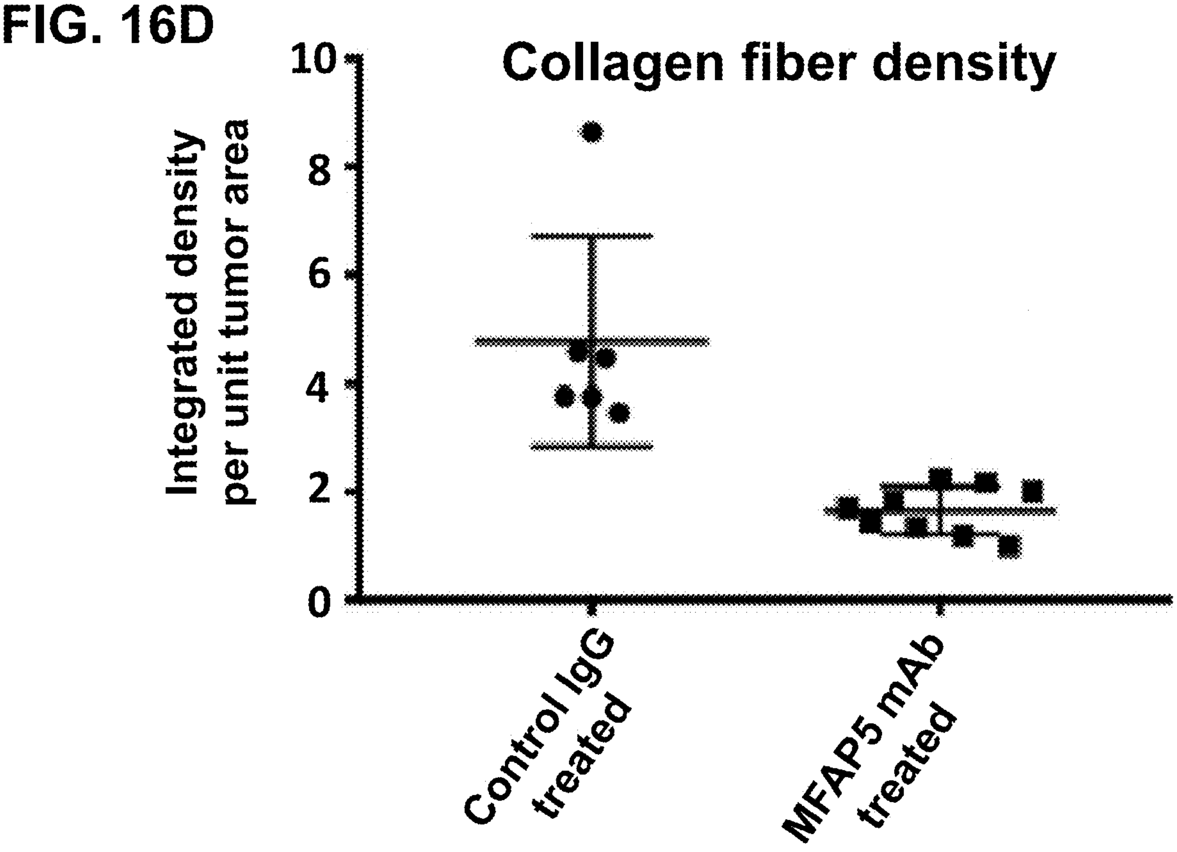

OVCA3, a MFAP5-expressing human ovarian cancer cell line, was used to study the therapeutic effects of targeting human cancer cell-derived MFAP5 in the tumor microenvironment with clone 130A, as well as antibody clones 64A and 117B, which target only MFAP5 of human origin. Briefly, luciferase labeled OVCA3 cancer cells were intraperitoneally injected into nude mice and animals were subsequently treated with either 64A, 117B or control normal mouse IgG at the dosage of 15 mg/kg. Experimental results showed that treatment of anti-MFAP5 monoclonal antibody clones 64A and 117B significantly suppressed OVCA3 ovarian tumor growth in mice (FIG. 15A, FIG. 15B, and FIG. 15C).

Anti-MFAP5 Antibody Increases Chemosensitivity in Animal Models

Figure 11A:
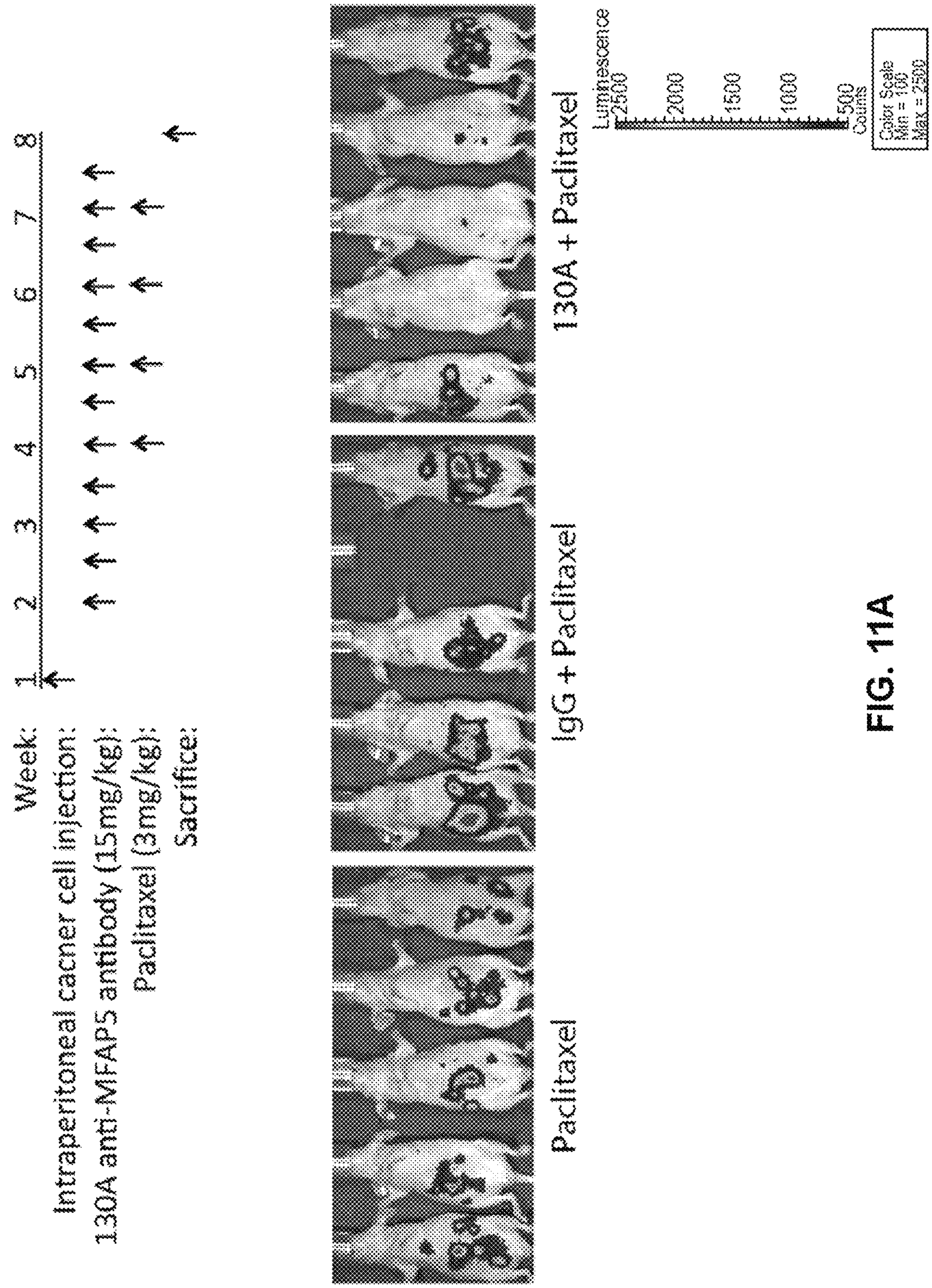
FIG. 11A, FIG. 11B, FIG. 11C, FIG. 11D, FIG. 11E, FIG. 11F, FIG. 11G, and FIG. 11H show MFAP5-targeting monoclonal antibody increase the bioavailability of the chemotherapeutic agent paclitaxel and reduces cancer fibrosis in mice.
Figure 11B:
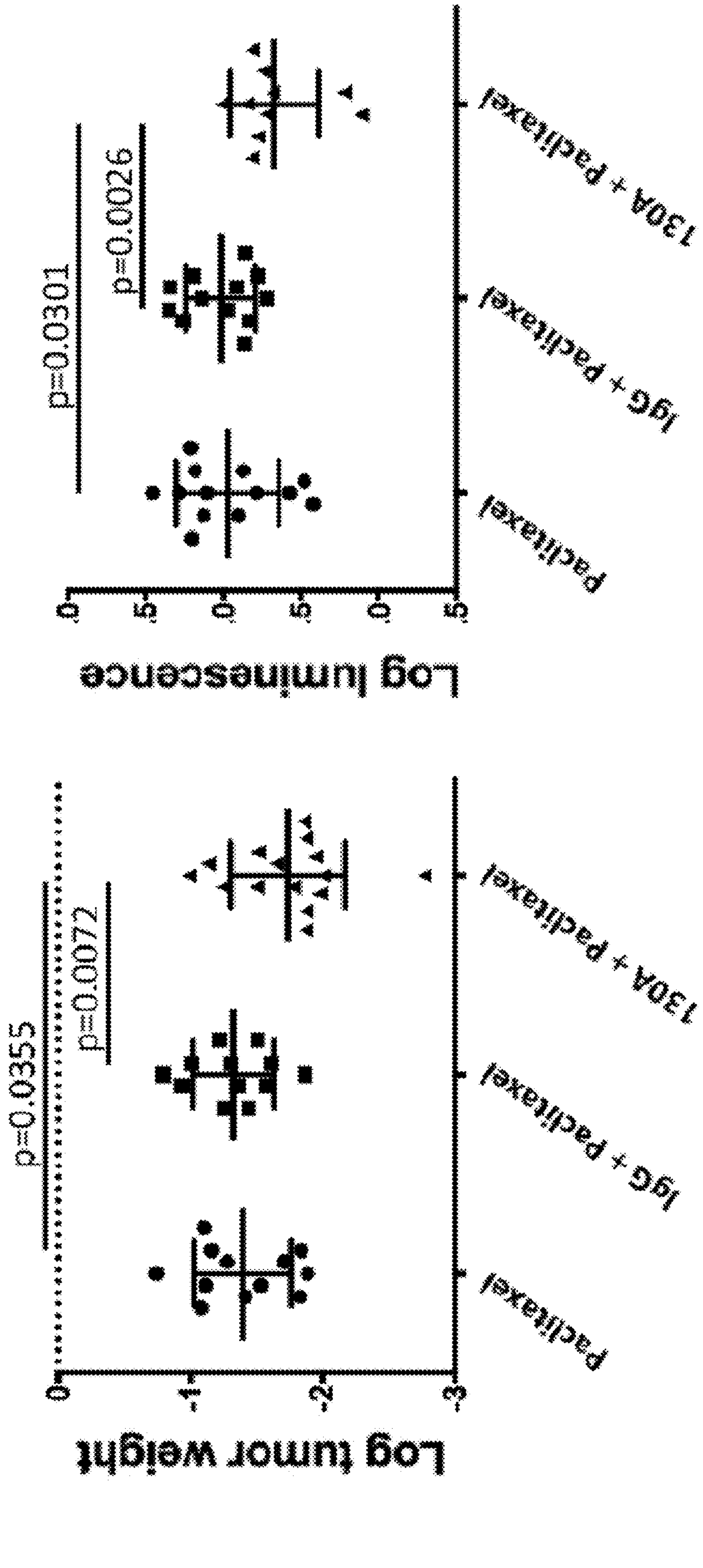

Since previous studies had shown that stromal MFAP5 conferred chemoresistance in ovarian tumor (Leung et al., 2014; Leung et al., 2018), the inventors also determined whether MFAP5 blockade by the anti-MFAP5 antibody could enhance chemosensitivity in an ovarian tumor mouse model. Briefly, OVCA432 tumor-bearing nude mice were treated with paclitaxel together with 130A or the control IgG twice a week. Tumor progression was monitored using the IVIS bioluminescence imaging system. Eight weeks after initial drug treatment, all animals were sacrificed, and their tumor weights and ex vivo tumor luminescence signals were recorded. The results showed that bioluminescence signals of mice and the tumor weight were significantly lower in mice treated with 130A than the IgG did (FIG. 11A and FIG. 11B), suggesting that MFAP5 blockade by the antibody enhances the sensitivity of paclitaxel treatment.

To determine the mechanism by which 130A suppressed tumor progression and chemoresistance in vivo, histologic evaluation of ovarian tumors obtained from mice treated with 130A Mab and the control IgG was performed. Since increased angiogenesis has been shown to be associated with increased chemoresistance in tumor tissues (Goel et al., 2012; McCarroll et al., 2014), the inventors also determined whether 130A Mab treatment suppressed angiogenesis and fibrosis in the tumor tissue. Immunolocalization of CD34-positive microvessels showed that tumor tissue in mice treated with 130A Mab had a significant lower microvessel density than those treated with IgG (FIG. 11C), suggesting that MFAP5 blockade by the 130A antibody inhibited angiogenesis, most likely by preventing the binding of MFAP5 to $\alpha v\beta_3$ integrin on endothelial cells, and activating calcium dependent FAK/ERK/LPP signaling pathway as observed previously (Mok et al., 2009; Leung et al., 2018).

Figure 11C:
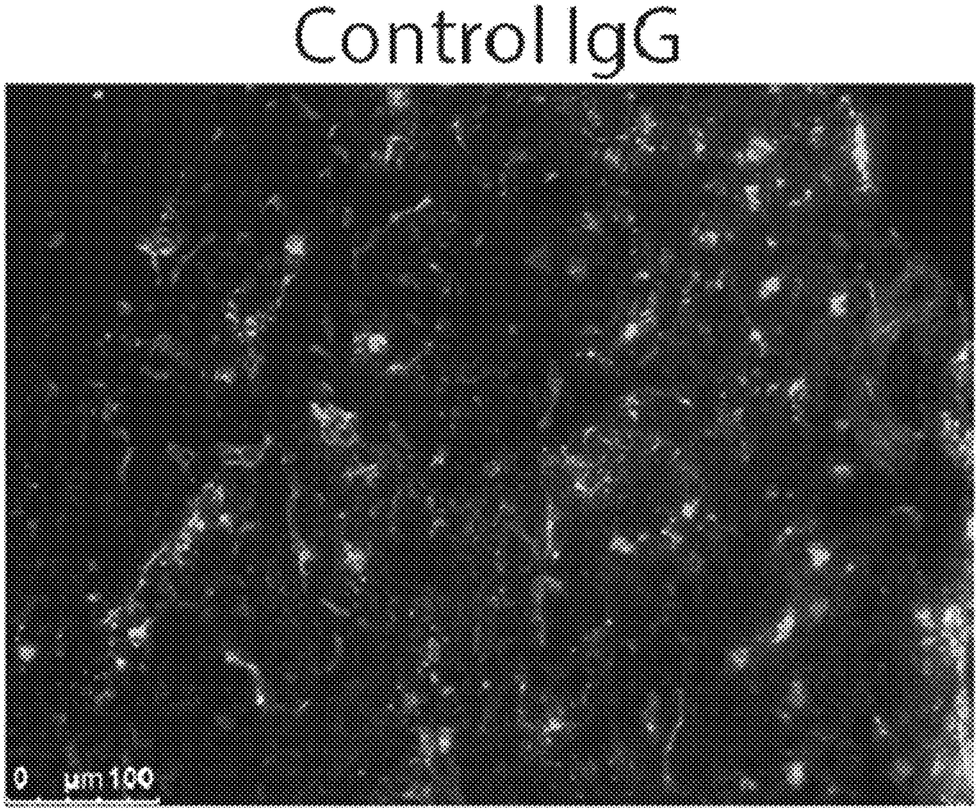
Figure 11C:
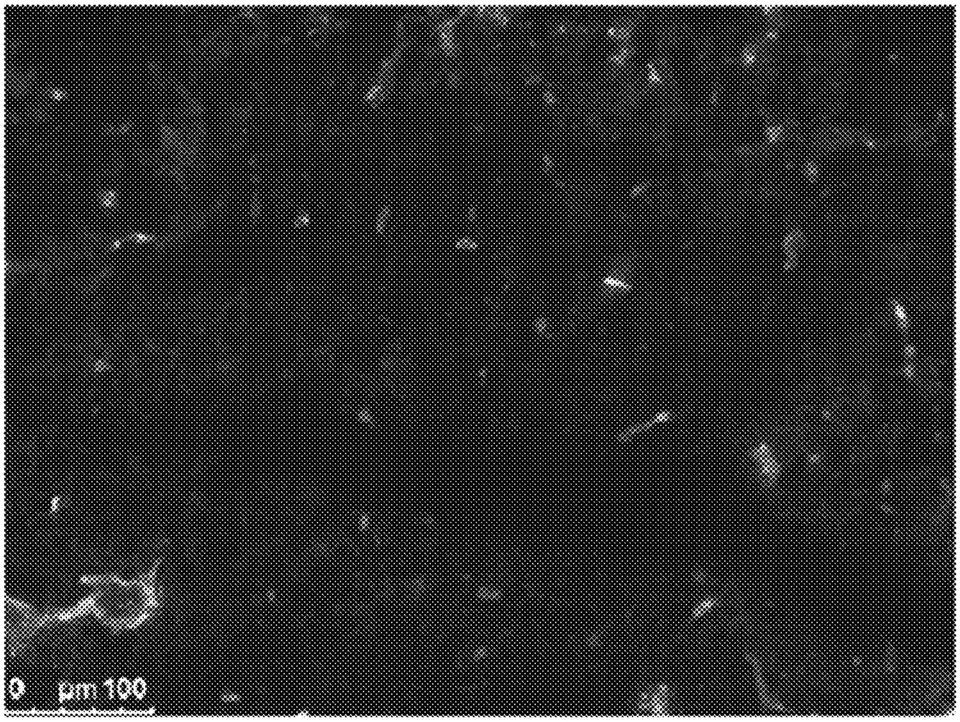
Figure 11C:
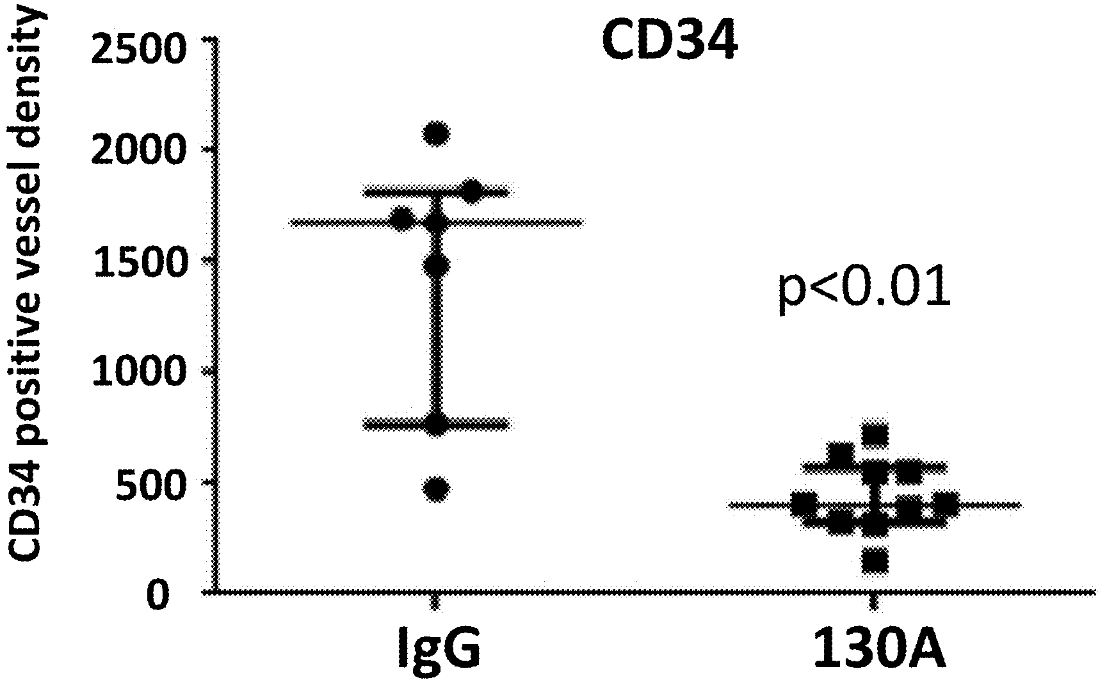
Figure 11C:
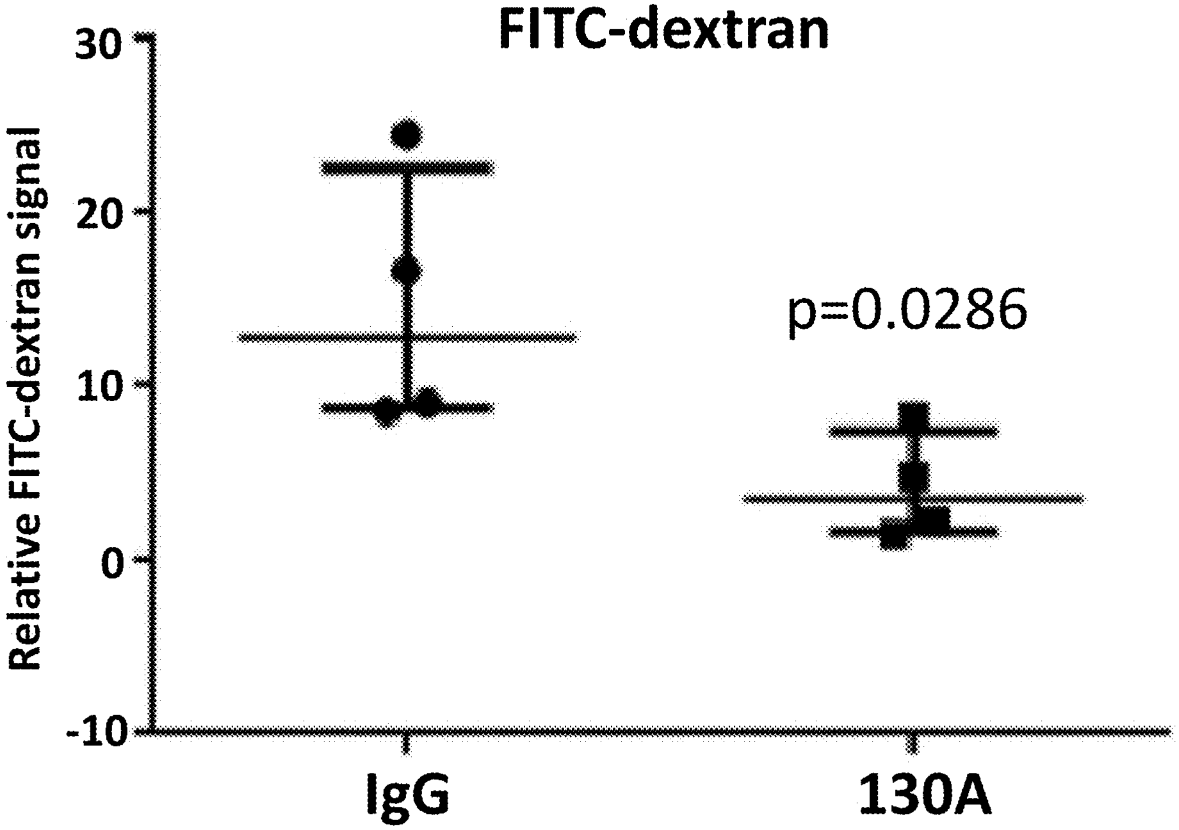

To determine whether vessel normalization played a role in mediating the effect of MFAP5 blockade in enhancing paclitaxel sensitivity, intratumoral microvessel leakiness was determined by injecting FITC-dextran into tail veins of mice before they were sacrificed. The results showed that perivascular FITC-dextran signals in ovarian tumors were significantly lower in the 130A MAb-treated mice than in the control mice, suggesting that MFAP5 blockade reduced intratumoral microvessel leakiness (FIG. 11C).

Figure 11D:
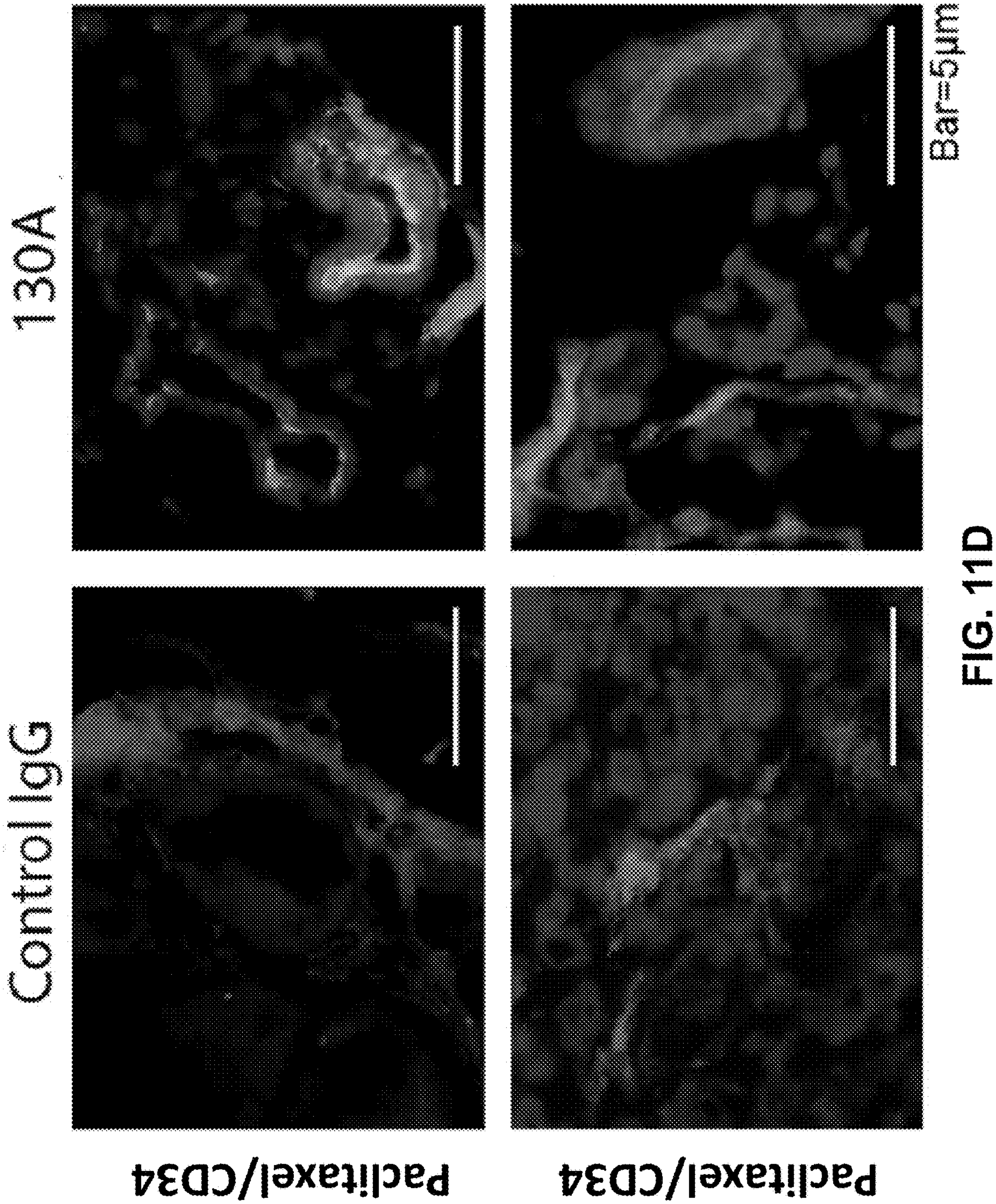
Figure 11D:
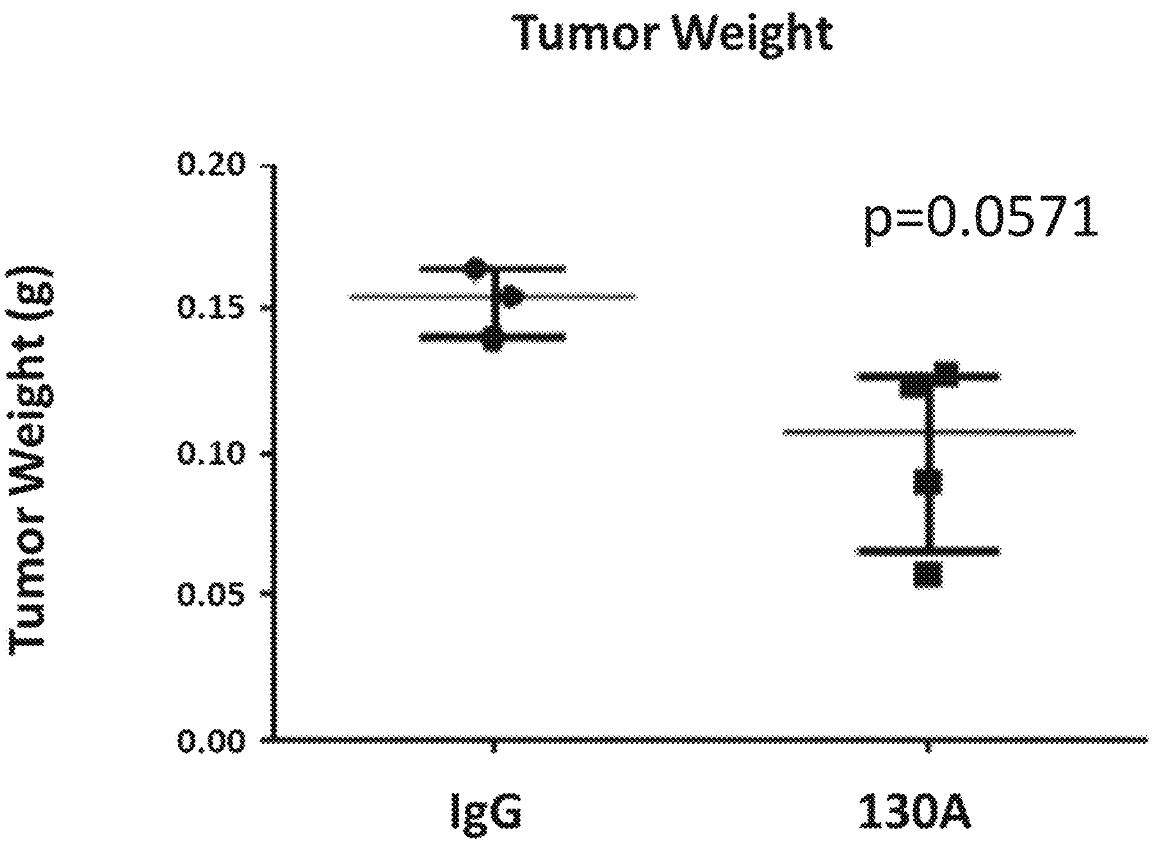
Figure 11D:
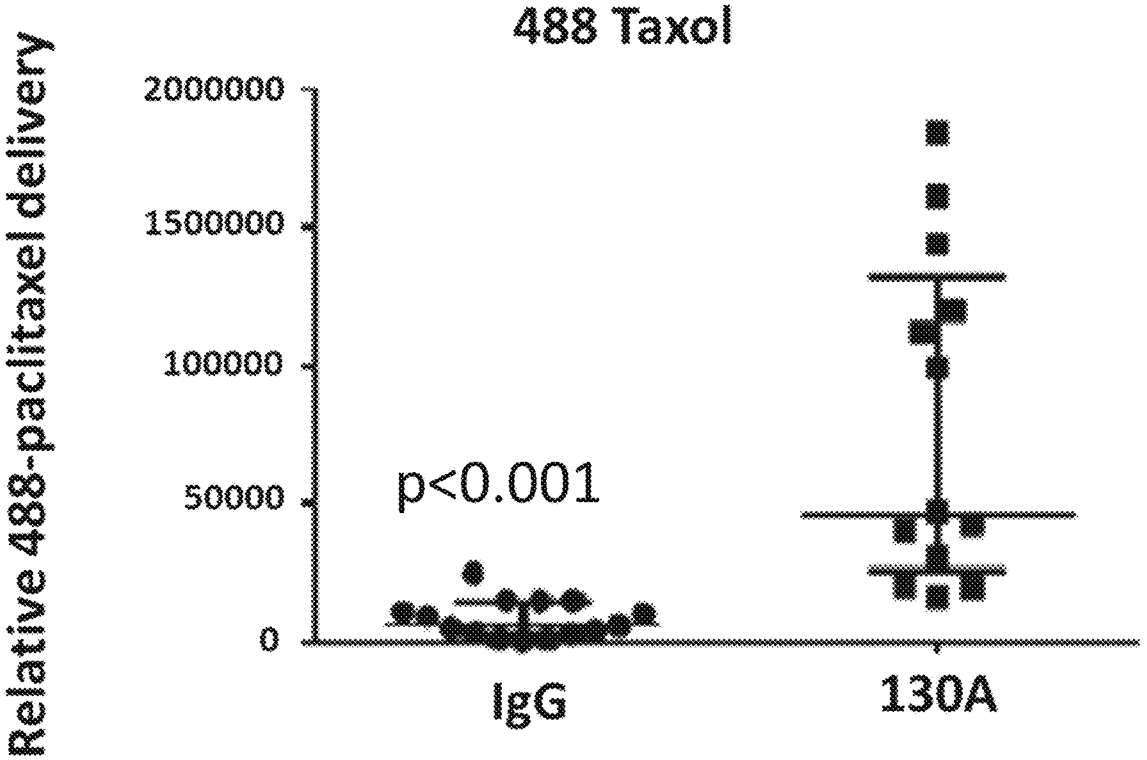
Figure 11D:
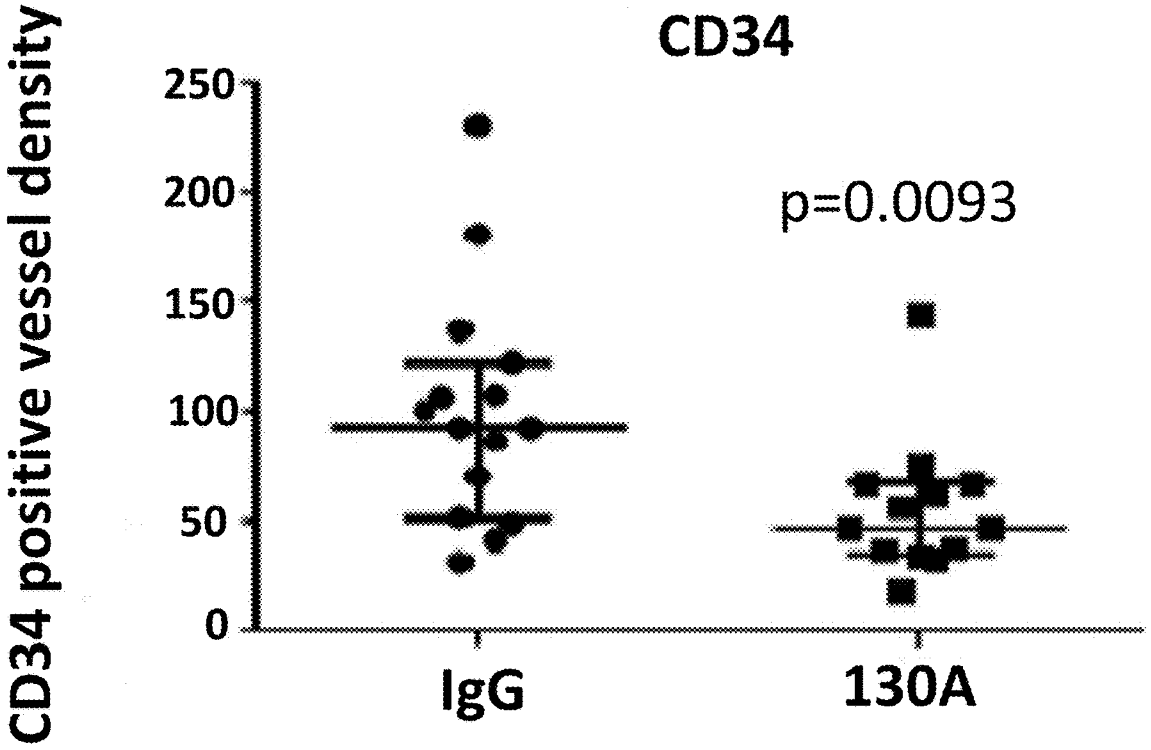
Figure 11D:
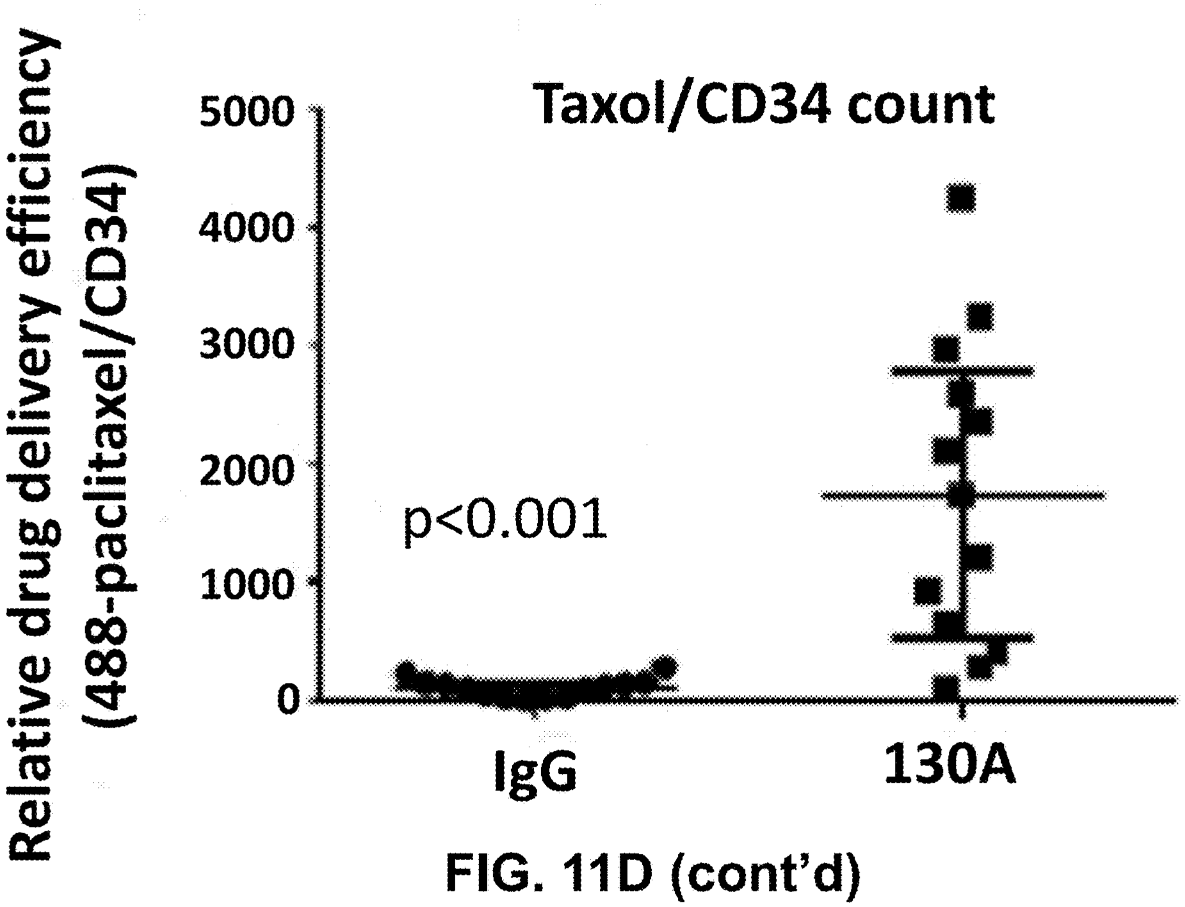

To evaluate whether the reduced intratumoral microvessel leakiness resulting from 130A antibody treatment affected the bioavailability of systemically administered drugs in ovarian tumors, OVCA432 tumor-bearing mice were treated with 130A or the control IgG for 4 weeks before intravenous injection of Oregon Green 488-conjugated paclitaxel into each animal. Fluorescent microscopy was then performed on tumor tissue sections. The results showed that tumor tissues obtained from mice treated with 130A had significantly stronger greater Oregon Green 488 signals than those treated with the control IgG (FIG. 11D), suggesting that MFAP5 blockade increases paclitaxel bioavailability in the tumor tissue and thus enhances paclitaxel sensitivity.

MFAP5 Blockage by Anti-Mfap5 Antibody Reduces Cancer Fibrosis

Figure 11E:
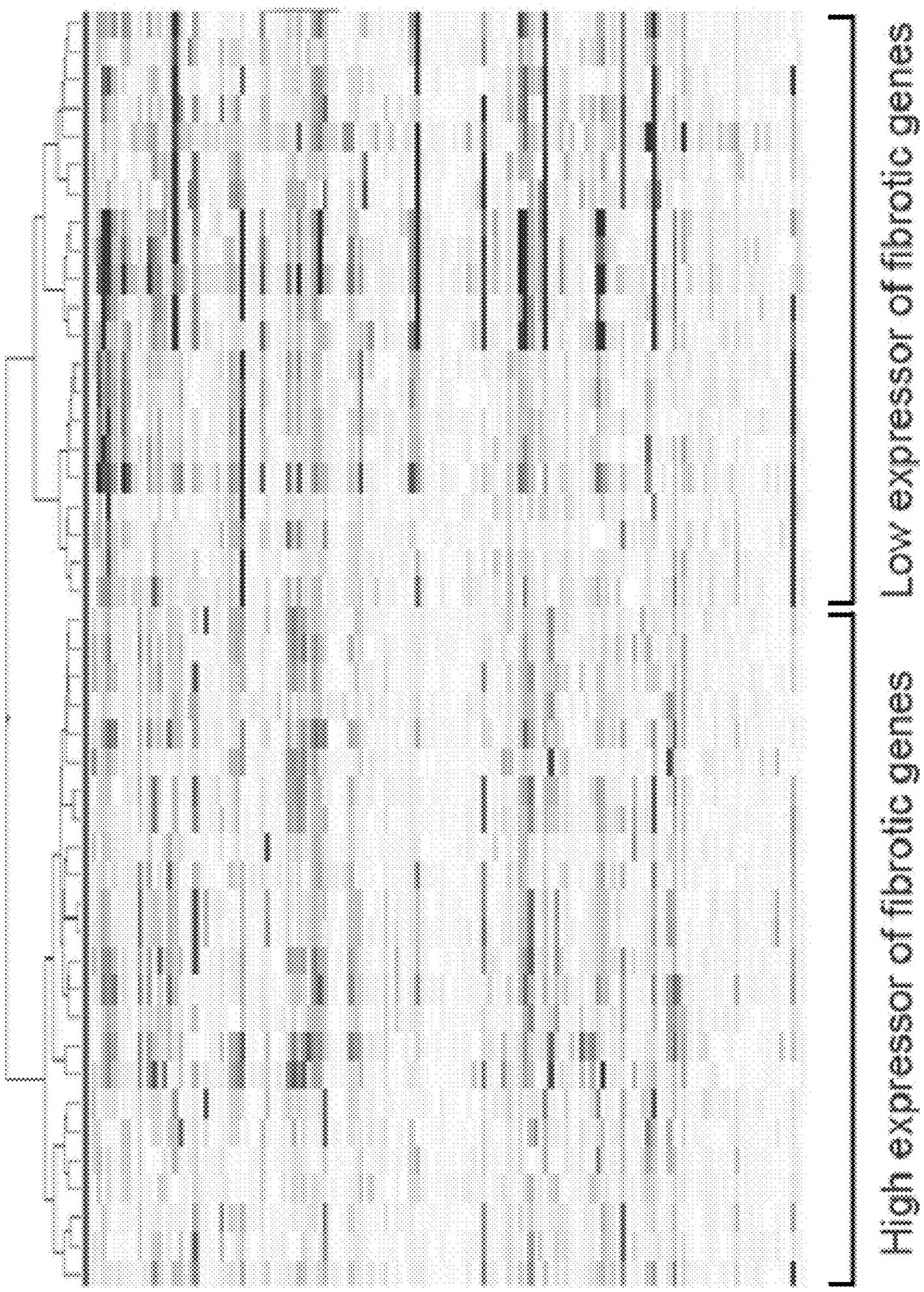
Figure 11E:
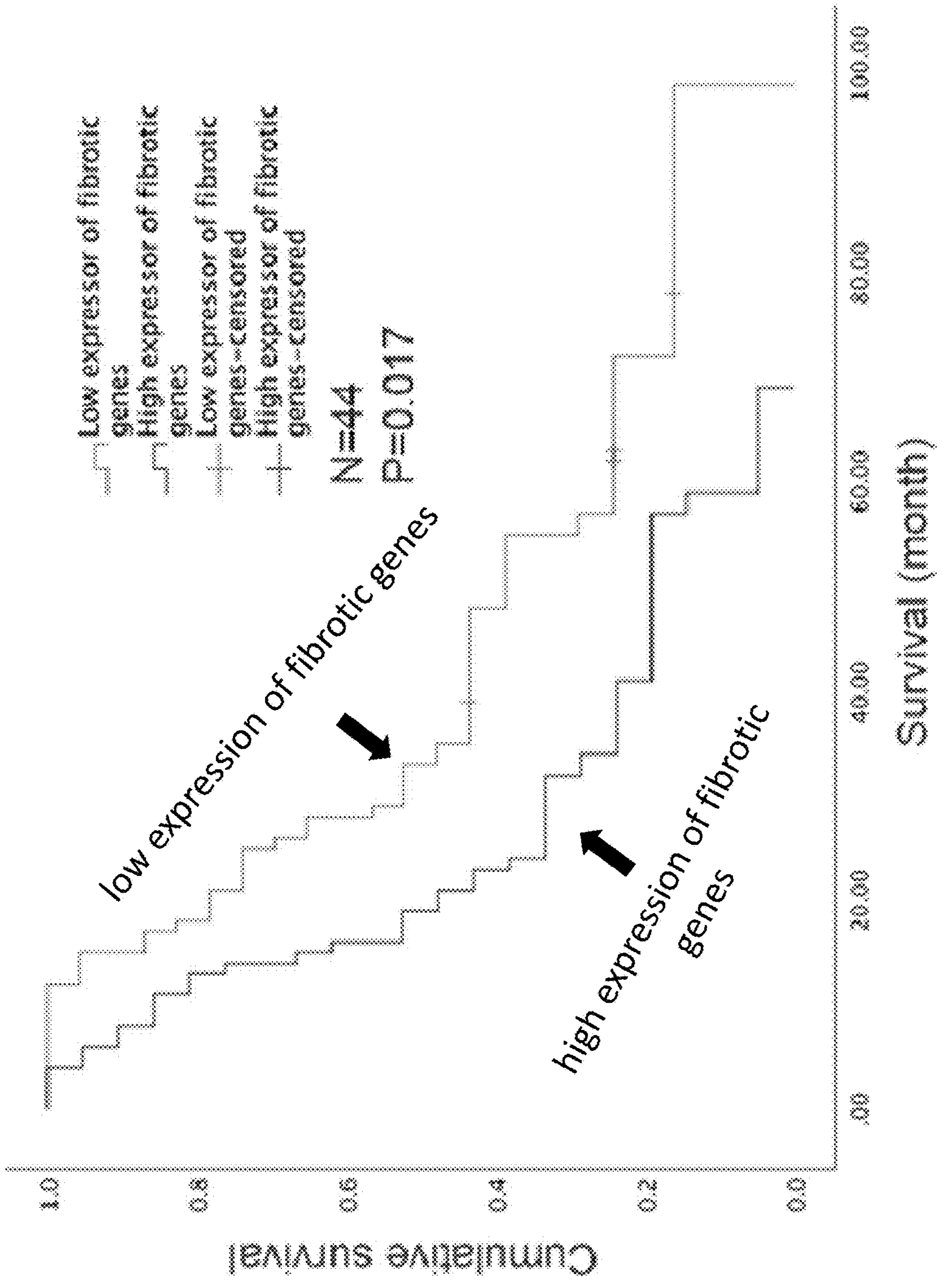
Figure 11F:
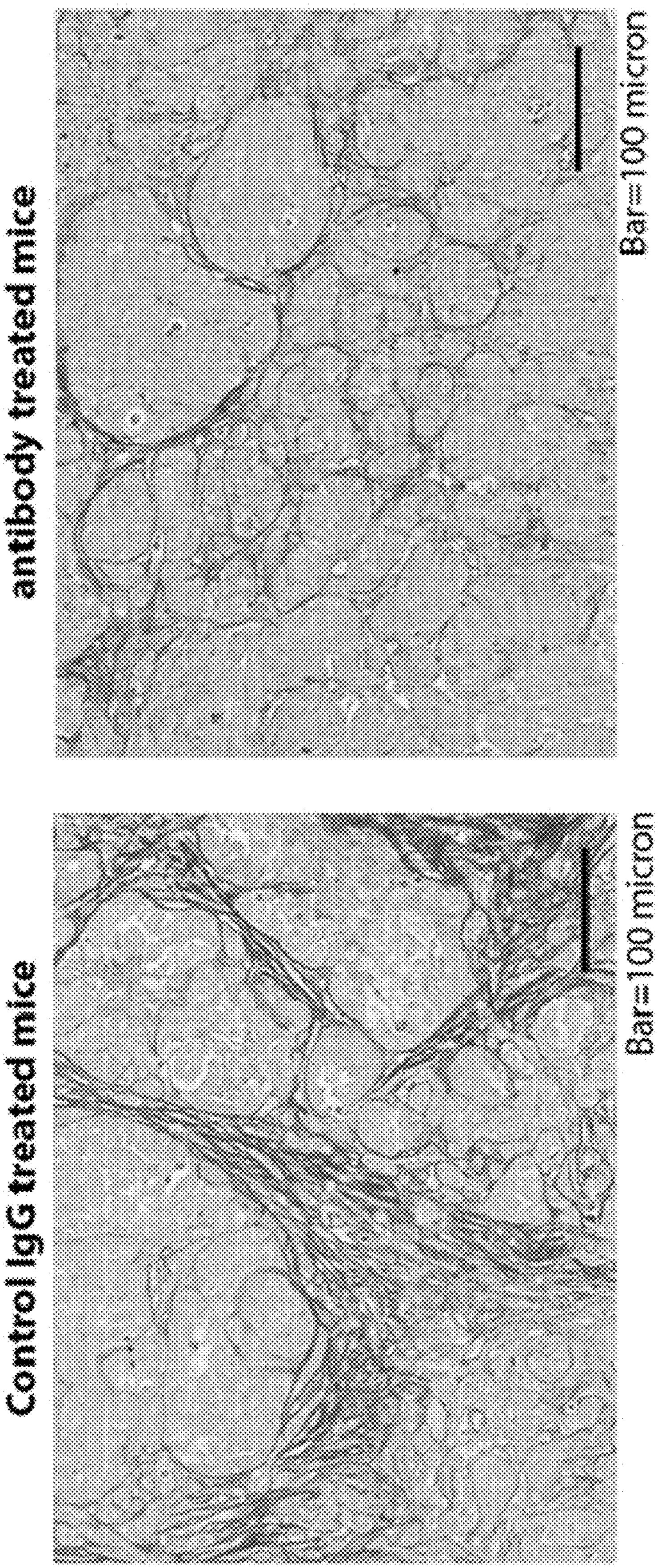
Figure 11F:
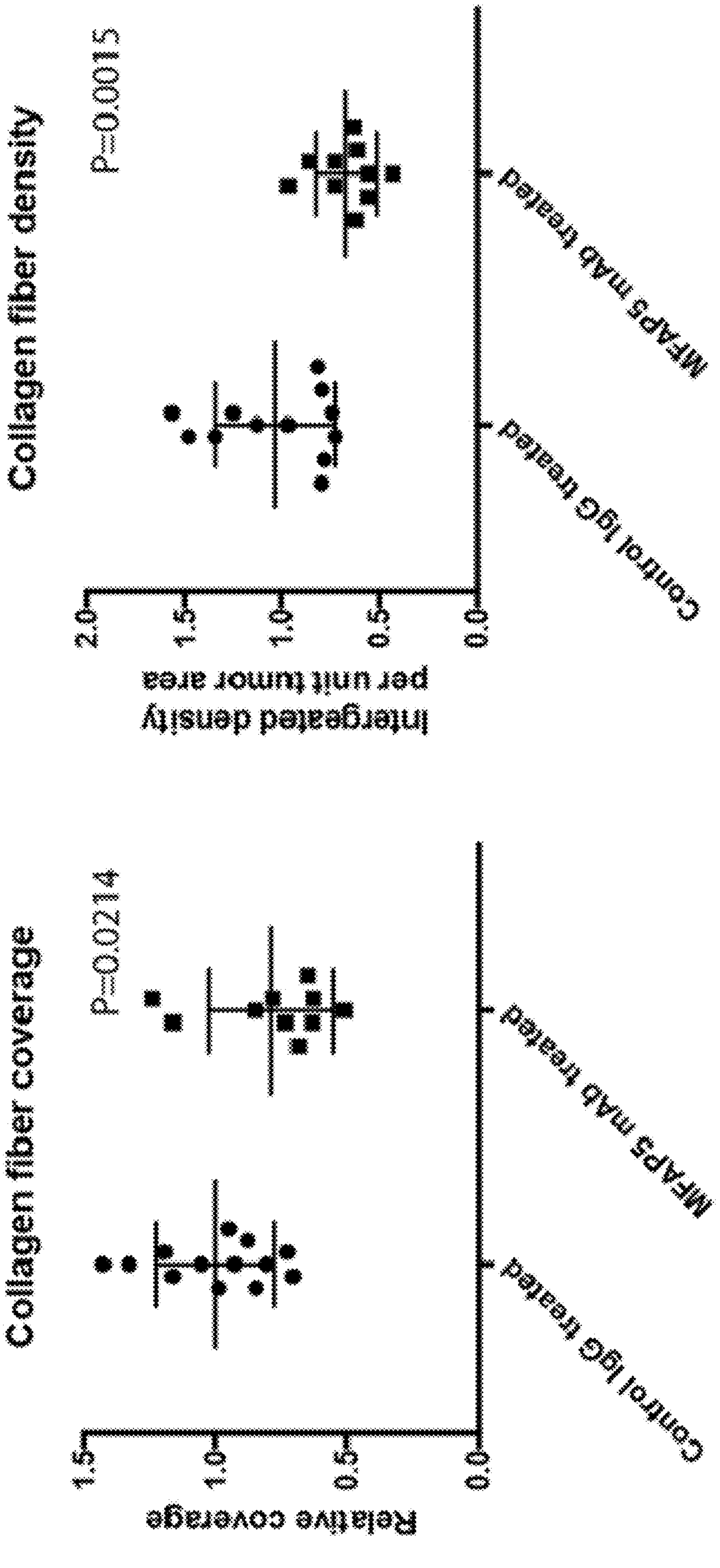
Figure 11G:
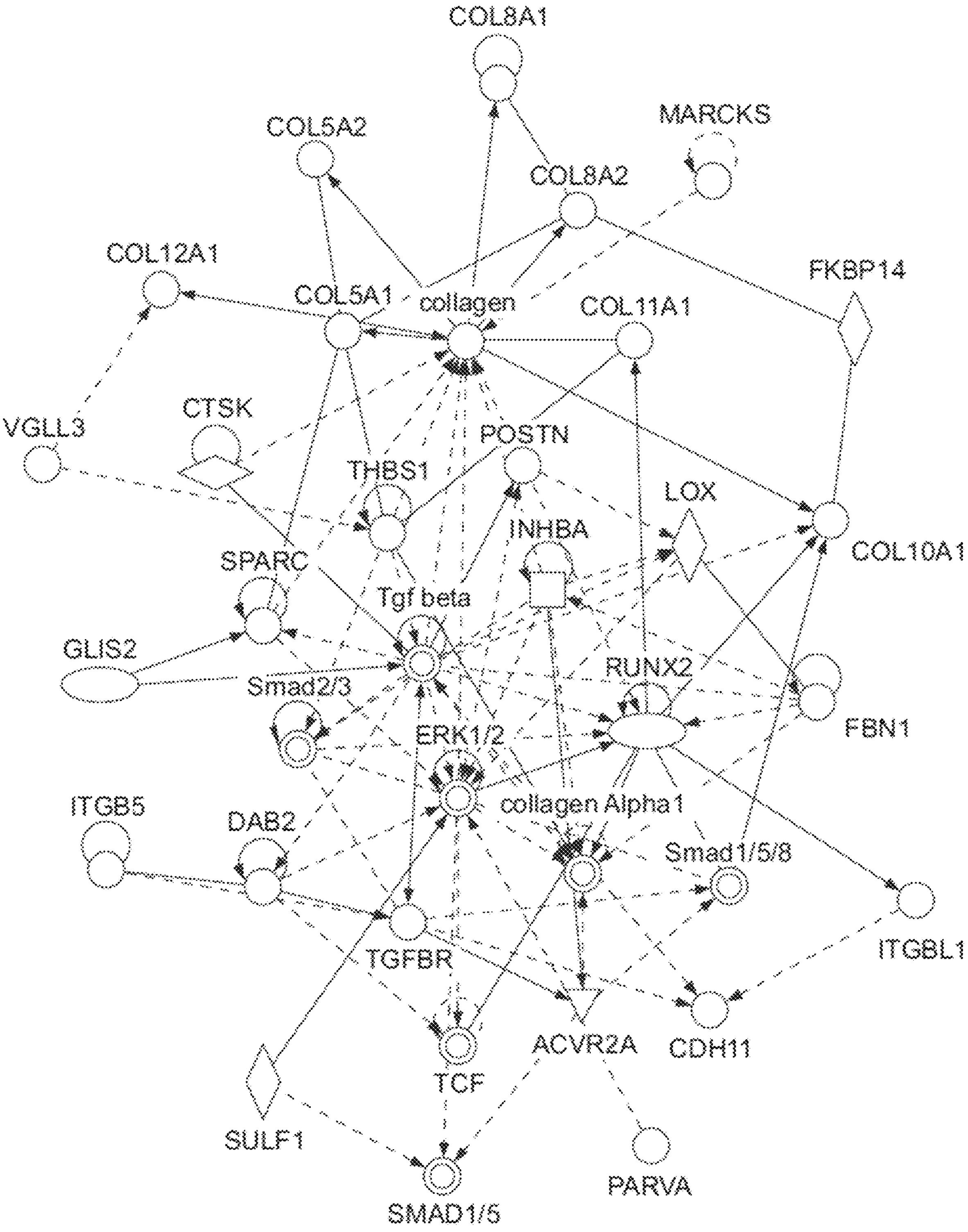

In addition to tumor angiogenesis, mediators secreted by CAFs, which constitute the fibrotic microenvironment, have also been shown to be associated with tumor progression and increased chemoresistance (McCarroll et al., 2014; Shields et al., 2012; Yazdani et al., 2017; Correia and Bissell, 2012). To evaluate the prognostic significance of a fibrotic microenvironment in ovarian cancer tissue, correlation studies between the fibrotic gene signature in microdissected CAFs in ovarian tumor tissue samples and patient survival rates were performed. The results showed that patients whose cancer stroma had the fibrotic gene signature (See Table 1 in Appendix 1 of U.S. Provisional Patent Application No. 62/877,298) had significantly lower survival rates (FIG. 11E).

Ovarian cancer patients expressing high level of fibrotic genes had a median survival duration of 19 months (95% CI=12.3–25.7 months), whereas patients expressing low level of fibrotic genes had a median survival duration of 33 months (95% CI=22.0–44.0 months) (P=0.017). To further determine whether MFAP5 blockade by the 130A antibody could reduce fibrosis in tumors developed from both ovarian and pancreatic mouse models, Picrosirius red staining, which is used for the visualization of collagen fibers, was first performed on tumor tissues obtained from mice treated with 130A or the control IgG. The results showed that tumors in treated mice had significantly lower Picrosirius red staining coverage and intensity in cancer associated stromal tissue than in control group (FIG. 11 F and FIG. 16A, FIG. 16B, FIG. 16C, and FIG. 16D). These data suggest that MFAP5 blockade inhibits fibrosis in both ovarian and pancreatic tumor tissues expression, and MFAP5 may regulate genes associated with fibrosis in CAFs in an autocrine fashion. To test this hypothesis, Pearson Correlation studies were performed on expression levels of MFAP5 and other genes using transcriptome generated from microdissected CAFs. Expression of 176 genes was identified, which demonstrated significant positive correlation with MFAP5 expression in CAFs (Pearson correlation coefficient>0.7, Pearson correlation P values and Benjamini-Hochberg adjusted P values<0.05) (Table 2).

TABLE 2

CORRELATION ANALYSIS

| Gene_Symbol | Pearson Correlation Coefficient | Pearson Correlation p-value | Bonferroni Adjusted p-value | Benj-Hoch Adjusted p-value |
|---|---|---|---|---|
| COL11A1 | 0.872875468 | 4.85E−20 | 1.09E−15 | 5.45E−16 |
| COL12A1 | 0.855887402 | 1.53E−18 | 3.43E−14 | 1.14E−14 |
| KIF26B | 0.842465533 | 1.73E−17 | 3.89E−13 | 9.73E−14 |
| FBN1 | 0.83695912 | 4.39E−17 | 9.88E−13 | 1.98E−13 |
| FZD1 | 0.833537039 | 7.70E−17 | 1.73E−12 | 2.89E−13 |
| GALNT1 | 0.831091362 | 1.14E−16 | 2.57E−12 | 3.27E−13 |
| GJB2 | 0.830981235 | 1.16E−16 | 2.61E−12 | 3.27E−13 |
| RUNX2 | 0.827522238 | 2.01E−16 | 4.51E−12 | 5.01E−13 |
| SPET11 | 0.823861721 | 3.53E−16 | 7.93E−12 | 7.93E−13 |
| THBS1 | 0.818654309 | 7.70E−16 | 1.73E−11 | 1.57E−12 |
| C1QTNF3 | 0.818022027 | 8.46E−16 | 1.90E−11 | 1.58E−12 |
| CHSY3 | 0.814352192 | 1.44E−15 | 3.24E−11 | 2.49E−12 |
| CCPG1///DYX1C1-CCPG1 | 0.808134074 | 3.47E−15 | 7.80E−11 | 5.26E−12 |
| FKBP14 | 0.80805137 | 3.51E−15 | 7.89E−11 | 5.26E−12 |
| ADAM12 | 0.806495829 | 4.35E−15 | 9.78E−11 | 5.60E−12 |
| HSD17B6 | 0.806464083 | 4.37E−15 | 9.82E−11 | 5.60E−12 |
| LUM | 0.806280639 | 4.48E−15 | 1.01E−10 | 5.60E−12 |
| SGMS2 | 0.802907685 | 7.08E−15 | 1.59E−10 | 8.38E−12 |
| ALDH1L2 | 0.79901147 | 1.19E−14 | 2.67E−10 | 1.34E−11 |
| GLT8D2 | 0.792752017 | 2.67E−14 | 6.01E−10 | 2.86E−11 |
| COL5A2 | 0.791731609 | 3.04E−14 | 6.84E−10 | 3.11E−11 |
| EVI2A | 0.791378676 | 3.18E−14 | 7.15E−10 | 3.11E−11 |
| LPAR1 | 0.789744687 | 3.90E−14 | 8.78E−10 | 3.54E−11 |
| LINC01614 | 0.789352618 | 4.10E−14 | 9.22E−10 | 3.54E−11 |
| TMEM2 | 0.789309657 | 4.12E−14 | 9.27E−10 | 3.54E−11 |
| ACVR2A | 0.789070191 | 4.25E−14 | 9.55E−10 | 3.54E−11 |
| TMEM158 | 0.787737329 | 5.01E−14 | 1.13E−09 | 3.93E−11 |
| ZMAT3 | 0.787643505 | 5.07E−14 | 1.14E−09 | 3.93E−11 |
| CD109 | 0.78639544 | 5.91E−14 | 1.33E−09 | 4.43E−11 |
| CLMP | 0.786077812 | 6.14E−14 | 1.38E−09 | 4.46E−11 |
| CDR2///LOC101060399 | 0.784218027 | 7.71E−14 | 1.73E−09 | 5.42E−11 |
| ASPN | 0.783891448 | 8.02E−14 | 1.80E−09 | 5.47E−11 |
| SULF1 | 0.782485156 | 9.51E−14 | 2.14E−09 | 6.29E−11 |
| INHBA | 0.782244538 | 9.78E−14 | 2.20E−09 | 6.29E−11 |
| PLPP4 | 0.78188097 | 1.02E−13 | 2.30E−09 | 6.38E−11 |
| FRMD6 | 0.781175345 | 1.11E−13 | 2.50E−09 | 6.76E−11 |
| PLPPR4 | 0.779045815 | 1.43E−13 | 3.22E−09 | 8.46E−11 |
| NUAK1 | 0.778841303 | 1.47E−13 | 3.30E−09 | 8.46E−11 |
| SERTAD2 | 0.778481345 | 1.53E−13 | 3.44E−09 | 8.61E−11 |
| LOX | 0.778145532 | 1.59E−13 | 3.58E−09 | 8.73E−11 |
| FNDC1 | 0.777389673 | 1.74E−13 | 3.91E−09 | 9.32E−11 |
| VGLL3 | 0.773456237 | 2.75E−13 | 6.18E−09 | 1.44E−10 |
| COL8A1 | 0.771505187 | 3.43E−13 | 7.72E−09 | 1.75E−10 |
| PRSS23 | 0.769773546 | 4.18E−13 | 9.39E−09 | 2.09E−10 |
| ITGBL1 | 0.769238769 | 4.43E−13 | 9.97E−09 | 2.17E−10 |
| GNB4 | 0.768909219 | 4.60E−13 | 1.03E−08 | 2.20E−10 |
| ITGB5 | 0.766624532 | 5.94E−13 | 1.34E−08 | 2.78E−10 |
| EPYC | 0.766081779 | 6.31E−13 | 1.42E−08 | 2.89E−10 |

TABLE 2-continued

CORRELATION ANALYSIS

| Gene_Symbol | Pearson Correlation Coefficient | Pearson Correlation p-value | Bonferroni Adjusted p-value | Benj-Hoch Adjusted p-value |
|---|---|---|---|---|
| PLXDC2 | 0.765627694 | 6.63E−13 | 1.49E−08 | 2.98E−10 |
| PCDH7 | 0.764467791 | 7.53E−13 | 1.69E−08 | 3.32E−10 |
| MARCKS | 0.764108199 | 7.84E−13 | 1.76E−08 | 3.34E−10 |
| ST6GALNAC5 | 0.764067074 | 7.87E−13 | 1.77E−08 | 3.34E−10 |
| SMYD3 | 0.76332283 | 8.54E−13 | 1.92E−08 | 3.55E−10 |
| TIMP3 | 0.763161374 | 8.69E−13 | 1.95E−08 | 3.55E−10 |
| MSRB3 | 0.762961013 | 8.88E−13 | 2.00E−08 | 3.57E−10 |
| NT5E | 0.762685395 | 9.15E−13 | 2.06E−08 | 3.57E−10 |
| XYLT1 | 0.762629112 | 9.21E−13 | 2.07E−08 | 3.57E−10 |
| GXYLT2 | 0.761461003 | 1.05E−12 | 2.35E−08 | 3.98E−10 |
| ENPP1 | 0.759920497 | 1.23E−12 | 2.77E−08 | 4.62E−10 |
| ACSL1 | 0.759654942 | 1.27E−12 | 2.86E−08 | 4.68E−10 |
| VCAN | 0.758047784 | 1.51E−12 | 3.39E−08 | 5.47E−10 |
| DEPDC7 | 0.756838111 | 1.71E−12 | 3.85E−08 | 6.12E−10 |
| PDGFRL | 0.755780929 | 1.92E−12 | 4.31E−08 | 6.73E−10 |
| MICAL2 | 0.754536581 | 2.18E−12 | 4.91E−08 | 7.36E−10 |
| PLAU | 0.754532353 | 2.18E−12 | 4.91E−08 | 7.36E−10 |
| PTPRD | 0.754435726 | 2.21E−12 | 4.96E−08 | 7.36E−10 |
| CLIC4 | 0.754311267 | 2.24E−12 | 5.03E−08 | 7.36E−10 |
| STK17B | 0.754212109 | 2.26E−12 | 5.08E−08 | 7.36E−10 |
| CTSK | 0.75401214 | 2.31E−12 | 5.19E−08 | 7.41E−10 |
| ANTXR1 | 0.753284953 | 2.49E−12 | 5.59E−08 | 7.74E−10 |
| GPR137B | 0.753274951 | 2.49E−12 | 5.60E−08 | 7.74E−10 |
| SLC44A1 | 0.753192946 | 2.51E−12 | 5.65E−08 | 7.74E−10 |
| SLC2A10 | 0.753024947 | 2.56E−12 | 5.75E−08 | 7.77E−10 |
| TRIM59 | 0.750781209 | 3.22E−12 | 7.25E−08 | 9.56E−10 |
| SDC1 | 0.750757969 | 3.23E−12 | 7.26E−08 | 9.56E−10 |
| DAB2 | 0.750514715 | 3.31E−12 | 7.45E−08 | 9.67E−10 |
| CLEC2B | 0.749496951 | 3.68E−12 | 8.27E−08 | 1.06E−09 |
| FAM107B | 0.749265546 | 3.76E−12 | 8.46E−08 | 1.07E−09 |
| SHISA2 | 0.748065745 | 4.25E−12 | 9.56E−08 | 1.20E−09 |
| KATNAL1 | 0.747809354 | 4.37E−12 | 9.82E−08 | 1.21E−09 |
| LRRC15 | 0.745324244 | 5.61E−12 | 1.26E−07 | 1.54E−09 |
| COPZ2 | 0.744940562 | 5.83E−12 | 1.31E−07 | 1.58E−09 |
| PARVA | 0.743802699 | 6.53E−12 | 1.47E−07 | 1.75E−09 |
| SPAG9 | 0.742880214 | 7.15E−12 | 1.61E−07 | 1.89E−09 |
| SMIM3 | 0.742793849 | 7.22E−12 | 1.62E−07 | 1.89E−09 |
| SLC12A8 | 0.74255843 | 7.39E−12 | 1.66E−07 | 1.91E−09 |
| COLEC12 | 0.740932913 | 8.67E−12 | 1.95E−07 | 2.21E−09 |
| CDH11 | 0.740393377 | 9.14E−12 | 2.06E−07 | 2.31E−09 |
| DYNLT3 | 0.74026145 | 9.26E−12 | 2.08E−07 | 2.31E−09 |
| CASK | 0.739439609 | 1.00E−11 | 2.26E−07 | 2.48E−09 |
| KDELR3 | 0.737959955 | 1.16E−11 | 2.60E−07 | 2.83E−09 |
| WSB2 | 0.737051349 | 1.26E−11 | 2.84E−07 | 3.05E−09 |
| COL10A1 | 0.736974445 | 1.27E−11 | 2.87E−07 | 3.05E−09 |
| MFAP3L | 0.736851088 | 1.29E−11 | 2.90E−07 | 3.05E−09 |
| SUGCT | 0.736618168 | 1.32E−11 | 2.97E−07 | 3.09E−09 |
| RCAN1 | 0.734896265 | 1.56E−11 | 3.50E−07 | 3.53E−09 |
| NDFIP2 | 0.734853428 | 1.56E−11 | 3.51E−07 | 3.53E−09 |
| EMB | 0.73479937 | 1.57E−11 | 3.53E−07 | 3.53E−09 |
| SMCO4 | 0.734698821 | 1.59E−11 | 3.56E−07 | 3.53E−09 |
| PRRX1 | 0.734694042 | 1.59E−11 | 3.57E−07 | 3.53E−09 |
| CCDC80///LINC01279 | 0.734581634 | 1.60E−11 | 3.60E−07 | 3.53E−09 |
| NTM | 0.734364866 | 1.64E−11 | 3.68E−07 | 3.57E−09 |
| RIC1 | 0.731916681 | 2.06E−11 | 4.64E−07 | 4.46E−09 |
| WDR41 | 0.730506334 | 2.36E−11 | 5.30E−07 | 5.05E−09 |
| TMEM47 | 0.730101976 | 2.45E−11 | 5.50E−07 | 5.19E−09 |
| P4HA1 | 0.729158317 | 2.67E−11 | 6.01E−07 | 5.62E−09 |
| YIPF5 | 0.728973996 | 2.72E−11 | 6.11E−07 | 5.66E−09 |
| TUBB2A | 0.728439575 | 2.86E−11 | 6.43E−07 | 5.90E−09 |
| CRISPLD2 | 0.728241672 | 2.91E−11 | 6.55E−07 | 5.95E−09 |
| SFRP2 | 0.727571231 | 3.10E−11 | 6.96E−07 | 6.27E−09 |
| CCDC80 | 0.726712025 | 3.35E−11 | 7.54E−07 | 6.73E−09 |
| SNX7 | 0.726537894 | 3.41E−11 | 7.66E−07 | 6.78E−09 |
| CSGALNACT2 | 0.726189697 | 3.52E−11 | 7.91E−07 | 6.94E−09 |
| TMEM165 | 0.72556899 | 3.72E−11 | 8.37E−07 | 7.21E−09 |
| COL8A2 | 0.725498287 | 3.75E−11 | 8.43E−07 | 7.21E−09 |
| C3orf80 | 0.72548588 | 3.75E−11 | 8.44E−07 | 7.21E−09 |
| RAB23 | 0.725086348 | 3.89E−11 | 8.75E−07 | 7.42E−09 |
| UHRF1BP1L | 0.723881718 | 4.35E−11 | 9.77E−07 | 8.21E−09 |
| INPP5F | 0.723765426 | 4.39E−11 | 9.87E−07 | 8.23E−09 |
| WIPF1 | 0.723591081 | 4.46E−11 | 1.00E−06 | 8.29E−09 |
| ATL1 | 0.723444636 | 4.52E−11 | 1.02E−06 | 8.33E−09 |

TABLE 2-continued

CORRELATION ANALYSIS

| Gene_Symbol | Pearson Correlation Coefficient | Pearson Correlation p-value | Bonferroni Adjusted p-value | Benj-Hoch Adjusted p-value |
|---|---|---|---|---|
| ALDH18A1 | 0.723298854 | 4.58E−11 | 1.03E−06 | 8.38E−09 |
| GLIS2 | 0.722788593 | 4.80E−11 | 1.08E−06 | 8.70E−09 |
| P4HA2 | 0.722561097 | 4.90E−11 | 1.10E−06 | 8.81E−09 |
| PPIC | 0.721617976 | 5.33E−11 | 1.20E−06 | 9.52E−09 |
| NNMT | 0.721341404 | 5.47E−11 | 1.23E−06 | 9.68E−09 |
| GLIPR1 | 0.720978845 | 5.65E−11 | 1.27E−06 | 9.92E−09 |
| PNMA2 | 0.720816821 | 5.73E−11 | 1.29E−06 | 9.92E−09 |
| COL5A1 | 0.720814227 | 5.73E−11 | 1.29E−06 | 9.92E−09 |
| IKBIP | 0.720574159 | 5.86E−11 | 1.32E−06 | 1.01E−08 |
| TICAM2///TMED7-TICAM2 | 0.720363183 | 5.97E−11 | 1.34E−06 | 1.02E−08 |
| POSTN | 0.720011869 | 6.16E−11 | 1.39E−06 | 1.04E−08 |
| TPBG | 0.719420774 | 6.50E−11 | 1.46E−06 | 1.09E−08 |
| PRICKLE1 | 0.719315073 | 6.56E−11 | 1.47E−06 | 1.09E−08 |
| GPC4 | 0.71893127 | 6.79E−11 | 1.53E−06 | 1.12E−08 |
| GPX8 | 0.718661493 | 6.95E−11 | 1.56E−06 | 1.14E−08 |
| TNFSF4 | 0.718344037 | 7.15E−11 | 1.61E−06 | 1.16E−08 |
| MLLT11 | 0.718242175 | 7.22E−11 | 1.62E−06 | 1.16E−08 |
| STK17A | 0.718218665 | 7.23E−11 | 1.63E−06 | 1.16E−08 |
| THBS2 | 0.718152363 | 7.27E−11 | 1.64E−06 | 1.16E−08 |
| SPARC | 0.718114958 | 7.30E−11 | 1.64E−06 | 1.16E−08 |
| KDSR | 0.716854435 | 8.16E−11 | 1.83E−06 | 1.28E−08 |
| TANC2 | 0.715318424 | 9.34E−11 | 2.10E−06 | 1.46E−08 |
| DOCK11 | 0.715050847 | 9.56E−11 | 2.15E−06 | 1.48E−08 |
| MOXD1 | 0.715010541 | 9.60E−11 | 2.16E−06 | 1.48E−08 |
| FAM69A | 0.714842975 | 9.74E−11 | 2.19E−06 | 1.49E−08 |
| MAN2A1 | 0.714668637 | 9.89E−11 | 2.22E−06 | 1.50E−08 |
| CEMIP | 0.714233372 | 1.03E−10 | 2.31E−06 | 1.55E−08 |
| NAT1 | 0.713295339 | 1.11E−10 | 2.51E−06 | 1.67E−08 |
| UTP14C | 0.713046546 | 1.14E−10 | 2.56E−06 | 1.70E−08 |
| PRKG1 | 0.712614599 | 1.18E−10 | 2.66E−06 | 1.75E−08 |
| FUT11 | 0.712464775 | 1.20E−10 | 2.69E−06 | 1.76E−08 |
| ATP10D | 0.711333241 | 1.32E−10 | 2.97E−06 | 1.91E−08 |
| KDELR2 | 0.711278672 | 1.33E−10 | 2.98E−06 | 1.91E−08 |
| C6orf120 | 0.710949198 | 1.37E−10 | 3.07E−06 | 1.96E−08 |
| PPP3CA | 0.710463468 | 1.42E−10 | 3.20E−06 | 2.03E−08 |
| HS3ST3B1 | 0.709565027 | 1.54E−10 | 3.46E−06 | 2.18E−08 |
| C12orf75 | 0.708020429 | 1.75E−10 | 3.95E−06 | 2.47E−08 |
| GAS1 | 0.706880483 | 1.93E−10 | 4.35E−06 | 2.70E−08 |
| ANKRD13C | 0.706409329 | 2.01E−10 | 4.52E−06 | 2.79E−08 |
| FNIP2 | 0.706137534 | 2.06E−10 | 4.63E−06 | 2.84E−08 |
| PTS | 0.705983388 | 2.09E−10 | 4.69E−06 | 2.86E−08 |
| GFPT1 | 0.705154485 | 2.24E−10 | 5.03E−06 | 3.05E−08 |
| HCFC2 | 0.705090252 | 2.25E−10 | 5.06E−06 | 3.05E−08 |
| FKBP7 | 0.704877285 | 2.29E−10 | 5.15E−06 | 3.08E−08 |
| CTHRC1 | 0.704494363 | 2.36E−10 | 5.31E−06 | 3.16E−08 |
| DNAJB4 | 0.703825659 | 2.50E−10 | 5.62E−06 | 3.33E−08 |
| DSE | 0.702916888 | 2.70E−10 | 6.06E−06 | 3.56E−08 |
| BCAR3 | 0.702825686 | 2.72E−10 | 6.11E−06 | 3.56E−08 |
| PICALM | 0.70268021 | 2.75E−10 | 6.18E−06 | 3.56E−08 |
| GJA1 | 0.702672913 | 2.75E−10 | 6.19E−06 | 3.56E−08 |
| MAGEL2 | 0.70265394 | 2.76E−10 | 6.20E−06 | 3.56E−08 |
| TMTC3 | 0.702392848 | 2.82E−10 | 6.33E−06 | 3.62E−08 |
| DIP2C | 0.701772387 | 2.97E−10 | 6.67E−06 | 3.79E−08 |
| TMEM200A | 0.700708332 | 3.24E−10 | 7.28E−06 | 4.11E−08 |
| GPC6 | 0.700473082 | 3.30E−10 | 7.43E−06 | 4.17E−08 |

Figure 11H:
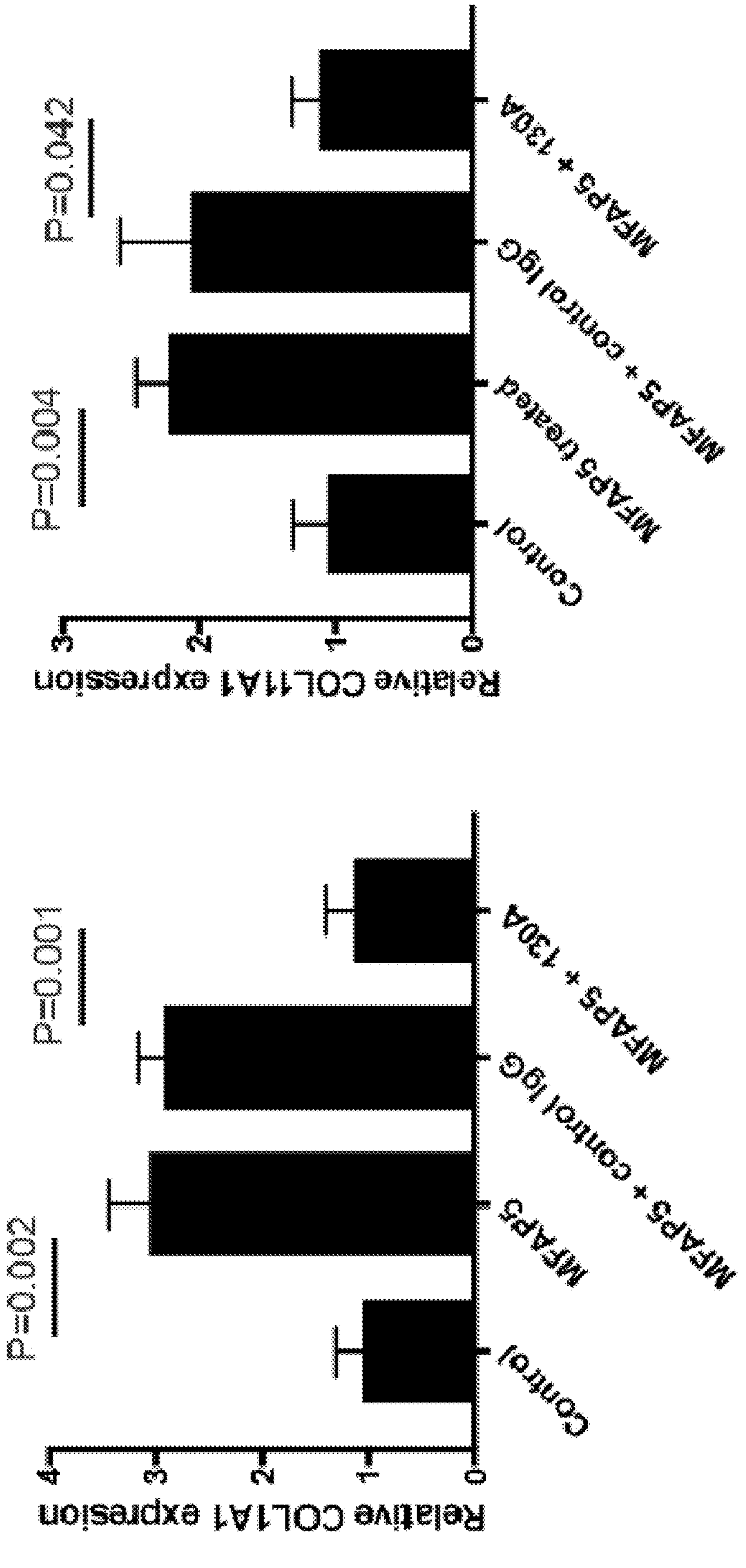

Further analysis on the 176 genes using the Ingenuity Pathway Analysis software program identified a collagen enriched key signaling network, which is involved in extracellular matrix and connective tissue disorder (FIG. 11G), suggesting that high MFAP5 expressed by CAFs may contribute to a collagen rich, fibrotic tumor microenvironment. To further determine whether MFAP5 regulates the expression of key fibrosis-related genes in CAFs, qRT-PCR analyses on two of the key fibrosis-related genes, COL1A1 and COL11A1, whose expression showed significant correlation with MFAP5 expression in CAF, were performed on human fibroblasts treated with exogenous MFAP5. The results showed markedly higher expression of COL1A1 and COL11A1 in fibroblasts treated with MFAP5 than those treated with the control solvent (FIG. 11H). In addition, CAFs treated with MFAP5 in the presence of 130A anti-MFAP5 antibody demonstrated significantly lower levels of COL1A1 and COL11A1 expression than those treated with MFAP5 in the presence of control IgG (FIG. 11H). These data suggest that MFAP5 up-regulates COL1A1 and COL11A1 in CAFs in an autocrine manner.

DISCUSSION

In this study, the development of an anti-MFAP5 monoclonal antibody which could down-regulate MFAP5-induced collagen production in CAFs, suppress intratumoral microvessel leakiness, and enhance paclitaxel bioavailability in both ovarian and pancreatic cancer models was demonstrated. MFAP5 is a pro-tumorigenic and pro-angiogenic protein, which is up-regulated in CAFs in both ovarian and pancreatic cancer patients. Previous studies on MFAP5 demonstrated its crucial roles in promoting ovarian tumor metastasis, stimulating tumor angiogenesis and enhancing cancer cells' resistance to chemotherapeutic agent through the reduction in drug delivery via the tumor vascular system (Leung et al., 2014; Leung et al., 2018). In the present study, treating tumor-bearing mice with a newly developed MFAP5-targeting MAb suppressed ovarian and pancreatic tumors progression with no observable toxic effects. Based on The Human Protein Atlas constructed by Uhlen and colleagues (2005; 2010), MFAP5 expression was detected only in 1 out of 81 analyzed normal tissue cell types at an expression level of medium level or higher. mRNA analyses showed that MFAP5 is expressed by about 50% of fibrosarcoma and normal fibroblasts during wound healing. On the other hand, MFAP5 expression was detected in 75 out of 80 analyzed normal tissue cell types at medium or high levels (Uhlen et al., 2005; Uhlen et al., 2010). The endogenous low expression level of MFAP5 in normal tissues may have contributed to the low treatment-related toxicity observed in the animal studies. Furthermore, these data demonstrated increased paclitaxel delivery after treating ovarian tumors with an anti-MFAP5 monoclonal antibody and that combining paclitaxel with that antibody improved the efficacy of paclitaxel in ovarian cancer treatment, indicating that targeting stromal MFAP5 with MAbs can potentiate the therapeutic efficacy of cancer chemotherapy.

The idea that therapeutic antibodies could serve as "magic bullets" in cancer therapy has a long history and achieved noticeable success in recent years. The current anti-MFAP5 antibody clones could be further modified as immunoconjugate therapy by conjugation with drugs, toxins or radioisotopes to carry enhanced killing capacity directly to the tumors. While treatment efficacy could be context specific, CAF-targeting for cancer treatment is believed to have two benefits:

(1) the continuous support from CAFs is critical to tumor progression; and (2) stromal cells, including CAFs, are genetically more stable than cancer cells, which can accumulate adaptive mutations during drug treatment to acquire resistance (Micke and Ostman, 2004; Joyce, 2005; Yeung et al., 2015).

On the other hand, chimeric or humanized anti-MFAP5 MAbs could be developed. These humanized or chimeric MAbs have a longer half-life in the patient's bloodstream and enable better interactions with human effector cells in the patients (Oldham and Dillman, 2008). Although the anti-MFAP5 MAbs generated have $K_D$ values in the low nanomolar range ($10^{-9}$) (indicating high affinity levels), these values can likely be further improved by performing additional optimization, such as affinity maturation.

This is the first report demonstrating that MFAP5 blockade reduced fibrosis in both ovarian and pancreatic cancers through down-regulation of fibrosis-related genes including COL1A1 and COL11A1. Fibrosis in tumor tissue has been shown to increase tissue matrix stiffness, which promotes tumor progression and confers chemoresistance (Joyce et al, 2018; Cox and Erler, 2011; Barcus et al, 2013). Fibrosis-related genes such as COL11A1 has been shown to confer cisplatin resistance in ovarian cancer cells (Rada et al, 2018). These data suggest that that MFAP5 blockade suppresses fibrosis through down-regulating of fibrosis-related genes such as COL11A1 as observed in this study, which subsequently enhances chemosensitivity of cancer cells. These data also demonstrated for the first time that MFAP5 transcriptionally up-regulated fibrosis-related genes, including COL1A1 and COL11A.

While the molecular mechanism by which MFAP5 regulates these collagen genes in CAFs remain to be elucidated, it is likely that MFAP5 may bind to $\alpha_v\beta_3$ integrin, which subsequently activates collagen genes through integrin/ERK mediated signaling pathways as described previously (Leung et al., 2014; Mok et al., 2009; Leung et al., 2018). In fact, activation of $\alpha_v\beta_3$/ERK signaling pathway by TGF-beta has been shown to activate collagen genes in fibroblasts (Asano et al, 2005). In additional to cancer, many diseases involve fibrotic conditions. Further evaluation on whether MFAP5 also plays a role in the excess formation of fibrous tissue in other diseases and whether MFAP5-targeting therapy could offer additional opportunities for clinical application of the MAb compositions disclosed herein.

In conclusion, the present example demonstrates that targeting MFAP5 using newly-developed antibody compositions such as 130A can successfully block the downstream signaling network mediated by MFAP5, and subsequently inhibit ovarian and pancreatic cancer progression, as well as promote chemosensitivity and reduce fibrosis.

Example 2—Affinity Measurement Report

Affinity of U8369DJ230-Ag to chimeric antibody (mouse-human chimeric) was measured using the Biacore 8K system.

Materials

Instrument: Biacore 8K;

Sensor chip: Series S Sensor Chip Protein A;

Running buffer: 1×HBS-EP+ (10 mM HEPES, 150 mM NaCl, 3 mM EDTA, 0.05% P20, pH 7.4);

Temperature: 25° C.;

Ligand: U8369DJ230-Ag;

Analyte: chimeric antibody.

Methods

TABLE 3

| BIACORE PARAMETERS | |
|---|---|
| **Immobilization** | |
| Ligand | U8369DJ230-Ag |
| Immobilization level (RU) | ~700 |
| **Association & Dissociation** | |
| Association contact time (sec) | 150 |
| Dissociation contact time (sec) | 360 |
| Flow rate (μL/min) | 30 |
| Sample concentrations (nM) | 3.125, 6.25, 12.5, 25, 50, 100 |

Results

Figure 17A:
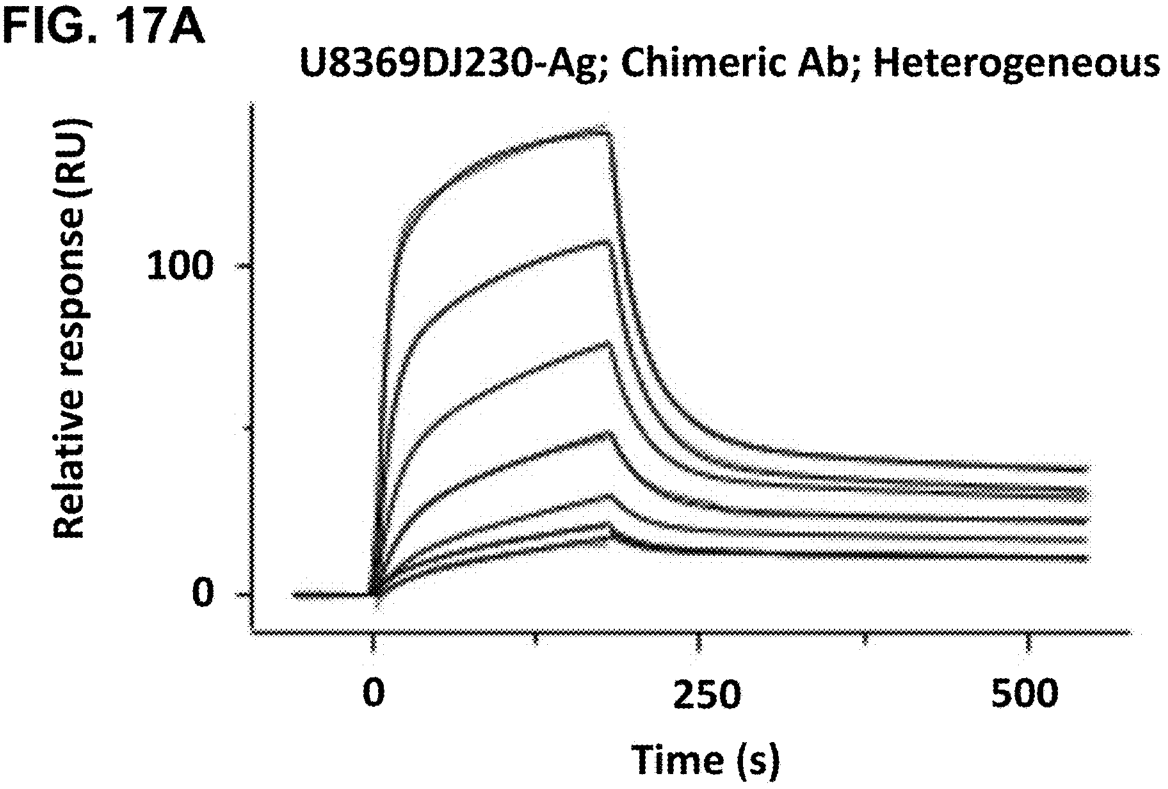
FIG. 17A and FIG. 17B show Sensor-grams of U8369DJ230-Ag to chimeric antibody.
Figure 17B:
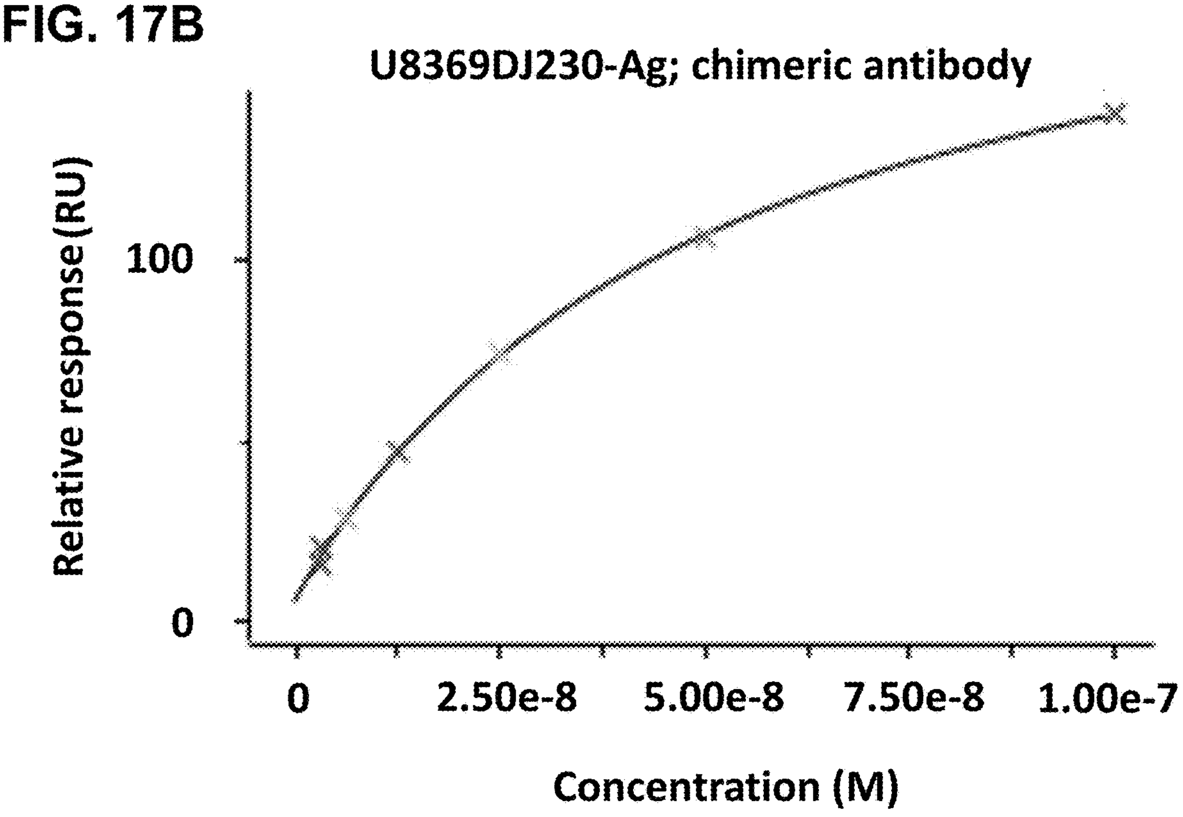

The affinity and kinetics U8369DJ230-Ag to chimeric antibody was summarized in Table 4, and the sensor-grams were determined and shown in FIG. 17A and FIG. 17B.

TABLE 4

AFFINITY AND KINETICS OF U8369DJ230-AG TO CHIMERIC ANTIBODY

| Fitting Model | Ligand | Analyte | Ka (1/Ms) | Kd (1/s) | KD (M) | $R_{max}$ | $Chi^2$ ($RU^2$) |
|---|---|---|---|---|---|---|---|
| Heterogeneous ligand | Chimeric Ab | U8369DJ230-Ag | $1.76 \times 10^6$ | $5.86 \times 10^{-2}$ | $3.32 \times 10^{-8}$ | 129.7 | $3.95 \times 10^{-1}$ |
| Steady-state affinity | Chimeric Ab | U8369DJ230-Ag | NA | NA | $4.90 \times 10^{-8}$ | 201.9 | NA |

REFERENCES

The following references, to the extent that they provide exemplary procedural or other details supplementary to those set forth herein, are specifically incorporated herein in their entirety by express reference thereto:

ALTSCHUL, S F et al., "Gapped BLAST and PSI-BLAST: a new generation of protein database search programs," *Nucl. Acids Res.,* 25(17):3389-3402 (September 1997).

ASANO, Y et al, "Increased expression of integrin alpha(v) beta3 contributes to the establishment of autocrine TGF-beta signaling in scleroderma fibroblasts," *J. Immunol.,* 175(11):7708-7718 (December 2005).

BARCUS, C E et al., "Stiff collagen matrices increase tumorigenic prolactin signaling in breast cancer cells," *J. Biol. Chem.,* 288(18):12722-12732 (May 2013).

BROUWERS, B et al., "The footprint of the ageing stroma in older patients with breast cancer," *Breast Cancer Res.,* 19(1):78 (December 2016).

COBLEIGH, M A et al., "Multinational study of the efficacy and safety of humanized anti-HER2 monoclonal antibody in women who have HER2-overexpressing metastatic breast cancer that has progressed after chemotherapy for metastatic disease," *J. Clin. Oncol.,* 17(9):2639-2648 (September 1999).

CORREIA, A L and BISSELL, MJ, "The tumor microenvironment is a dominant force in multidrug resistance," *Drug Resist. Update,* 15(1-2):39-49 (February-April 2012).

COX, T R and ERLER, J T, "Remodeling and homeostasis of the extracellular matrix: implications for fibrotic diseases and cancer," *Disease Model Mech.,* 4(2):165-178 (March 2011).

GOEL, S et al., "Vascular normalization as a therapeutic strategy for malignant and nonmalignant disease," *Cold Spring Harbor Perspect. Med.,* 2(3):a006486 (March 2012).

GRIBSKOV, M and BURGESS, R R, "Sigma factors from *E. coli, B. subtilis*, phage SP01, and phage T4 are homologous proteins," *Nucleic Acids Res.,* 14(16):6745-6763 (August 1986).

HALE, W G, and MARGHAM, J P, "*HARPER COLLINS DICTIONARY OF BIOLOGY*," HarperPerennial, New York (1991).

HARDMAN, J G, and LIMBIRD, L E, (Eds.), "*GOODMAN AND GILMAN'S THE PHARMACOLOGICAL BASIS OF THERAPEUTICS*" 10$^{th}$ Edition, McGraw-Hill, New York (2001).

H U, J et al., "Generation of a monoclonal antibody against the glycosylphosphatidylinositol-linked protein Rae-1 using genetically engineered tumor cells," *Biol. Proc. Online,* 16(1):3 (February 2014).

HURWITZ, H, "Integrating the anti-VEGF-A humanized monoclonal antibody bevacizumab with chemotherapy in advanced colorectal cancer," *Clin. Colorectal Cancer,* 4(Suppl 2):S62-S68 (October 2004).

JIA, Z et al., "Diagnosis of prostate cancer using differentially expressed genes in stroma," *Cancer Res.,* 71(7): 2476-2487 (April 2011).

JOYCE, J A, "Therapeutic targeting of the tumor microenvironment," *Cancer Cell,* 7(6):513-520 (June 2005).

JOYCE, M H et al., "Phenotypic basis for matrix stiffness-dependent chemoresistance of breast cancer cells to doxorubicin," *Front. Oncol.,* 8:337 (September 2018).

KYTE, J and DOOLITTLE, R F "A simple method for displaying the hydropathic character of a protein," *J. Mol. Biol.,* 157(1):105-132 (May 1982).

LEE, M M et al., "Synthesis of a fluorescent analogue of paclitaxel that selectively binds microtubules and sensitively detects efflux by P-glycoprotein," *Angew. Chem. Int. Ed. Engl.,* 56(24):6927-6931 (June 2017).

LEUNG, C S et al., "Calcium-dependent FAK/CREB/TNNC1 signalling mediates the effect of stromal MFAP5 on ovarian cancer metastatic potential," *Nature Communic.,* 5:5092 (October 2014).

LEUNG, C S et al., "Cancer-associated fibroblasts regulate endothelial adhesion protein LPP to promote ovarian cancer chemoresistance," *J. Clin. Invest.,* 128(2):589-606 (February 2018).

LOPEZ-CASAS, P P and LOPEZ-FERNANDEZ, L A, "Gene-expression profiling in pancreatic cancer," *Expert Rev. Mol. Diagn.,* 10(5):591-601 (July 2010).

MCCARROLL, J A et al., "Role of pancreatic stellate cells in chemoresistance in pancreatic cancer," *Front. Physiol.,* 5:141 (April 2014).

MICKE, P and OSTMAN, A, "Tumour-stroma interaction: cancer-associated fibroblasts as novel targets in anti-cancer therapy?" *Lung Cancer,* 45(Suppl 2):S163-S175 (August 2004).

MOK, S C et al., "A gene signature predictive for outcome in advanced ovarian cancer identifies a survival factor: microfibril-associated glycoprotein 2," *Cancer Cell,* 16(6):521-532 (December 2009).

NAVAB, R et al., "Prognostic gene-expression signature of carcinoma-associated fibroblasts in non-small cell lung cancer," *Proc. Nat'l. Acad. Sci. USA,* 108(17):7160-7165 (April 2011).

NEEDLEMAN, S B and WUNSCH, C D, "A general method applicable to the search for similarities in the amino acid sequence of two proteins," *J. Mol. Biol.,* 48(3):443-453 (March 1970).

OHLUND, D et al., "Distinct populations of inflammatory fibroblasts and myofibroblasts in pancreatic cancer," *J. Exp. Med.,* 214(3):579-596 (March 2017).

OLDHAM, R K and DILLMAN, R O, "Monoclonal antibodies in cancer therapy: 25 years of progress," *J. Clin. Oncol.,* 26(11):1774-1777 (April 2008).

POSTOW, M A et al., "Immune checkpoint blockade in cancer therapy," *J. Clin. Oncol.,* 33(17):1974-1982 (June 2015).

QIN, H et al., "Novel BAFF-receptor antibody to natively folded recombinant protein eliminates drug-resistant human B-cell malignancies in vivo," *Clin. Cancer Res.,* 24(5):1114-1123 (March 2018).

RADA, M et al., "Inhibitor of apoptosis proteins (IAPs) mediate collagen type XI alpha 1-driven cisplatin resistance in ovarian cancer," *Oncogene,* 37(35):4809-4820 (May 2018).

ROMOND, E H et al., "Trastuzumab plus adjuvant chemotherapy for operable HER2-positive breast cancer," *N. Engl. J. Med.,* 353(16):1673-1684 (October 2005).

SCHRODINGER 2013. Schrodinger, LLC: New York, NY (2013).

SHIELDS, M A et al., "Biochemical role of the collagen-rich tumour microenvironment in pancreatic cancer progression," *Biochem. J.,* 441(2):541-552 (January 2012).

SINGLETON, P and SAINSBURY, D, "*DICTIONARY OF MICROBIOLOGY AND MOLECULAR BIOLOGY,*" 2$^{nd}$ Ed., John Wiley and Sons, New York (1987).

SLAMON, D et al., "Adjuvant trastuzumab in HER2-positive breast cancer," *N. Engl. J. Med.,* 365(14):1273-1283 (October 2011).

TEWARI, K S et al., "Bevacizumab for advanced cervical cancer: final overall survival and adverse event analysis of a randomised, controlled, open-label, phase 3 trial (Gynecologic Oncology Group 240)," *Lancet,* 390(10103): 1654-1663 (July 2017).

TLSTY, T D and COUSSENS, L M, "Tumor stroma and regulation of cancer development," *Annu. Rev. Pathol. Mech. Dis.,* 1:119-150 (February 2006).

UHLEN, M et al., "A human protein atlas for normal and cancer tissues based on antibody proteomics," *Molec. Cell. Proteomics,* 4(12):1920-1932 (August 2005).

UHLEN, M et al., "A proposal for validation of antibodies," *Nat. Methods,* 13(10):823-827 (September 2016).

UHLEN, M et al., "Towards a knowledge-based human protein atlas," *Nat. Biotechnol.,* 28(12):1248-1250 (December 2010).

VOO, K S et al., "Antibodies targeting human OX40 expand effector T cells and block inducible and natural regulatory T cell function," *J. Immunol.,* 191(7):3641-3650 (September 2013).

YAZDANI, S et al., "Drug targeting to myofibroblasts: Implications for fibrosis and cancer," *Adv. Drug Deliv. Rev.,* 121:101-116 (July 2017).

YEUNG, T L et al., "Cellular and molecular processes in ovarian cancer metastasis. A review in the theme: cell and molecular processes in cancer metastasis," *Am. J. Physiol. Cell Physiol.,* 309(7):C444-C456 (July 2015).

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved.

All such similar substitutes and modifications apparent to those skilled in the art are deemed to be within the spirit, scope and concept of the invention as defined by the appended claims.

SEQUENCE LISTING

```
<160> NUMBER OF SEQ ID NOS: 27

<210> SEQ ID NO 1
<211> LENGTH: 173
<212> TYPE: PRT
<213> ORGANISM: Homo sapiens
<220> FEATURE:
<221> NAME/KEY: MISC_FEATURE
<222> LOCATION: (1)..()
<223> OTHER INFORMATION: amino acid sequence of the human MFAP5
      polypeptide (Homo sapiens, GenBank accession: AAH05901.1)

<400> SEQUENCE: 1

Met Ser Leu Leu Gly Pro Lys Val Leu Leu Phe Leu Ala Ala Phe Ile
1               5                   10                  15

Ile Thr Ser Asp Trp Ile Pro Leu Gly Val Asn Ser Gln Arg Gly Asp
            20                  25                  30

Asp Val Thr Gln Ala Thr Pro Glu Thr Phe Thr Glu Asp Pro Asn Leu
        35                  40                  45

Val Asn Asp Pro Ala Thr Asp Glu Thr Val Leu Ala Val Leu Ala Asp
    50                  55                  60

Ile Ala Pro Ser Thr Asp Asp Leu Ala Ser Leu Ser Glu Lys Asn Thr
65                  70                  75                  80

Thr Ala Glu Cys Trp Asp Glu Lys Phe Thr Cys Thr Arg Leu Tyr Ser
                85                  90                  95

Val His Arg Pro Val Lys Gln Cys Ile His Gln Leu Cys Phe Thr Ser
            100                 105                 110

Leu Arg Arg Met Tyr Ile Val Asn Lys Glu Ile Cys Ser Arg Leu Val
        115                 120                 125

Cys Lys Glu His Glu Ala Met Lys Asp Glu Leu Cys Arg Gln Met Ala
    130                 135                 140

Gly Leu Pro Pro Arg Arg Leu Arg Arg Ser Asn Tyr Phe Arg Leu Pro
145                 150                 155                 160

Pro Cys Glu Asn Val Asp Leu Gln Arg Pro Asn Gly Leu
                165                 170


<210> SEQ ID NO 2
<211> LENGTH: 164
<212> TYPE: PRT
<213> ORGANISM: Mus musculus
```

<220> FEATURE:
<221> NAME/KEY: MISC_FEATURE
<222> LOCATION: (1)..()
<223> OTHER INFORMATION: Amino Acid sequence of the murine Mfap5
      polypeptide (Mus musculus, GeneBank accession: AAH25131.1)

<400> SEQUENCE: 2

Met Leu Phe Leu Gly Gln Lys Ala Leu Leu Leu Val Leu Ala Val Ser
1               5                   10                  15

Ile Pro Ser Asp Trp Leu Pro Leu Gly Val Ser Gly Gln Arg Gly Asp
            20                  25                  30

Asp Val Pro Glu Thr Phe Thr Asp Asp Pro Asn Leu Val Asn Asp Pro
        35                  40                  45

Ser Thr Asp Asp Thr Ala Leu Ala Asp Ile Thr Pro Ser Thr Asp Asp
    50                  55                  60

Leu Ala Asp Asp Lys Asn Ala Thr Ala Glu Cys Arg Asp Glu Lys Phe
65                  70                  75                  80

Ala Cys Thr Arg Leu Tyr Ser Val His Arg Pro Val Arg Gln Cys Val
                85                  90                  95

His Gln Ser Cys Phe Thr Ser Leu Arg Arg Met Tyr Ile Ile Asn Asn
            100                 105                 110

Glu Ile Cys Ser Arg Leu Val Cys Lys Glu His Glu Ala Met Lys Asp
        115                 120                 125

Glu Leu Cys Arg Gln Met Ala Gly Leu Pro Pro Arg Arg Leu Arg Arg
    130                 135                 140

Ser Asn Tyr Phe Arg Leu Pro Pro Cys Glu Asn Met Asn Leu Gln Arg
145                 150                 155                 160

Pro Asp Gly Leu

<210> SEQ ID NO 3
<211> LENGTH: 9
<212> TYPE: PRT
<213> ORGANISM: Unknown
<220> FEATURE:
<223> OTHER INFORMATION: exemplary MFAP5-specific peptide epitope

<400> SEQUENCE: 3

Asp Glu Thr Val Leu Ala Val Leu Ala
1               5

<210> SEQ ID NO 4
<211> LENGTH: 12
<212> TYPE: PRT
<213> ORGANISM: Unknown
<220> FEATURE:
<223> OTHER INFORMATION: Exemplary consensus peptide having the amino
      acid sequence “LCRQMAGLPPRR” that is common to both the human and
      the marine MFAP5 proteins.

<400> SEQUENCE: 4

Leu Cys Arg Gln Met Ala Gly Leu Pro Pro Arg Arg
1               5                   10

<210> SEQ ID NO 5
<211> LENGTH: 15
<212> TYPE: PRT
<213> ORGANISM: Unknown
<220> FEATURE:
<223> OTHER INFORMATION: exemplary peptide

<400> SEQUENCE: 5

Val Asn Asp Pro Ala Thr Asp Glu Thr Val Leu Ala Val Leu Ala
1 5 10 15

<210> SEQ ID NO 6
<211> LENGTH: 15
<212> TYPE: PRT
<213> ORGANISM: Unknown
<220> FEATURE:
<223> OTHER INFORMATION: consensus peptide

<400> SEQUENCE: 6

Pro Ala Thr Asp Glu Thr Val Leu Ala Val Leu Ala Asp Ile Ala
1 5 10 15

<210> SEQ ID NO 7
<211> LENGTH: 15
<212> TYPE: PRT
<213> ORGANISM: Unknown
<220> FEATURE:
<223> OTHER INFORMATION: Exemplary consensus peptide

<400> SEQUENCE: 7

Asp Glu Thr Val Leu Ala Val Leu Ala Asp Ile Ala Pro Ser Thr
1 5 10 15

<210> SEQ ID NO 8
<211> LENGTH: 14
<212> TYPE: PRT
<213> ORGANISM: Unknown
<220> FEATURE:
<223> OTHER INFORMATION: Exemplary consensus peptide

<400> SEQUENCE: 8

Lys Asp Glu Leu Ser Arg Gln Met Gly Leu Pro Pro Arg Arg
1 5 10

<210> SEQ ID NO 9
<211> LENGTH: 15
<212> TYPE: PRT
<213> ORGANISM: Unknown
<220> FEATURE:
<223> OTHER INFORMATION: Exemplary consensus peptide

<400> SEQUENCE: 9

Leu Ser Arg Gln Met Ala Gly Leu Pro Pro Arg Arg Leu Arg Arg
1 5 10 15

<210> SEQ ID NO 10
<211> LENGTH: 466
<212> TYPE: PRT
<213> ORGANISM: Unknown
<220> FEATURE:
<223> OTHER INFORMATION: Humanized antibody sequence shown in the format of 'Leader sequence-VH/VL-hIgG1CH/hIgKCL' for grafted VHI.

<400> SEQUENCE: 10

Met Gly Trp Ser Cys Ile Ile Leu Phe Leu Val Ala Thr Ala Thr Gly
1 5 10 15

Val His Ser Gln Val Gln Leu Val Gln Ser Gly Ala Glu Val Lys Lys
20 25 30

Pro Gly Ala Ser Val Lys Val Ser Cys Lys Ala Ser Gly Tyr Ser Phe
35 40 45

```
Thr Gly Tyr Phe Met Asn Trp Val Arg Gln Ala Pro Gly Gln Arg Leu
    50                  55                  60

Glu Trp Met Gly Arg Ile Asn Pro Tyr Asn Gly Asp Thr Phe Tyr Asn
65                  70                  75                  80

Gln Lys Phe Lys Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Asn His Tyr Thr Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460
```

Gly Lys
465

<210> SEQ ID NO 11
<211> LENGTH: 466
<212> TYPE: PRT
<213> ORGANISM: Unknown
<220> FEATURE:
<223> OTHER INFORMATION: Humanized antibody sequence shown in the format of 'Leader sequence-VH/VL-hIgG1CH/hIgKCL' for AHF00208-VH.

<400> SEQUENCE: 11

Met Gly Trp Ser Cys Ile Ile Leu Phe Leu Val Ala Thr Ala Thr Gly
1 5 10 15

Val His Ser Gln Val Gln Leu Val Gln Ser Gly Ala Glu Val Lys Lys
20 25 30

Pro Gly Ala Ser Val Lys Val Ser Cys Lys Ala Ser Gly Tyr Ser Phe
35 40 45

Thr Gly Tyr Phe Met Asn Trp Val Arg Gln Ala Pro Gly Gln Ser Leu
50 55 60

Glu Trp Met Gly Arg Ile Asn Pro Tyr Asn Gly Asp Thr Phe Tyr Asn
65 70 75 80

Gln Lys Phe Lys Gly Arg Val Thr Ile Thr Arg Asp Thr Ser Ala Ser
85 90 95

Thr Ala His Met Glu Leu Ser Ser Leu Arg Ser Glu Asp Thr Ala Val
100 105 110

Tyr Tyr Cys Ala Arg Gly Asn His Tyr Thr Met Asp Tyr Trp Gly Gln
115 120 125

Gly Thr Leu Val Thr Val Ser Ser Ala Ser Thr Lys Gly Pro Ser Val
130 135 140

Phe Pro Leu Ala Pro Ser Ser Lys Ser Thr Ser Gly Gly Thr Ala Ala
145 150 155 160

Leu Gly Cys Leu Val Lys Asp Tyr Phe Pro Glu Pro Val Thr Val Ser
165 170 175

Trp Asn Ser Gly Ala Leu Thr Ser Gly Val His Thr Phe Pro Ala Val
180 185 190

Leu Gln Ser Ser Gly Leu Tyr Ser Leu Ser Ser Val Val Thr Val Pro
195 200 205

Ser Ser Ser Leu Gly Thr Gln Thr Tyr Ile Cys Asn Val Asn His Lys
210 215 220

Pro Ser Asn Thr Lys Val Asp Lys Lys Val Glu Pro Lys Ser Cys Asp
225 230 235 240

Lys Thr His Thr Cys Pro Pro Cys Pro Ala Pro Glu Leu Leu Gly Gly
245 250 255

Pro Ser Val Phe Leu Phe Pro Pro Lys Pro Lys Asp Thr Leu Met Ile
260 265 270

Ser Arg Thr Pro Glu Val Thr Cys Val Val Val Asp Val Ser His Glu
275 280 285

Asp Pro Glu Val Lys Phe Asn Trp Tyr Val Asp Gly Val Glu Val His
290 295 300

Asn Ala Lys Thr Lys Pro Arg Glu Glu Gln Tyr Asn Ser Thr Tyr Arg
305 310 315 320

Val Val Ser Val Leu Thr Val Leu His Gln Asp Trp Leu Asn Gly Lys
325 330 335

Glu Tyr Lys Cys Lys Val Ser Asn Lys Ala Leu Pro Ala Pro Ile Glu
340 345 350

```
Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 12
<211> LENGTH: 466
<212> TYPE: PRT
<213> ORGANISM: Unknown
<220> FEATURE:
<223> OTHER INFORMATION: Humanized antibody sequence shown in the format
      of 'Leader sequence-VH/VL-hIgG1CH/hIgKCL' for AHF00217-VH.

<400> SEQUENCE: 12

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Gly Tyr Phe Met Asn Trp Val Arg Gln Ala Pro Gly Gln Arg Leu
    50                  55                  60

Glu Trp Met Gly Arg Ile Asn Pro Tyr Asn Gly Asp Thr Phe Tyr Asn
65                  70                  75                  80

Gln Lys Phe Lys Gly Arg Val Thr Ile Thr Arg Asp Thr Ser Ala Ser
                85                  90                  95

Thr Ala His Met Glu Leu Ser Ser Leu Arg Ser Glu Asp Thr Ala Val
            100                 105                 110

Tyr Tyr Cys Ala Arg Gly Asn His Tyr Thr Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220
```

Pro Ser Asn Thr Lys Val Asp Lys Lys Val Glu Pro Lys Ser Cys Asp
225 230 235 240

Lys Thr His Thr Cys Pro Pro Cys Pro Ala Pro Glu Leu Leu Gly Gly
245 250 255

Pro Ser Val Phe Leu Phe Pro Pro Lys Pro Lys Asp Thr Leu Met Ile
260 265 270

Ser Arg Thr Pro Glu Val Thr Cys Val Val Val Asp Val Ser His Glu
275 280 285

Asp Pro Glu Val Lys Phe Asn Trp Tyr Val Asp Gly Val Glu Val His
290 295 300

Asn Ala Lys Thr Lys Pro Arg Glu Glu Gln Tyr Asn Ser Thr Tyr Arg
305 310 315 320

Val Val Ser Val Leu Thr Val Leu His Gln Asp Trp Leu Asn Gly Lys
325 330 335

Glu Tyr Lys Cys Lys Val Ser Asn Lys Ala Leu Pro Ala Pro Ile Glu
340 345 350

Lys Thr Ile Ser Lys Ala Lys Gly Gln Pro Arg Glu Pro Gln Val Tyr
355 360 365

Thr Leu Pro Pro Ser Arg Asp Glu Leu Thr Lys Asn Gln Val Ser Leu
370 375 380

Thr Cys Leu Val Lys Gly Phe Tyr Pro Ser Asp Ile Ala Val Glu Trp
385 390 395 400

Glu Ser Asn Gly Gln Pro Glu Asn Asn Tyr Lys Thr Thr Pro Pro Val
405 410 415

Leu Asp Ser Asp Gly Ser Phe Phe Leu Tyr Ser Lys Leu Thr Val Asp
420 425 430

Lys Ser Arg Trp Gln Gln Gly Asn Val Phe Ser Cys Ser Val Met His
435 440 445

Glu Ala Leu His Asn His Tyr Thr Gln Lys Ser Leu Ser Leu Ser Pro
450 455 460

Gly Lys
465

<210> SEQ ID NO 13
<211> LENGTH: 466
<212> TYPE: PRT
<213> ORGANISM: Unknown
<220> FEATURE:
<223> OTHER INFORMATION: Humanized antibody sequence shown in the format of 'Leader sequence-VH/VL-hIgG1CH/hIgKCL' for AHF00220-VH.

<400> SEQUENCE: 13

Met Gly Trp Ser Cys Ile Ile Leu Phe Leu Val Ala Thr Ala Thr Gly
1 5 10 15

Val His Ser Gln Val Gln Leu Val Gln Ser Gly Ala Glu Val Lys Lys
20 25 30

Pro Gly Ala Ser Val Lys Val Ser Cys Lys Ala Ser Gly Tyr Ser Phe
35 40 45

Thr Gly Tyr Phe Met Asn Trp Val Arg Gln Ala Pro Gly Gln Ser Leu
50 55 60

Glu Trp Ile Gly Arg Ile Asn Pro Tyr Asn Gly Asp Thr Phe Tyr Asn
65 70 75 80

Gln Lys Phe Lys Gly Arg Val Thr Ile Thr Arg Asp Thr Ser Ala Ser
85 90 95

Thr Ala Tyr Met Glu Leu Ser Ser Leu Arg Ser Glu Asp Thr Ala Val
100 105 110

Tyr Tyr Cys Ala Arg Gly Asn His Tyr Thr Met Asp Tyr Trp Gly Gln
115 120 125

Gly Thr Leu Val Thr Val Ser Ser Ala Ser Thr Lys Gly Pro Ser Val
130 135 140

Phe Pro Leu Ala Pro Ser Ser Lys Ser Thr Ser Gly Gly Thr Ala Ala
145 150 155 160

Leu Gly Cys Leu Val Lys Asp Tyr Phe Pro Glu Pro Val Thr Val Ser
165 170 175

Trp Asn Ser Gly Ala Leu Thr Ser Gly Val His Thr Phe Pro Ala Val
180 185 190

Leu Gln Ser Ser Gly Leu Tyr Ser Leu Ser Ser Val Val Thr Val Pro
195 200 205

Ser Ser Ser Leu Gly Thr Gln Thr Tyr Ile Cys Asn Val Asn His Lys
210 215 220

Pro Ser Asn Thr Lys Val Asp Lys Lys Val Glu Pro Lys Ser Cys Asp
225 230 235 240

Lys Thr His Thr Cys Pro Pro Cys Pro Ala Pro Glu Leu Leu Gly Gly
245 250 255

Pro Ser Val Phe Leu Phe Pro Pro Lys Pro Lys Asp Thr Leu Met Ile
260 265 270

Ser Arg Thr Pro Glu Val Thr Cys Val Val Val Asp Val Ser His Glu
275 280 285

Asp Pro Glu Val Lys Phe Asn Trp Tyr Val Asp Gly Val Glu Val His
290 295 300

Asn Ala Lys Thr Lys Pro Arg Glu Glu Gln Tyr Asn Ser Thr Tyr Arg
305 310 315 320

Val Val Ser Val Leu Thr Val Leu His Gln Asp Trp Leu Asn Gly Lys
325 330 335

Glu Tyr Lys Cys Lys Val Ser Asn Lys Ala Leu Pro Ala Pro Ile Glu
340 345 350

Lys Thr Ile Ser Lys Ala Lys Gly Gln Pro Arg Glu Pro Gln Val Tyr
355 360 365

Thr Leu Pro Pro Ser Arg Asp Glu Leu Thr Lys Asn Gln Val Ser Leu
370 375 380

Thr Cys Leu Val Lys Gly Phe Tyr Pro Ser Asp Ile Ala Val Glu Trp
385 390 395 400

Glu Ser Asn Gly Gln Pro Glu Asn Asn Tyr Lys Thr Thr Pro Pro Val
405 410 415

Leu Asp Ser Asp Gly Ser Phe Phe Leu Tyr Ser Lys Leu Thr Val Asp
420 425 430

Lys Ser Arg Trp Gln Gln Gly Asn Val Phe Ser Cys Ser Val Met His
435 440 445

Glu Ala Leu His Asn His Tyr Thr Gln Lys Ser Leu Ser Leu Ser Pro
450 455 460

Gly Lys
465

<210> SEQ ID NO 14
<211> LENGTH: 233
<212> TYPE: PRT
<213> ORGANISM: Unknown
<220> FEATURE:

<223> OTHER INFORMATION: Humanized antibody sequence shown in the format of 'Leader sequence-VH/VL-hIgG1CH/hIgKCL' for Light chain Grafted-VL1 (AHF00208-VL= AHF00220-VL).

<400> SEQUENCE: 14

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Asp Ile
        35                  40                  45

Asn Ser Tyr Leu Ser Trp Tyr Gln Gln Lys Pro Gly Lys Ala Pro Lys
    50                  55                  60

Leu Leu Ile Tyr Arg Ala Asn Arg Leu Val Asp Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Leu Gln Tyr Asp Glu
            100                 105                 110

Phe Pro Leu Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 15
<211> LENGTH: 233
<212> TYPE: PRT
<213> ORGANISM: Unknown
<220> FEATURE:
<223> OTHER INFORMATION: Humanized antibody sequence shown in the format of 'Leader sequence-VH/VL-hIgG1CH/hIgKCL' for AHF00217-VL.

<400> SEQUENCE: 15

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Asp Ile
        35                  40                  45

Asn Ser Tyr Leu Ser Trp Tyr Gln Gln Lys Pro Gly Lys Ala Pro Lys
    50                  55                  60

Leu Leu Ile Tyr Arg Ala Asn Arg Leu Val Asp Gly Val Pro Ser Arg
65                  70                  75                  80

Phe Ser Gly Ser Gly Ser Gly Thr Asp Tyr Thr Phe Thr Ile Ser Ser
                85                  90                  95
```

```
Leu Gln Pro Glu Asp Ile Ala Thr Tyr Tyr Cys Leu Gln Tyr Asp Glu
            100                 105                 110

Phe Pro Leu Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 16
<211> LENGTH: 1401
<212> TYPE: DNA
<213> ORGANISM: Unknown
<220> FEATURE:
<223> OTHER INFORMATION: Nucleotide sequence that encodes the heavy
      chain of the humanized antibody sequence identified above as
      Grafted Ab-VH.

<400> SEQUENCE: 16

atgggctgga gctggatcct gctgttcctc ctgagcgtga cagcaggagt gcacagccag     60

gtgcagctgg tgcagtccgg agcagaggtg aagaagccag gagcctctgt gaaggtgagc    120

tgcaaggcca gcggctactc cttcaccggc tacttcatga actgggtgag gcaggcacca    180

ggacagcgcc tggagtggat gggccggatc aacccttaca atggcgacac attctataat    240

cagaagttta agggccgggt gaccatcaca agagatacct ccgcctctac agcctacatg    300

gagctgagct ccctgaggtc tgaggacacc gccgtgtact attgtgcccg gggcaaccac    360

tacacaatgg attattgggg ccagggcacc ctggtgacag tgtctagcgc tagcaccaag    420

ggcccatcgg tcttccccct ggcaccctcc tccaagagca cctctggggg cacagcggcc    480

ctgggctgcc tggtcaagga ctacttcccc gaaccggtga cggtgtcgtg gaactcaggc    540

gccctgacca gcggcgtgca caccttcccg gctgtcctac agtcctcagg actctactcc    600

ctcagcagcg tggtgaccgt gccctccagc agcttgggca cccagaccta catctgcaac    660

gtgaatcaca agcccagcaa caccaaggtg gacaagaaag ttgagcccaa atcttgtgac    720

aaaactcaca catgcccacc gtgcccagca cctgaactcc tggggggacc gtcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccg cgggaggagc agtacaacag cacgtaccgt    960

gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtacaccctg cccccatccc gggatgagct gaccaagaac   1140

caggtcagcc tgacctgcct ggtcaaaggc ttctatccca gcgacatcgc cgtggagtgg   1200
```

gagagcaatg ggcagccgga gaacaactac aagaccacgc ctcccgtgct ggactccgac 1260
ggctccttct tcctctacag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaatg a 1401

<210> SEQ ID NO 17
<211> LENGTH: 1401
<212> TYPE: DNA
<213> ORGANISM: Unknown
<220> FEATURE:
<223> OTHER INFORMATION: Exemplary nucleotide sequence that encodes the heavy chain of the humanized antibody sequence identified above as >AHF00208-VH.

<400> SEQUENCE: 17
atgggctgga gctggatcct gctgttcctc ctgagcgtga cagcaggagt gcacagccag 60
gtgcagctgg tgcagtccgg agcagaggtg aagaagccag gagcctctgt gaaggtgagc 120
tgcaaggcca gcggctactc cttcaccggc tacttcatga actgggtgcg gcaggcacca 180
ggacagtctc tggagtggat gggcaggatc aacccttaca atggcgacac attctataat 240
cagaagttta agggccgggt gaccatcaca agagatacct ccgcctctac agcccacatg 300
gagctgagct ccctgaggag cgaggacacc gccgtgtact attgtgcccg cggcaaccac 360
tacacaatgg attattgggg ccagggcacc ctggtgacag tgtctagcgc tagcaccaag 420
ggcccatcgg tcttccccct ggcaccctcc tccaagagca cctctggggg cacagcggcc 480
ctgggctgcc tggtcaagga ctacttcccc gaaccggtga cggtgtcgtg gaactcaggc 540
gccctgacca gcggcgtgca caccttcccg gctgtcctac agtcctcagg actctactcc 600
ctcagcagcg tggtgaccgt gccctccagc agcttgggca cccagaccta catctgcaac 660
gtgaatcaca agcccagcaa caccaaggtg gacaagaaag ttgagcccaa atcttgtgac 720
aaaactcaca catgcccacc gtgcccagca cctgaactcc tggggggacc gtcagtcttc 780
ctcttccccc caaaacccaa ggacaccctc atgatctccc ggacccctga ggtcacatgc 840
gtggtggtgg acgtgagcca cgaagaccct gaggtcaagt tcaactggta cgtggacggc 900
gtggaggtgc ataatgccaa gacaaagccg cgggaggagc agtacaacag cacgtaccgt 960
gtggtcagcg tcctcaccgt cctgcaccag gactggctga atggcaagga gtacaagtgc 1020
aaggtctcca acaaagccct cccagccccc atcgagaaaa ccatctccaa agccaaaggg 1080
cagccccgag aaccacaggt gtacaccctg cccccatccc gggatgagct gaccaagaac 1140
caggtcagcc tgacctgcct ggtcaaaggc ttctatccca gcgacatcgc cgtggagtgg 1200
gagagcaatg ggcagccgga gaacaactac aagaccacgc ctcccgtgct ggactccgac 1260
ggctccttct tcctctacag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaatg a 1401

<210> SEQ ID NO 18
<211> LENGTH: 1401
<212> TYPE: DNA
<213> ORGANISM: Unknown
<220> FEATURE:
<223> OTHER INFORMATION: Exemplary nucleotide sequence that encodes the heavy chain of the humanized antibody sequence identified above as AHF00217-VH.

<400> SEQUENCE: 18
atgggctgga gctggatcct gctgttcctc ctgagcgtga cagcaggagt gcacagccag 60
gtgcagctgg tgcagtccgg agcagaggtg aagaagccag gagcctctgt gaaggtgagc 120
tgcaaggcca gcggctactc cttcaccggc tacttcatga actgggtgag gcaggcacca 180
ggacagcgcc tggagtggat gggccggatc aacccttaca atggcgacac attctataat 240
cagaagttta agggccgggt gaccatcaca agagatacct ccgcctctac agcccacatg 300
gagctgagct ccctgaggtc tgaggacacc gccgtgtact attgtgcccg gggcaaccac 360
tacacaatgg attattgggg ccagggcacc ctggtgacag tgtctagcgc tagcaccaag 420
ggcccatcgg tcttcccct ggcaccctcc tccaagagca cctctggggg cacagcggcc 480
ctgggctgcc tggtcaagga ctacttcccc gaaccggtga cggtgtcgtg gaactcaggc 540
gccctgacca gcggcgtgca caccttcccg gctgtcctac agtcctcagg actctactcc 600
ctcagcagcg tggtgaccgt gccctccagc agcttgggca cccagaccta catctgcaac 660
gtgaatcaca agcccagcaa caccaaggtg gacaagaaag ttgagcccaa atcttgtgac 720
aaaactcaca catgcccacc gtgcccagca cctgaactcc tggggggacc gtcagtcttc 780
ctcttccccc caaaacccaa ggacaccctc atgatctccc ggacccctga ggtcacatgc 840
gtggtggtgg acgtgagcca cgaagaccct gaggtcaagt tcaactggta cgtggacggc 900
gtggaggtgc ataatgccaa gacaaagccg cgggaggagc agtacaacag cacgtaccgt 960
gtggtcagcg tcctcaccgt cctgcaccag gactggctga atggcaagga gtacaagtgc 1020
aaggtctcca acaaagccct cccagccccc atcgagaaaa ccatctccaa agccaaaggg 1080
cagccccgag aaccacaggt gtacaccctg cccccatccc gggatgagct gaccaagaac 1140
caggtcagcc tgacctgcct ggtcaaaggc ttctatccca gcgacatcgc cgtggagtgg 1200
gagagcaatg ggcagccgga gaacaactac aagaccacgc ctcccgtgct ggactccgac 1260
ggctccttct tcctctacag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaatg a 1401

<210> SEQ ID NO 19
<211> LENGTH: 1401
<212> TYPE: DNA
<213> ORGANISM: Unknown
<220> FEATURE:
<223> OTHER INFORMATION: Exemplary nucleotide sequence that encodes the heavy chain of the humanized antibody sequence identified above as AHF00220-VH.

<400> SEQUENCE: 19
atgggctgga gctggatcct gctgttcctc ctgagcgtga cagcaggagt gcacagccag 60
gtgcagctgg tgcagtccgg agcagaggtg aagaagccag gagcctctgt gaaggtgagc 120
tgcaaggcca gcggctactc cttcaccggc tacttcatga actgggtgcg gcaggcacca 180
ggacagtctc tggagtggat cggcaggatc aacccttaca atggcgacac attctataat 240
cagaagttta agggccgggt gaccatcaca agagatacct ccgcctctac agcctacatg 300
gagctgagct ccctgaggag cgaggacacc gccgtgtact attgtgcccg cggcaaccac 360
tacacaatgg attattgggg ccagggcacc ctggtgacag tgtctagcgc tagcaccaag 420
ggcccatcgg tcttcccct ggcaccctcc tccaagagca cctctggggg cacagcggcc 480
ctgggctgcc tggtcaagga ctacttcccc gaaccggtga cggtgtcgtg gaactcaggc 540

```
gccctgacca gcggcgtgca caccttcccg gctgtcctac agtcctcagg actctactcc    600

ctcagcagcg tggtgaccgt gccctccagc agcttgggca cccagaccta catctgcaac    660

gtgaatcaca agcccagcaa caccaaggtg gacaagaaag ttgagcccaa atcttgtgac    720

aaaactcaca catgcccacc gtgcccagca cctgaactcc tggggggacc gtcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccg cgggaggagc agtacaacag cacgtaccgt    960

gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtacaccctg cccccatccc gggatgagct gaccaagaac   1140

caggtcagcc tgacctgcct ggtcaaaggc ttctatccca gcgacatcgc cgtggagtgg   1200

gagagcaatg ggcagccgga gaacaactac aagaccacgc ctcccgtgct ggactccgac   1260

ggctccttct tcctctacag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaatg a                                             1401
```

```
<210> SEQ ID NO 20
<211> LENGTH: 702
<212> TYPE: DNA
<213> ORGANISM: Unknown
<220> FEATURE:
<223> OTHER INFORMATION: DNA sequence of the Light chain of Grafted
      Ab-VL (AHF00208-VL= AHF00220-VL) as referred to above.

<400> SEQUENCE: 20

atgggctgga gctggatcct gctgttcctc ctgagcgtga cagcaggagt gcacagcgac     60

atccagatga cccagtctcc tagctccctg tccgcctctg tgggcgacag ggtgaccatc    120

acatgcaagg ccagccagga tatcaacagc tacctgtcct ggtatcagca gaagcccggc    180

aaggccccta agctgctgat ctaccgggcc aatagactgg tggacggagt gccatcccgg    240

ttcagcggat ccggctctgg caccgatttc acctttacaa tctctagcct gcagccagag    300

gacatcgcca catactattg tctgcagtat gatgagttcc ccctgacctt tggcggcggc    360

acaaagctgg agatcaagcg aacggtggct gcaccatctg tcttcatctt cccgccatct    420

gatgagcagt tgaaatctgg aactgcctct gttgtgtgcc tgctgaataa cttctatccc    480

agagaggcca aagtacagtg gaaggtggat aacgccctcc aatcgggtaa ctcccaggag    540

agtgtcacag agcaggacag caaggacagc acctacagcc tcagcagcac cctgacgctg    600

agcaaagcag actacgagaa acacaaagtc tacgcctgcg aagtcaccca tcagggcctg    660

agctcgcccg tcacaaagag cttcaacagg ggagagtgtt ag                      702


<210> SEQ ID NO 21
<211> LENGTH: 702
<212> TYPE: DNA
<213> ORGANISM: Unknown
<220> FEATURE:
<223> OTHER INFORMATION: DNA sequence of the AHF00217-VL

<400> SEQUENCE: 21

atgggctgga gctggatcct gctgttcctc ctgagcgtga cagcaggagt gcacagcgac     60

atccagatga cccagtctcc tagctccctg tccgcctctg tgggcgacag ggtgaccatc    120
```

```
acatgcaagg ccagccagga tatcaacagc tacctgtcct ggtatcagca gaagcccggc    180

aaggccccta agctgctgat ctaccgggcc aatagactgg tggacggagt gccatcccgg    240

ttcagcggat ccggctctgg caccgattac acctttacaa tctctagcct gcagccagag    300

gacatcgcca catactattg tctgcagtat gatgagttcc ccctgacctt tggcggcggc    360

acaaagctgg agatcaagcg aacggtggct gcaccatctg tcttcatctt cccgccatct    420

gatgagcagt tgaaatctgg aactgcctct gttgtgtgcc tgctgaataa cttctatccc    480

agagaggcca aagtacagtg gaaggtggat aacgccctcc aatcgggtaa ctcccaggag    540

agtgtcacag agcaggacag caaggacagc acctacagcc tcagcagcac cctgacgctg    600

agcaaagcag actacgagaa acacaaagtc tacgcctgcg aagtcaccca tcagggcctg    660

agctcgcccg tcacaaagag cttcaacagg ggagagtgtt ag                       702
```

```
<210> SEQ ID NO 22
<211> LENGTH: 117
<212> TYPE: PRT
<213> ORGANISM: Unknown
<220> FEATURE:
<223> OTHER INFORMATION: grafted VHI - VH

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Phe Met Asn Trp Val Arg Gln Ala Pro Gly Gln Arg Leu Glu Trp Met
        35                  40                  45

Gly Arg Ile Asn Pro Tyr Asn Gly Asp Thr Phe Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn His Tyr Thr Met Asp Tyr Trp Gly Gln Gly Thr Leu
            100                 105                 110

Val Thr Val Ser Ser
        115


<210> SEQ ID NO 23
<211> LENGTH: 117
<212> TYPE: PRT
<213> ORGANISM: Unknown
<220> FEATURE:
<223> OTHER INFORMATION: AHF00208-VH

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Phe Met Asn Trp Val Arg Gln Ala Pro Gly Gln Ser Leu Glu Trp Met
        35                  40                  45

Gly Arg Ile Asn Pro Tyr Asn Gly Asp Thr Phe Tyr Asn Gln Lys Phe
    50                  55                  60

Lys Gly Arg Val Thr Ile Thr Arg Asp Thr Ser Ala Ser Thr Ala His
65                  70                  75                  80
```

```
Met Glu Leu Ser Ser Leu Arg Ser Glu Asp Thr Ala Val Tyr Tyr Cys
                85                  90                  95

Ala Arg Gly Asn His Tyr Thr Met Asp Tyr Trp Gly Gln Gly Thr Leu
            100                 105                 110

Val Thr Val Ser Ser
        115


<210> SEQ ID NO 24
<211> LENGTH: 120
<212> TYPE: PRT
<213> ORGANISM: Unknown
<220> FEATURE:
<223> OTHER INFORMATION: AHF00217-VH

<400> SEQUENCE: 24

Val His Ser Gln Val Gln Leu Val Gln Ser Gly Ala Glu Val Lys Lys
1               5                   10                  15

Pro Gly Ala Ser Val Lys Val Ser Cys Lys Ala Ser Gly Tyr Ser Phe
            20                  25                  30

Thr Gly Tyr Phe Met Asn Trp Val Arg Gln Ala Pro Gly Gln Arg Leu
        35                  40                  45

Glu Trp Met Gly Arg Ile Asn Pro Tyr Asn Gly Asp Thr Phe Tyr Asn
    50                  55                  60

Gln Lys Phe Lys Gly Arg Val Thr Ile Thr Arg Asp Thr Ser Ala Ser
65                  70                  75                  80

Thr Ala His Met Glu Leu Ser Ser Leu Arg Ser Glu Asp Thr Ala Val
                85                  90                  95

Tyr Tyr Cys Ala Arg Gly Asn His Tyr Thr Met Asp Tyr Trp Gly Gln
            100                 105                 110

Gly Thr Leu Val Thr Val Ser Ser
        115                 120


<210> SEQ ID NO 25
<211> LENGTH: 117
<212> TYPE: PRT
<213> ORGANISM: Unknown
<220> FEATURE:
<223> OTHER INFORMATION: AHF00220-VH

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Phe Met Asn Trp Val Arg Gln Ala Pro Gly Gln Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn His Tyr Thr Met Asp Tyr Trp Gly Gln Gly Thr Leu
            100                 105                 110

Val Thr Val Ser Ser
        115
```

-continued

<210> SEQ ID NO 26
<211> LENGTH: 107
<212> TYPE: PRT
<213> ORGANISM: Unknown
<220> FEATURE:
<223> OTHER INFORMATION: AHF00208-VL= AHF00220-VL

<400> SEQUENCE: 26

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Leu Gln Tyr Asp Glu Phe Pro Leu
85 90 95

Thr Phe Gly Gly Gly Thr Lys Leu Glu Ile Lys
100 105

<210> SEQ ID NO 27
<211> LENGTH: 107
<212> TYPE: PRT
<213> ORGANISM: Unknown
<220> FEATURE:
<223> OTHER INFORMATION: AHF00217-VL

<400> SEQUENCE: 27

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Phe Thr Ile Ser Ser Leu Gln Pro
65 70 75 80

Glu Asp Ile Ala Thr Tyr Tyr Cys Leu Gln Tyr Asp Glu Phe Pro Leu
85 90 95

Thr Phe Gly Gly Gly Thr Lys Leu Glu Ile Lys
100 105

What is claimed is:

1. An isolated antibody or an antigen-binding fragment thereof, comprising:

(i) a Variable Heavy Chain (VH) domain sequence comprising SEQ ID NO:23; and a Variable Light Chain (VL) domain sequence comprising SEQ ID NO: 26;

(ii) a VH domain sequence comprising SEQ ID NO:24 and a VL domain sequence comprising SEQ ID NO: 27 or (iii) a VH domain sequence comprising SEQ ID NO:25 and a VL domain sequence comprising SEQ ID NO: 26.

2. A composition, comprising:

the isolated antibody or the antigen-binding fragment of claim 1; and a pharmaceutically-acceptable buffer, diluent, carrier, or vehicle.

3. The composition of claim 2, further comprising an adjuvant.

4. The composition of claim 2, further comprising a chemotherapeutic agent, an immunomodulating agent, a neuroactive agent, an anti-inflammatory agent, an anti-lipidemic agent, a hormone, a receptor agonist, a receptor antagonist, an anti-infective agent, a protein, a peptide, an antibody, an antigen-binding fragment of an antibody, an RNA molecule, a DNA molecule, an siRNA molecule, an mRNA molecule, a ribozyme, a hormone, a cofactor, a steroid, an antisense nucleic acid, or any combination of any thereof.

5. The composition of claim 4, wherein the chemotherapeutic agent comprises one or more antineoplastic compounds, one or more cytotoxic compounds, one or more cytostatic compounds, or any combination of any thereof.

6. The composition of claim 4, wherein the chemotherapeutic agent is cyclophosphamide, doxorubicin, 5 fluorouracil, docetaxel, paclitaxel, trastuzumab, methotrexate, epirubicin, cisplatin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, or any combination of any thereof.

7. A kit, comprising:

a composition, comprising the isolated antibody or antigen-binding fragment thereof of claim 1; and instructions for administering a composition to a subject in need thereof, as part of a regimen for the diagnosis, treatment, or amelioration of one or more symptoms of cancer.

8. A method of treating or ameliorating one or more symptoms of cancer in a subject in need thereof, the method comprising:

administering to the subject an effective amount of the isolated antibody or antigen-binding fragment thereof of claim 1 for a time sufficient to treat or ameliorate the one or more symptoms of the cancer in the subject.

9. The method of claim 8, wherein the cancer is a refractory, a metastatic, a relapsed, or a treatment resistant cancer.

10. The method of claim 8, wherein the cancer is a tumorigenic cancer.

11. The method of claim 10, wherein the cancer is ovarian cancer or pancreatic cancer.

12. The method of claim 8, wherein the subject is a mammal.

13. The method of claim 8, further comprising administering a therapeutically effective amount of ionizing radiation, a second distinct antibody, a second distinct chemotherapeutic agent, or any combination of any thereof, to the subject.

14. A method of reducing a level of biologically-active MFAP5 polypeptide in a subject in need thereof, the method comprising:

administering to the subject in need thereof the isolated antibody or antigen-binding fragment of claim 1 in an amount effective and for a time sufficient to reduce the level of biologically-active MFAP5 polypeptide in the subject in need thereof.

15. The method of claim 14, wherein the subject in need thereof has a cancer that is a refractory, a metastatic, a relapsed, or a treatment resistant cancer.

16. The method of claim 14, wherein the subject in need thereof has been diagnosed with a tumorigenic cancer.

17. The method of claim 16, wherein the cancer is ovarian cancer or pancreatic cancer.

18. A method of reducing the degree of fibrosis or the extent of collagen development in the tumor microenvironment of a subject diagnosed with cancer, comprising:

administering to the subject the isolated antibody or antigen-binding fragment of claim 1 in an amount effective and for a time sufficient to reduce the degree of fibrosis or the extent of collagen development in the subject.

19. The method of claim 18, wherein the cancer is a refractory, a metastatic, a relapsed, or a treatment resistant cancer.

20. The method of claim 19, wherein the subject has been diagnosed with a tumorigenic cancer.

21. The method of claim 20, wherein the subject has been diagnosed with ovarian cancer or pancreatic cancer.

22. A method for inhibiting cancer cell motility or suppressing tumor progression in a subject, comprising:

administering to the subject the isolated antibody or antigen-binding fragment of claim 1 in an amount effective and for a time sufficient to inhibit motility of one or more cancer cells or to suppress progression of one or more tumors in the subject.

23. The method of claim 22, wherein the one or more cancer cells are ovarian cancer cells or pancreatic cancer cells or wherein the one or more tumors are pancreatic tumors or ovarian tumors.

24. A diagnostic composition, comprising the isolated antibody or the antigen-binding fragment of claim 1, and a detectable label.

25. The diagnostic composition of claim 24, wherein the detectable label is a radiolabel or reporter agent detectable by immunofluorescence.

26. The isolated antibody or an antigen-binding fragment thereof of claim 1, wherein the VH domain comprises SEQ ID NO:23, and wherein the VL domain comprises SEQ ID NO:26.

27. The isolated antibody or an antigen-binding fragment thereof of claim 1, wherein the VH domain comprises SEQ ID NO:24, and wherein the VL domain comprises SEQ ID NO:27.

28. The isolated antibody or an antigen-binding fragment thereof of claim 1, wherein the VH domain comprises SEQ ID NO:25, and wherein the VL domain comprises SEQ ID NO:26.

* * * * *